(12) United States Patent
Mak

(10) Patent No.: US 11,821,013 B2
(45) Date of Patent: Nov. 21, 2023

(54) BLOOD GLUCOSE STABILIZING METHODS AND COMPOSITIONS

(71) Applicant: Digestiva, Inc., Sacramento, CA (US)

(72) Inventor: Wai Shun Mak, Sacramento, CA (US)

(73) Assignee: Digestiva, Inc., Sacramento, CA (US)

( * ) Notice: Subject to any disclaimer, the term of this patent is extended or adjusted under 35 U.S.C. 154(b) by 0 days.

(21) Appl. No.: 18/184,476

(22) Filed: Mar. 15, 2023

(65) Prior Publication Data

US 2023/0257729 A1    Aug. 17, 2023

Related U.S. Application Data

(63) Continuation of application No. PCT/US2023/061253, filed on Jan. 25, 2023.

(60) Provisional application No. 63/303,112, filed on Jan. 26, 2022.

(51) Int. Cl.

| | | |
|---|---|---|
| *C12N 9/64* | (2006.01) | |
| *A61K 9/00* | (2006.01) | |
| *A61P 3/08* | (2006.01) | |
| *A61K 36/48* | (2006.01) | |

(52) U.S. Cl.
CPC .......... *C12N 9/6424* (2013.01); *A61K 9/0056* (2013.01); *A61K 36/48* (2013.01); *A61P 3/08* (2018.01)

(58) Field of Classification Search
CPC .................................................. C12N 9/6424
See application file for complete search history.

(56) References Cited

U.S. PATENT DOCUMENTS

| | | | |
|---|---|---|---|
| 3,097,145 A | 7/1963 | Hirao et al. | |
| 7,320,788 B2 | 1/2008 | Shan et al. | |
| 2003/0109020 A1 | 6/2003 | Lobel et al. | |
| 2005/0249719 A1 | 11/2005 | Shan et al. | |
| 2007/0083334 A1 | 4/2007 | Mintz et al. | |
| 2009/0029005 A1 | 1/2009 | Van Amerongen et al. | |
| 2013/0034530 A1 | 2/2013 | Fantz | |
| 2013/0121915 A1 | 5/2013 | Paas et al. | |
| 2016/0194621 A1 | 7/2016 | Siegel et al. | |
| 2018/0185458 A1 | 7/2018 | Siegel et al. | |
| 2019/0230958 A1* | 8/2019 | Michels ................. | A23K 50/00 |
| 2019/0322994 A1 | 10/2019 | Michels et al. | |
| 2020/0383351 A1 | 12/2020 | Siegel et al. | |
| 2021/0386089 A1 | 12/2021 | Siegel et al. | |

FOREIGN PATENT DOCUMENTS

| | | |
|---|---|---|
| CN | 101455368 A | 6/2009 |
| JP | H05244957 A | 9/1993 |
| JP | 2002078489 A | 3/2002 |
| WO | WO-2007088062 A2 | 8/2007 |
| WO | WO-2013096000 A1 | 6/2013 |
| WO | 2014037438 A1 | 3/2014 |
| WO | WO-2017147060 A9 | 9/2017 |
| WO | WO-2020087017 A1 | 4/2020 |

OTHER PUBLICATIONS

International Search Report And Written Opinion For Patent Application No. PCT/US2023/061253, dated Apr. 28, 2023, 5 pages.
Database Genbank, (Oct. 22, 2016) "Kumamolisin [*Modestobacter* sp. DSM 44400]", GenBank: SDY19074.1, 2 pages.
Database Genbank, (Aug. 29, 2014) "Putative family S53 Non-peptidase [Fimbriimonas Ginsengisoli Gsoil 348]", GenBank: AIE84354.1, 2 pages.
Database Genbank, (May 3, 2023) "RecName: Full=Pseudomonalisin; AltName: Full=Pepstatin-insensitive carboxyl proteinase; AltName: Full=Pseudomonapepsin; Flags: Precursor", UniProtKB/Swiss-Prot: P42790.1, 4 pages.
Database Genbank, (Mar. 25, 2023) "S53 Family Peptidase [Bradyrhizobium erythrophlei]", NCBI Reference Sequence: WP_074275535.1, 2 pages.
Database Genbank, (Mar. 25, 2023) "S53 Family Peptidase [Burkholderiaceae bacterium 26]", NCBI Reference Sequence: WP_045201751.1, 2 pages.
Database Genbank, (Mar. 25, 2023) "S53 Family Peptidase [*Mucilaginibacter* sp. OK098]", NCBI Reference Sequence: WP_073407649.1, 2 pages.
Database Genbank, (Mar. 25, 2023) "S53 Family Peptidase [Pandoraea thiooxydans]", NCBI Reference Sequence: WP_047214193.1, 2 pages.
Database Genbank, (Mar. 25, 2023) "S53 Family Peptidase [Paraburkholderia sacchari]", NCBI Reference Sequence: WP_035521184.1, 2 pages.
Database Genbank, (Mar. 25, 2023) "S53 Family Peptidase [*Variovorax* sp. HW608]", NCBI Reference Sequence: WP_088952683.1, 2 pages.
Database Genbank, (Mar. 25, 2023) "S53 Family Peptidase [Xanthomonas translucens]", NCBI Reference Sequence: WP_003471348.1, 2 pages.
Database Genbank, (Mar. 25, 2023) "S53 Family Peptidase [Xanthomonas translucens]", NCBI Reference Sequence: WP_058362273.1, 2 pages.
Li et al. (Mar. 2017) "Phylogenomic Evolutionary Surveys Of Subtilase Superfamily Genes In Fungi", Scientific Reports, 7(1):45456.
Altschul et al. Basic Local Alignment Search Tool. J. Mol. Biol. 215:403-410 (1990).
Altschul, et al. Gapped BLAST and PSI-BLAST: a new generation of protein database search programs. Nucleic Acids Res 25:3389-3402 (1997).
Astwood et al. Stability of food allergens to digestion in vitro. Nat Biotech 14(10):1269-1273 (1996).
Drozdetskiy et al., JPred4: a protein secondary structure prediction server. Nucleic Acids Res 43(W1):W389-W394 (2015).
Elango et al., Available versus digestible amino acids—new stable isotope methods. British Journal of Nutrition 108(S2):S306-S314 (2012).

(Continued)

*Primary Examiner* — Suzanne M Noakes

(74) *Attorney, Agent, or Firm* — Mintz Levin Cohn Ferris Glovsky and Popeo, P.C.

(57) ABSTRACT

Provided and described herein are methods and compositions for decreasing blood glucose, reducing an increase in blood glucose, and/or lowering the glycemic index of a foodstuff.

29 Claims, 3 Drawing Sheets

Specification includes a Sequence Listing.

(56) References Cited

OTHER PUBLICATIONS

Fu et al. Digestibility of food allergens and nonallergenic proteins in simulated gastric fluid and simulated intestinal fluid a comparative study. J Agric Food Chem 50(24):7154-7160 (2002).
Higgins et al. Using CLUSTAL for multiple sequence alignments. Methods Enzymol 266:383-402 (1994).
Kantor et al. Genome-Resolved Meta-Omics Ties Microbial Dynamics to Process Performance in Biotechnology for Thiocyanate Degradation. Enviorn Sci Technol 51(5):2944-2953 (2017).
Kantor et al. Peptidase S53 [*Pseudonocardia* sp. 73-21]. GenBank: OJY50246.1. Submitted Dec. 9, 2016: downloaded from the internet ncbi.nlm.nih.gov/protein/OJY50246.1?report=genbank&log$=protalign&blast_rank=1&RID=5331MAN1016 (accessed on Apr. 28, 2020), pp. 1-2.
Karlin, et al. Applications and statistics for multiple high-scoring segments in molecular sequences. PNAS USA 90:5873-5877 (1993).
Karlin et al. Methods for assessing the statistical significance of molecular sequence features by using general scoring schemes. PNAS USA 87:2264-2268 (1990).
Koopman et al., Ingestion of a protein hydrolysate is accompanied by an accelerated in vivo digestion and absorption rate when compared with its intact protein. Am J Clin Nutr 90(1):106-115 (2009).
Lee et al., Research Approaches and Methods for Evaluating the Protein Quality of Human Foods Proposed by an FAO Expert Working Group in 2014. J Nut 146(5):929-932 (2016).
Mandalari et al., In vitro digestibility of β-casein and β-lactoglobulin under simulated human gastric and duodenal conditions: a multilaboratory evaluation. Regulatory Toxicology and Pharmacology 55(3):372-381 (2009).
Matthews et al., Peptide absorption. Gastroenterology 71(1):151-161 (1976).
Migurcova., Chapter 13: Seaweed digestibility and methods used for digestibility determination. Handbook of Marine Macroalgae: Biotechnology and Applied Phycology pp. 285-301 (2011).
Millward et al., Protein quality assessment: impact of expanding understanding of protein and amino acid needs for optimal health. Am J Clin Nutr 87(5):1576S-1581S (2008).
Moughan., Amino acid availability: aspects of chemical analysis and bioassay methodology. Nutr Res Rev 16(2):127-141 (2003).
Oben et al., An open label study to determine the effects of an oral proteolytic enzyme system on whey protein concentrate metabolism in healthy males. J Int Soc Sports Nutr 5(1):10 (2008).
PCT/US2019/058173 International Invitation to Pay Additional Fees dated Jan. 15, 2020.
PCT/US2019/058173 International Search Report and Written Opinion dated Mar. 18, 2020.
Pearson et al. Improved tools for biological sequence comparison. PNAS USA 85(8):2444-2448 (1988).
Pei et al. PROMALS3D: a tool for multiple protein sequence and structure alignments. Nucleic Acids Res 36(7):2295-2300 (Feb. 20, 2008).
Pennings et al., Whey protein stimulates postprandial muscle protein accretion more effectively than do casein and casein hydrolysate in older men. Am J Clin Nutr 93(5):997-1005 (2011).
Sarwar et al., Digestibility of protein and amino acids in selected foods as determined by a rat balance method. Plant Foods Hum Nutr 39(1):23-32 (1989).
Savoie et al., In vitro amino acid digestibility of food proteins as measured by the digestion cell technique. Plant Foods Hum Nutr 39(1):93-107 (1989).
Takagi et al. Comparative study of in vitro digestibility of food proteins and effect of preheating on the digestion. Biological and Pharmaceutical Bulletin 26(7):969-973 (2003).
Torellis et al. Advance and Adam: two algorithms for the analysis of global similarity between homologous informational sequences. Comput. Appl. Biosci. 10:3-5 (1994).
U.S. Appl. No. 16/767,535 Office Action dated Dec. 9, 2020.
U.S. Appl. No. 16/767,535 Office Action dated Jul. 1, 2021.
U.S. Appl. No. 16/767,535 Office Action dated Mar. 11, 2021.
U.S. Appl. No. 16/767,535 Office Action dated Mar. 21, 2022.
U.S. Appl. No. 16/767,535 Office Action dated Oct. 15, 2021.
U.S. Appl. No. 16/767,535 Office Action dated Sep. 28, 2022.
U.S. Appl. No. 17/395,807 Office Action dated Jun. 6, 2022.
U.S. Appl. No. 17/395,807 Office Action dated Nov. 19, 2021.
Xu et al. How significant is a protein structure similarity with TM-score= 0.5? Bioinformatics 26:889-895 (2010).
Zhang et al., Scoring function for automated assessment of protein structure template quality. Proteins 57:702-710 (2004).
Zhang et al., TM-align: a protein structure alignment algorithm based on the TM-score. Nucleic Acids Res 33:2302-2309 (2005).

* cited by examiner

Blood glucose increases after consumption of a pea protein drink with 14 grams of added sugar, with or without the addition of protease.

Blood glucose change after consumption of a low-carb protein drink with or without the addition of protease.

Blood glucose increases after consumption of protein drink with fruits, with or without the addition of protease.

SEQUENCE LISTING

```
Sequence total quantity: 20
SEQ ID NO: 1              moltype = AA   length = 552
FEATURE                   Location/Qualifiers
source                    1..552
                          mol_type = protein
                          organism = Bacillus sp.
SEQUENCE: 1
MSDMEKPWKE EEKREVLAGH ARRQAPQAVD KGPVTGDQRI SVTVVLRRQR GDELEAHVER  60
QAALAPHARV HLEREAFAAS HGASLDDFAE IRKFAEAHGL TLDRAHVAAG TAVLSGPVDA 120
VNQAFGVELR HFDHPDGSYR SYVGDVRVPA SIAPLIEAVL GLDTRPVARP HFRLRRRAEG 180
EFEARSQSAA PTAYTPLDVA QAYQFPEGLD GQGQCIAIIE LGGGYDETSL AQYFASLGVS 240
APQVVSVSVD GATNQPTGDP NGPDGEVELD IEVAGALAPG AKIAVYFAPN TDAGFLNAIT 300
TAVHDPTHKP SIVSISWGGP EDSWAPASIA AMNRAFLDAA ALGVTVLAAA GDSGSTDGEQ 360
DGLYHVDFPA ASPYVLACGG TRLVASAGRI ERETVWNDGP DGGSTGGGVS RIFPLPSWQE 420
RANVPPSANP GAGSGRGVPD VAGNADPATG YEVVIDGETT VIGGTSAVAP LFAALVARIN 480
QKLGKPVGYL NPTLYQLPPE VFHDITEGNN DIANRARIYQ AGPGWDPCTG LGSPIGIRLL 540
QALLPSASQA QP                                                    552

SEQ ID NO: 2              moltype = DNA   length = 1659
FEATURE                   Location/Qualifiers
source                    1..1659
                          mol_type = other DNA
                          organism = synthetic construct
SEQUENCE: 2
atgagcgata tggaaaaacc gtggaaagaa gaagaaaaac gcgaagttct ggcaggtcat   60
gcacgtcgtc aggcaccgca ggcagttgat aaaggtccgg ttaccggtga tcagcgtatt  120
agcgttaccg ttgttctgcg tcgtcagcgt ggtgatgaac tggaagcaca tgttgaacgt  180
caggcagcac tggcaccgca tgcacgtgtt catctggaac gtgaagcatt tgcagcaagc  240
catggtgcaa gcctggatga ttttgcagaa attcgtaaat ttgccgaagc gcatggtctg  300
accctggatc gtgcccatgt tgcagcaggt acagcagttc tgagcggtcc ggttgatgca  360
gttaatcagg cattttgtgt tgaactgcgt cattttgatc atcctgatgg tagctatcgt  420
agctatgttg gtgatgttcg tgttccggca agcattgcac cgctgattga agcagtttta  480
ggtctggata cccgtccggt tgcacgtccg cattttcgtc tgcgtcgccg tgcagaaggt  540
gaatttgaag cacgtagcca gagcgcagca ccgaccgcat ataccgct ggatgttgca   600
caggcatatc agtttccgga aggcctggat ggtcaggtc agtgtattgc aattattgaa  660
ttaggtggtg gctatgatga aaccagcctg gcacagtatt ttgccagcct gggtgttagc  720
gctccgcagg ttgttagcgt tagcgtggat ggtgcaacca atcagccgac aggtgatccg  780
aatggtccgg atggtgaagt tgaactggat attgaagttg ccggtgcgct ggcaccgggt  840
gcaaaaattg cagtttattt tgcaccgaat accgatgccg gttttctgaa tgccattacc  900
accgcagttc atgatccgac acataaaccg agcattgtga gcattagctg gggtggtccg  960
gaagatagct gggcaccagc cagcattgca gccatgaatc gtgcattttc tggatgcagc 1020
gcactgggtg tgaccgtgct ggcagcagcc ggtgatagcg gtagcaccga tggtgaacag 1080
gatggtctgt atcatgttga ttttccggca gcgagcccgt atgttctggc atgtggtggc 1140
acccgtctgg tggcaagcgc aggtcgtatt gaacgtgaaa ccgtttggaa tgatggtcct 1200
gatggcggtt caaccggtgg tggtgttagc cgtatttttc cgctgccgag ctggcaagaa 1260
cgtgcaaatg ttccgcctag cgcaaatcct ggtgcaggta cggtcgtgg tgttccggat 1320
gttgccggta tgcagatcc ggcaaccggt tatgaagttg ttattgatgg tgaaaccacc 1380
gtgattggtg gtacaagcgc agtggcaccg ctgtttgcag ccctggttgc ccgtattaat 1440
cagaaactgg gtaaaccggt tggttatctg aatccgacac tgtatcagct gcctccggaa 1500
gtttttcatg atattaccga aggcaacaac gatattgcca atcgtgcacg tatttatcag 1560
gcaggtcctg gttgggatcc gtgtaccggt ctgggtagcc cgattggtat tcgtctgctg 1620
caggcactgc tgccgagtgc aagccaggca cagccgtga                       1659
```

```
SEQ ID NO: 3              moltype = AA   length = 515
FEATURE                   Location/Qualifiers
source                    1..515
                          mol_type = protein
                          organism = Pseudonocardia sp.
SEQUENCE: 3
MSEPVPAAAR RTIPGSERPP VDTAAAARQA VPADTRVEAT VVLRRRAELP DGPGLLTPAE    60
LAERHGADPA DVELVTRTLT GLGVEVTAVD AASRRLRVAG PAGVLAEAFG TSLAQVSTPD   120
PSGAQVTHRY RAGALSVPAE LDGVVTAVLG LDDRPQARAR FRVATAAAAS AGYTPIELGR   180
VYSFPEGSDG SGQTIAIIEL GGGFAQSELD TYFAGLGISG PTVTAVGVDG GSNVAGRDPQ   240
GADGEVLLDI EVAGALAPGA DVVVYFAPNT DAGFLDAVAQ AAHATPTPAA ISISWGGSED   300
TWTGQARTAF DAALADAAAL GVTTTVAAGD DGSTDRATDG KSHVDFPASS PHALACGGTH   360
LDANATTGAV TSEVVWNNGA GKGATGGGVS TVFAQPSWQA SAGVPDGPGG KPGRGVPDVS   420
AVADPQTGYR IRVDGQDLVI GGTSAVAPLW AALVARLVQA GRAKLGLLQP KLYAAPTAFR   480
DITEGDNGAY RAGPGWDACT GLGVPVGTAL ASALS                             515

SEQ ID NO: 4              moltype = AA   length = 531
FEATURE                   Location/Qualifiers
source                    1..531
                          mol_type = protein
                          organism = Modestobacter sp.
SEQUENCE: 4
MADDSPTTA ADRPTLPGSA RRPVAAAQAA GPLDDAAPLE VTLVLRRRTA LPAGTGRPAP     60
MGRAEFAETH GADPADAETV TAALTAEGLR ITAVDLPSRR VQVAGDVATF SRVFGVSLSR   120
VESPDPVADR LVPHRQRSGD LAVPAPLAGV VTAVLGLDDR PQARALFRPA AAVDTTFTPL   180
ELGRVYRFPS GTDGRGQRLA ILELGGGYTQ ADLDAYWTTI GLADPPTVTA VGVDGAANAP   240
EGDPNGADGE VLLDIEVAGA LAPGADLVVY FAPNTDRGFL DALSTAVHAD PTPTAVSISW   300
GQNEDEWTAQ ARTAMDEALA DAAAALGVTVC AAAGDDGSTD NAPDGQAHVD FPASSPHALA   360
CGGTTLRADP DTGEVSSETV WFHGTGQGGT GGGVSAVFAV PDWQDGVRVP GDADTGRHGR   420
GVPDVSADAD PSTGYQVRVD GTDAVFGGTS AVSPLWSALT CRLAEALGQR PGLLQPLIYA   480
GLSAGEVAAG FRDVTSGSNG AYDAGPGWDP CTGLGVPDGE ALLVRLRTAL G           531

SEQ ID NO: 5              moltype = AA   length = 528
FEATURE                   Location/Qualifiers
source                    1..528
                          mol_type = protein
                          organism = Bradyrhizobium canariense
SEQUENCE: 5
MANRKMFPNS VIAIPTSGVT AHGLIVSAAD PQSRDEKMDV SFSLGIPPAL EKELEERVDK    60
GETIPPQELT TKYAVDPTAA GTLQTWLKKE GFTITGVTPD RTTIYASAPA SQVEASLGVH   120
TVRVTREGQT YTAASDVPSL PEDIGGAVVN IGGLQPYRQA RKHLRSYIQT TPEADGEEPA   180
IANAPPYLVP EILKAYDGAR LGLTGKGQEI AILIDTVPLD TDLTSFWTAN GVAGSLARIT   240
KINVKGGALP TPSGEETLDA EWASTIAPDA NVRIYASGTL SFIDLDRALD RIYADALAQP   300
KLRIVSISLG LSEAYMAKGE VDAEEARFVR FAALGVNVFV STGDAGSNPG PDGHHANGPL   360
AAEWMSTSPH VVAVGGTSLR LANNGQVASE TGWTGSGGGK SNFQPRPAWQ QGHGVPAGNQ   420
RMVPDVGAAA DPNEGALVIL NGQRLQYGGT SWSAPIWAGL CALINEARQN NHKTPLPYLN   480
SLIYPMIGSN CFRDELTGSN GAYSCGPGYD LVTGIGSPDL KQLAAKLA                528

SEQ ID NO: 6              moltype = AA   length = 512
FEATURE                   Location/Qualifiers
source                    1..512
                          mol_type = protein
                          organism = Arthrobacter woluwensis
SEQUENCE: 6
MAGVNEPYNA REDGIPLKSS ARAVVPGVKL HGPTDGASRL EITVVLRRRT ELPSAAADGH    60
LTAAELASEY GASDDDVRLA TEVFTRLGAD VVESDPASRR LRLSGTVEQL SSIFGTTLED   120
ATSTAPDGAT VHYRHRLGEL RIPAELNGIV IAVLGLDDRP QARAHFRMLP RTTAGTSYSP   180
VELGRVYGFP DGTDGSGQTV AIIELGGGYA QADLDAYFAG LGLATPQITS IGVDGGANQG   240
GNDPQGADGE VLLDIEVVGA LAPKAAIQVY FAPNTDAGFL DAVVAATKAA PCAISISWGQ   300
SEDQWTAQAR DAFDQALADA AALGITTTVA AGDRGSSDGA ADGKAHVDFP ASSPHALACG   360
GTRLEADPAT GAIRSETVWN EGPDSATGGG YSKVFPRPSW QSPSAGKSGR GVPDVSAVAD   420
PQTGYRIRVD GKDMVIGGTS AVAPLWAALI ARFAQAGNRR FGLIQPSLYA VSSGFRDVTV   480
GDNGSYHAGP GWDACTGLGT PDGAALLAAL KG                                 512

SEQ ID NO: 7              moltype = AA   length = 549
FEATURE                   Location/Qualifiers
source                    1..549
                          mol_type = protein
                          organism = Terriglobus roseus
SEQUENCE: 7
MSTRAARTTP SALADLRNEP RSPLPGSEKA ALADTPATTA AGIKPLRATA VAKAKPASSR    60
KKITVSVVVP RTKPVTQAAV AGKHLTRAQF KSSHAAAPAS VKAVQKFAKA FNLVSKAEPA   120
RSTVHLTGTV KDMQDAFGVT LQEHTVGAKT LRIRQGAIYL PDSVLPHVQA VLGLDNRPQA   180
KPHYRVGKAR AAASTSFTPP QLAQLYGFPT SAKATGQTIA LIELGGGFRQ ADITAYFKSL   240
GIAAPSVKAV LVDGGKNAPS NANGADGEVM LDIEVAAAVA PGANIAVYFA PNTDQGFVDA   300
IATAAHDTTN KPTIISISWG GPESSWTSQA LTALDNACKD AAALGITVTA AAGDDGSDDG   360
VGDGKKHVDF PASSPNVLAC GGTKLVASNG AITSEVVWNE TANKEGATGG GISTAFFQPT   420
WQKSIAATKS GRGVPDVAGD ADPTTGYQVR VDGQNMVIGG TSAVAPLWAG LIALSNATNK   480
```

```
NAAGLPQAKL YSTTGQKAFR DITSGNNGAF KAAKGWDPCT GLGSPKAASI ITLLATKSSA    540
KKKTSRAKA                                                            549

SEQ ID NO: 8             moltype = AA  length = 539
FEATURE                  Location/Qualifiers
source                   1..539
                         mol_type = protein
                         note = Caballeronia jiangsuensis
                         organism = unidentified
SEQUENCE: 8
MESIMPSQPS SIPVRGSERA ALPTAHVVGP AASDERLEVT LRVRPRAQLH ASASEAQSLR    60
PPGERSYLSR EQLASAHGAA PEDIAKVEAF AQSHGLQVVL TSAARRCVIV SGTVAALESA   120
FAVKLQQYRF DGGSYRGRVG PVFVSPEIGD IVEGVFGLDD RPQAIAHFKR SAHAVRAEDG   180
AAPHAGGASF TPPQLAKLYN YPGDTDGTGQ CIGIVEFGGA IRAADIRAYF KELGLPAPHV   240
NTVLVDHAHM RSDDADAEVM LDIEVAAAIA PKAQIVVYFA PNTSQGFIDA FTHAIHDTVH   300
KPSVISVSWG GPEKDWSAQI KTQLDQVFQD AAALGVTICA ASGDAGSSDE NPDALASIGL   360
TPDGLSHADF PASSPFALAC GGTKLVASAS AITSETVWNE DPVRSATGGG ISDFFDVPGY   420
QATANIPVSA NPGGRKGRGV PDIAADADPA TGYLVRVHGQ DAVIGGTSAV APLMAGLVAL   480
LNHKLGHPVG FLNPLLYRTA GITRDITQGN NGAYAAGKGW DACTGLGVPD GAKLLDALM    539

SEQ ID NO: 9             moltype = AA  length = 537
FEATURE                  Location/Qualifiers
source                   1..537
                         mol_type = protein
                         note = Hymenobacter psoromatis
                         organism = unidentified
SEQUENCE: 9
MPQSQNRVVV RGSERQPMPK AHSQHALPPT ERLEVTVRLR PKAALASAAA SSHAMADVPP    60
SQRTYLSREE LAAQCGASED DAQAVADFAH AHGLVVIHTD LARRSVLLAG TAADFGAAFG   120
TQLHQYSSPE GTYRGRTGTV TVPAPLADIV QGVFGLDDRR QAEPHFQVRP GPTPAPGAIV   180
ARAAGQSFTP PQLAQLYDFP GGLDGTGQTI AVIELGGGFK PADLKAYFTG LNLPVPTVKV   240
VSVNGGRNQP TNANSADGEV LLDIEVAAAV APRAHLVVYF APNTSQGFLN AITTAVHDKV   300
NNPGIISISW GGPESTWTGQ AMDQFDQAFQ EAAMLGVTVC VAAGDNGSAD GVADGQPHAD   360
FPASSPFALA CGGTKLTASG PTISSEVVWN EGPNSATGGG LSAHFPVPAY QQQLKFPTPP   420
AGAKAGRGLP DVAGDADPNT GYQVRVDGQN LVIGGTSAVA PLWAGLLALL NQKLPKPVGF   480
LNPLLYGSLA GQGVTRDITS GNNGAFAAGP GWDACTGWGS PVGGKLLAAL QGGAAVA     537

SEQ ID NO: 10            moltype = AA  length = 524
FEATURE                  Location/Qualifiers
source                   1..524
                         mol_type = protein
                         note = Caballeronia humi
                         organism = unidentified
SEQUENCE: 10
MSKHPLMGSE RAPFDGAQSV GKADPAERLE VTVLVRRGSS DALRTRVSKL VAGNASDGHI    60
QREDFAQQFG AAPNDMSAVR NFASQHGLSV VEEHAARRTV ILSGTVAQFN DAFDVDLQQF   120
EHAGGSYRGR TGPVHLPDEL SGVVDAVLGL DNRPQARPHF RSRPPQGNVH VWQSSRTGTTS   180
STPLQLASLY DFPAGTGQGQ CIAIIELGGG YRPADLKAYF SKLGIASPKV TTVSVDHGKN   240
HPTGDANGPD GEVMLDIEIA GAIAPGAHIA VYFAPNTDAG FLDAVTTAIH DTIRKPSVIS   300
ISWGGPESAW TEQAMTAFDQ AFQAAAALGI TVCVASGDNG SGDGVNDGAD HVDFPASSPY   360
ALACGGTSVQ AGKGAIAKET VWNDGANGGA SGGGVSSFFA LPAWQEGLQA ARAKGGTSVQ   420
QMRGVPDVAG NADPATGYDV RVDGSDMVIG GTSAVAPLWA GLVARINGAK NSPAGYLNPK   480
LYKTAAGLTD ITQGNNGDFV ASAGWDACTG LGRPDGNKLA GTFG                    524

SEQ ID NO: 11            moltype = AA  length = 547
FEATURE                  Location/Qualifiers
source                   1..547
                         mol_type = protein
                         organism = Alicyclobacillus ferrooxydans
SEQUENCE: 11
MDETNFTSTN GSPQYIPVTG SARAIVPGAT HAGHTDDNEV LSVTLQLRRP SADELTAHVE    60
ALGTTPPANR KHMTHDEFEA SHGASDDDLN LVTAFATEQG LSVERINKAA ATVHVSGTAG   120
AFNKAPHVQL GNYQHPDFTY RGYDGPVHIP AHLTDIVTGV LGLDNRPQAH PHFRVYQEAA   180
VRSNALAAPI SYTPTQVAAL YNFPTNVDCS GQCIGIIELG GGYSKSNLDQ YFASLGVPTP   240
TITSVSVDGG QNQPTGSPNG PDGEVDLDIE VAASVAPGAH IAVYFAPNTD AGFLDAITTA   300
VHDKTNKPSV ISISWGGPEM SWTTQAMQAM NNAMQSAAAL GVTITVAAGD NGSTDGVNDG   360
SFHVDFPASA PYALACGGTH LVGSGSTIES ETVWNDGANG GATGGGVSSV FPVPSWQQKA   420
NVPPSANPGA GTGRGVPDVS GDADPATGYQ VLVDGQQFPI GGTSAVAPLW AGLVALANQT   480
LGKPVGYINP LLYSIPAQDN AFHDITQGNN DPNQTGQVYP AGPGWDACTG LGSPNGTLLI   540
QALGQIG                                                              547

SEQ ID NO: 12            moltype = DNA  length = 1572
FEATURE                  Location/Qualifiers
source                   1..1572
                         mol_type = other DNA
                         organism = synthetic construct
SEQUENCE: 12
atgagcgaac ctgttccggc agcagcacgt cgtaccattc cgggtagcga acgtccgcct    60
gttgataccg cagcagcagc ccgtcaggca gttcctgcag ataccegtgt tgaagcaacc   120
```

```
gttgttctgc gtcgtcgtgc agaactgccg gatggtccgg gtctgctgac accggcagaa    180
ctggcagaac gtcatggtgc agatccggca gatgttgaac tggttacccg tacactgacc    240
ggtctgggtg ttgaagttac cgcagttgat gcagcaagcc gtcgtctgcg tgttgccggt    300
ccggcaggca ttctggcaga agcatttggc accagcctgg cacaggttag cacaccggat    360
ccgagcggtg cccaggttac ccatcgttat cgtgccggtg cactgagcgt tccagccgaa    420
ctggatggtg ttgtgaccgc agttctgggt ttagatgatc gtccgcaggc acgtgcgcgt    480
tttcgtgttg caacggcagc cgcagcaagc gcaggttata ccccgattga actgggtcgt    540
gtttatagct ttccggaagg tagtgatggt agcggtcaga ccattgcaat tattgaatta    600
ggtggtggtt ttgcacagag tgaactggat acctattttg caggtctggg tattagcggt    660
ccgaccgtta cagcagttgg tgttgatggt ggtagcaatg ttgcaggtcg tgatccgcag    720
ggtgcagatg tgaagttct gctggatatt gaagttgcgg gtgcactggc accgggtgcc    780
gatgttgttg tttattttgc accgaatacc gatgcaggtt ttctggatgc agttgcacag    840
gcagcacatg caacccgac tccggcagcc attagcatta gctggggtgg tagcgaagat    900
acctggacag gtcaggcacg taccgccttt gatgcggcac tggcagatgc agccgcactg    960
ggtgttacca ccaccgttgc agccggtgat gatggtagta ccgatcgtgc aaccgatggt    1020
aaaagccatg ttgattttcc ggcaagcagt ccgcatgcac tggcctgtgg tggcacccat    1080
ctggatgcca atgcaaccac cggtgcagtt accagcgaag ttgtttggaa taatggtgca    1140
ggtaaaggtg caaccggtgg cggtgttagc accgttttg cccagccgaa ctggcaggca    1200
agtgccggtg ttccggatgg ccctggtggt aaacctggtc gtggtgtgcc ggatgttagc    1260
gcagttgccg atccgcagac cggttatcgt attcgtgtgg atggtcagga tctggttatt    1320
ggtggtacaa gcgcagtggc accgctgtgg gcagcactgg ttgcacgtct ggttcaggca    1380
gtcgcgcaa aactgggcct gctgcagccg aaactgtatg cagcaccgac gcgcatttcgt    1440
gatattaccg aaggtgataa tggcgcatat cgtgcaggtc ctggttggga tgcatgtaca    1500
ggcctgggcg ttccggttgg caccgcactg cgagcgcac tgagtctcga gcaccaccac    1560
caccaccact ga                                                       1572

SEQ ID NO: 13         moltype = DNA  length = 1620
FEATURE               Location/Qualifiers
source                1..1620
                      mol_type = other DNA
                      organism = synthetic construct
SEQUENCE: 13
atggccgatg atagcagccc gaccaccgca gcagatcgtc cgacactgcc tggtagcgca    60
cgtcgtccgg ttgcagcagc acaggcagca ggtccgctgg atgatgcagc accgctggaa    120
gttaccctgg ttctgcgtcg tcgtaccgca ctgccagcag gcacaggtcg tccggcaccg    180
atgggtcgtg cagaatttgc agaaacccat ggtgcagatc cggcagatcg cgaaaccgtt    240
accgcagcac tgaccgcaga aggtctgcgt attaccgcag ttgatctgcc gagccgtcgt    300
gttcaggttg ccggtgatgt tgcaacctt agccgtgttt ttggtgttag cctgagccgt    360
gttgaaagcc ctgatccggt tgccgatcgt ctggttccgc atcgtcagcg tagcggtgca    420
ctggcagttc ctgctccgct ggcaggcgtt gtgaccgcag ttctgggttt agatgatcgt    480
ccgcaggcac gtgcactgtt tcgtcctgca gcagccgttg ataccaccct tactccgctg    540
gaactgggtc gtgtttatcg ttttccgagc ggtacagatg gtcgtggtca gcgtctggca    600
attctggaat taggtggtgg ttataccag gcagatccgg atgcatattg gaccaccatt    660
ggtctggcag atccgcctac cgttacagca gttggtgttg atggtgcagc aaatgcaccg    720
gaaggtgatc cgaatggtgc cgatggtgaa gttctgctgg atattgaagt tgcgggtgca    780
ctggcaccgg gtgccgatct ggttgtttat tttgcaccga taccgatcg tggttttctg    840
gatgccctga gcaaccgcagt gcatgccgat ccgacaccga gcagtgag cattagctgg    900
ggtcagaatg aagatgaatg gaccgcacag gcacgtaccg caatggatga agcactggca    960
gatgcagccg cactgggtgt taccgttttgt gcagcagcgg gtgatgatgg tagcacagat    1020
aacgcaccg atggtcaggc acatgttgat tttccggcaa gcagtccgca tgcgctggca    1080
tgtggtggta caacctggcg tgcggatccg gataccgtg aagttagcag cgaaaccgtt    1140
tggtttcatg gcaccggtca aggtggtact ggtggtggtg tgagcgcagt ttttgcagtt    1200
ccggattggc aggatggtgt tcgtgttccg ggtgatgcag ataccggtcg tcatggtcgc    1260
ggtgttccgg atgttagcgc agatgctgat ccgagtaccg ttatcaggt tcgtgtggat    1320
ggtacggatg cagtgtttgg tggcaccagc gcagttagtc cgctgtgtgc tgcactgacc    1380
tgtcgtctgt ccgaagcgct gggacagcgt ccgggtctgc tgcagccgct gatttatgca    1440
ggtctgagcg caggcaagt tgcagccggt tttcgtgatg ttaccagcgg tagcaatggt    1500
gcatacgatg caggtcctgg ttgggatccg tgcaccggtc tgggtgtgcc ggatggcgaa    1560
gcactgctgg ttcgtctgcg tacagcactg ggcctcgagc accaccacca ccaccactga    1620

SEQ ID NO: 14         moltype = DNA  length = 1584
FEATURE               Location/Qualifiers
source                1..1584
                      mol_type = other DNA
                      organism = synthetic construct
SEQUENCE: 14
atggccaacc gtaaaatgtt tccgaatagc gttattgcaa ttccgaccag cggtgttacc    60
gcacatggtc tgattgttag cgcagcagat ccgcagagcg tgatgaaaa aatggatgtt    120
agctttagcc tgggtattcc gcctgcactg gaaaaagaaa tggaagaacg tgttgataaa    180
ggcgaaacca ttccgcctca agaactgacc accaaatatg cagttgatcc gaccggcagca    240
ggcaccctgc agacctggct gaaaaaagaa ggttttacca ttaccggtgt gactccggat    300
cgtaccacca tttatgcaag cgcaccggca agccaggttg aagcaagcct gggtgttcat    360
accgttcgtg ttacccgtga aggccagacc tataccgcag caagtgatgt tccgagcctg    420
ccggaagata ttggtggtgc cgttgttaat attggcgtgt cagccaggca    480
cgtaaacatc tgcgtagcta tattcagacc acaccggaag cagatggtga agaaccggca    540
attgcaaatg caccgcctta tctggttccg gaaattctga agcatatga tggtgcacgt    600
ctgggtctga ccggtaaagg tcaagaaatt gccattctga ttgataccgt tccgctggat    660
accgatctga ccagcttttg gaccgcaaat ggtgttgcag gtagcctggc acgtattacc    720
aaaatcaatg ttaaggtgg tgcactgccg acaccgagcg gtgaagaaac cctggatgca    780
```

```
gaatgggcaa gcaccattgc accggatgca aatgttcgta tttatgccag cggtacactg  840
agctttattg atctggatcg tgcactggat cgcatttatg ccgatgcact ggcacagccg  900
aaactgcgta ttgtgagcat tagtctgggc ctgagcgaag catatatggc aaaaggtgaa  960
gttgatgcag aagaagcacg ttttgttcgt tttgcagcac tgggtgttaa tgttttgtt  1020
agcaccggtg atgccggtag caatccgggt cctgatgatc atcatgcaaa tggtccgctg  1080
gcagcagaat ggatgagcac cagtccgcat gttgttgcac ttggtggcac cagcctgcgt  1140
ctggcaaata atggtcaggt tgcaagcgaa accggttgga ccggtagcgg tggtggtaaa  1200
agcaattttc agcctcgtcc ggcatggcag caaggtcatg tgttccagc aggtaatcag  1260
cgtatggtgc cggatgttgg tgcagcagcc gatccgaatg aaggtgcact ggttattctg  1320
aatggtcagc gtctgcagta tggcggtaca agttggagcg caccgatttg ggcaggtctg  1380
tgtgcactga ttaatgaagc acgtcagaac aatcataaaa ctccgctgcc gtatctgaac  1440
agcctgattt atccgatgat tggtagcaac tgttttcgtg atgaactgac cggttcaaat  1500
ggtgcatata gctgtggtcc gggttatgat ctggttaccg gtattggtag tccggatctg  1560
aaacagctgg cagccaaact ggca                                         1584

SEQ ID NO: 15        moltype = DNA  length = 1536
FEATURE              Location/Qualifiers
source               1..1536
                     mol_type = other DNA
                     organism = synthetic construct
SEQUENCE: 15
atggcaggcg ttaatgaacc gtataatgca cgtgaagatg gtattccgct gaaaagcagc  60
gcacgtgcag ttgttccggg tgttaaactg catggtccga ccgatggtgc aagccgtctg  120
gaaattaccg ttgttctgcg tcgtcgtacc gaactgccga gcgcagcagc agatggtcat  180
ctgaccgcag cagaactggc aagcgaatat ggtgcatcag atgatgatgt tcgtctggca  240
accgaagttt ttacccgtct gggtgcagat gttgttgaaa gcgatccggc aagtcgtctg  300
ctgcgtctga gcggcaccgt tgaacagctg agcagcattt ttggtacaac cctggaagat  360
gcaaccagca ccgcaccgga tggtgccacc gttcattatc gtcatcgtct gggcgaactg  420
cgtattccgg cagaactgaa tggtattgtt attgcagttc tgggcttaga tgatcgtccg  480
caggcacgcg cacattttcg tatgctgcct cgtaccaccg caggtacaag ctatagtccg  540
gttgaactgg gtcgtgttta tggttttccg gatggcaccg atggtagcgg tcagaccgtt  600
gcaattattg aattaggtgg tggttatgca caggcagatc tggatgcata ttttgcaggt  660
ttaggtctgc cacaccgca gattaccagc attggtgttg atggtggtgc aaatcaaggt  720
ggtaatgatc cgcagggtgc cgatggtgaa gtgctgctgg atattgaagt tgttggtgca  780
ctggcaccga aagcagcaat tcaggtttat tttgcaccga ataccgatgc aggttttctg  840
gatgccgttg ttgcagcaac caaagcagca ccgtgtgcca ttagcattag ctggggtcag  900
agcgaagatc agtggaccgc acaggcacgt gatgcatttg atcaggcact ggcagatgca  960
gcagccctgg gtattaccac caccgttgca gccggtgatc gtggtagcag tgatggtgcc  1020
gcagatggta aagcacatgt tgattttccg gcaagcgctc cgcatgcact ggcctgtgtt  1080
ggtacacgtc tggaagcaga tcctgcaacc ggtgcaattc gtagcgaaac cgtttgaat  1140
gaaggtccgg atagcgcgac cggtggtggc tatagcaaag ttttccgcg tccgagctgg  1200
cagagcccga gtgcaggtaa aagcggtcgt ggtgtgccgg atgttagcgc agttgcagat  1260
ccgcagacag gttatcgtat tcgtgtggat ggcaaagata tggttattgg tggcacctca  1320
gcagttgcac cgctgtgggc agcactgatt gcacgttttg cccaggcagg taatcgtcgt  1380
tttggtctga ttcagccgag cctgtatgca gttagcagcg gttttcgtga tgttaccgtt  1440
ggtgataatg gtagctatca tgcaggtcct ggttgggatg catgtaccgg tctgggcacc  1500
cctgatggtc agcccctgct ggcagccctg aaaggt                            1536

SEQ ID NO: 16        moltype = DNA  length = 1647
FEATURE              Location/Qualifiers
source               1..1647
                     mol_type = other DNA
                     organism = synthetic construct
SEQUENCE: 16
atgagcaccc gtgcagcacg taccacaccg agcgcactgg ccgatctgcg taatgaaccg  60
cgtagtccgc tgcctggtag cgaaaaagca gcactggcag atacaccggc aaccaccgca  120
gcaggtatca aaccgctgcg tgcaaccgca gttgcaaaag caaaccggc aagcagccgc  180
aaaaaaatca ccgttagcgt tgttgttccg cgtaccaaac cggttacaca ggcagcagtt  240
gcaggtaaac atctgacccg tgcacagttt aaaaagcaca atgcagcagc accggcaagt  300
gttaaagcag ttcagaaatt tgccaaagcc tttaacctgg ttagcaaagc cgaaccggca  360
cgtagcaccg ttcatctgac cggcaccgtt aaagatatgg aggatgcatt tggtgttacc  420
ctgcaagaac ataccgttgg tgcaaaaaccc ctgcgtattc gtcagggtgc aatttatctg  480
ccggatagcg ttctgccgca tgttcaggca gttctgggtt tagataatcg tccgcaggca  540
aaaccgcatt atcgtgttgg taaagcacgt gcagcagcca gcaccagctt taccccctccg  600
cagctggcac agctgtatgg ttttccgacc agcgcaaaag ccaccggtca gaccattgca  660
ctgattgaat taggtggtgg ttttcgtcag gcagatatta ccgcatattt caaaagcctg  720
ggtattgcag caccgagcgt taagccgttc tggttgatgt ggtaaaaa tgcaccgagc  780
aatcaaaatg gtgcagatgg tgaagttatg ctggatattg aagttgcagc ggcagttgca  840
ggtgcca atattgcagt ttattttgca ccgaataccg atcaggggttt tgttgatgca  900
attgcgaccg cagcacatga taccaccaat aaaccgacca ttattagcat tagctggggt  960
ggtccggaaa gcagctggac cagccaggca ctgaccgcac tggataatgc atgtaaagat  1020
gcagccgcac tggtattac cgttacagca gcagccggtg atgatggttc agatgatggt  1080
gttggtgatg gtaaaaaaca tgttgatttt ccggcaagct caccgaatgt tctggcatgt  1140
ggtggcacca aacttggttgc aagcaatggt gcaattaccga gcgaagttgt tggaatgaa  1200
accgccaata aagaaggtgc aacaggcgga ggtattagca ccgcatttcc gcagccgacc  1260
tggcagaaaa gcattgcagc aacccaaaagc ggtcgtggtg ttccggatgt tgcgggtgat  1320
gcagatccga ccaccggtta tcaggttcgt gttgatggtc agaatatggt tatcggtggt  1380
acaagcgcag ttgctccgct gtgggcaggt ctgattgccc tgagcaatgc caccaacaaa  1440
aatgcagcag gtctgccgca ggccaaactg tatagcacca caggtcagaa agcatttcgt  1500
```

```
gatattacca gtggcaataa cggtgcgttt aaagcagcaa aaggttggga tccgtgtacc    1560
ggtctgggta gcccgaaagc cgcaagcatt attaccctgc tggccaccaa aagcagcgcc    1620
aaaaagaaaa ccagccgtgc aaaagcc                                        1647

SEQ ID NO: 17           moltype = DNA   length = 1617
FEATURE                 Location/Qualifiers
source                  1..1617
                        mol_type = other DNA
                        organism = synthetic construct
SEQUENCE: 17
atggaaagca ttatgccgag ccagccgagc agcattccgg ttcgtggtag cgaacgtgca     60
gcactgccga ccgcacatgt tgttggtccg gcagcaagtg atgaacgtct ggaagttacc    120
ctgcgtgttc gtccgcgtgc acagctgcat gcaagcgcaa gcgaagcaca gagcctgcgt    180
ccgcctggtg aacgtagcta tctgagccgt gaacagctga caagcgcaca tggtgcagca    240
ccggaagata ttgcaaaagt tgaagcattt gcccagagcc atggtctgca ggttgttctg    300
accagcgcag cacgtcgttg tgttattgtt agcggcaccg ttgcagccct ggaaagcgca    360
tttgccgtta aactgcagca gtatcgtttt gatggtggta gctatcgtgg tcgtgttggt    420
cctgtttttg ttagtccgga aattggtgat attgtggaag tgttttttgg tctggatgat    480
cgtccgcagg caattgcaca tttttaaacgt agtgcacatg cagttcgtgc cgaagatggt    540
gccgctccgc atgccggtgg tgcaagcttt accccctccgc agctggccaa actgtataac    600
tatccggggt ataccgatgg caccggtcag tgtattggta ttgttgaatt tggtggtgcc    660
attcgtgcag cagatattcg tgcatatttc aaagaactgg cgtgcctgc accgcatgtt    720
aataccgttc tggttgatca tgcacatatg cgtagtgatg atgcagatgc agaagttatg    780
ctggatattg aagttgcagc agccattgca ccgaaagcac agattgttgt ttattttgct    840
ccgaatacca gccagggttt tattgatgca ttttacccatg caattcatga caccgttcat    900
aaaccgagcg ttattagcgt tagctgggt ggtccggaaa agatttggag gcacagatt    960
aaacccagc tggatcaggt ttttcaggat gcagcagcac tgggtgttac catttgtgca   1020
gccagcggtg atgcaggtag cagtgatgaa atccggatg cactggcaag cattggtctg   1080
acaccggatg gtctgagcca tgcagatttt ccggcaagca gcccgtttgc actggcctgt   1140
ggtggcacca aactggttgc cagcgccagc gcaattacca gcgaaaccgt ttggaatgaa   1200
gatccggtgc gtagcgcaac cggtggtggt attagcgatt tttttgatgt tccgggttat   1260
caggcaaccg caaatattcc ggttagcgca atcctggtg tcgtaaagg tcgtggtgtt   1320
ccggatattg cagccgatgc agatccggca accggttatc tggttcgtgt tcatggtcag   1380
gatgccgtta ttggtggtac aagcgcagtt gcaccgctga tggcaggtct ggttgcactg   1440
ctgaatcata aactgggtca tccggttggt tttctgaatc cgctgctgta tcgtaccgca   1500
ggtattaccc gtgatattac ccagggcaat aatggtgca atgccgcagg taaaggttgg   1560
gatgcatgta ccggtctggg tgtgccggat ggtgccaaac tgctggatgc cctgatg      1617

SEQ ID NO: 18           moltype = DNA   length = 1611
FEATURE                 Location/Qualifiers
source                  1..1611
                        mol_type = other DNA
                        organism = synthetic construct
SEQUENCE: 18
atgccgcaga gccagaatcg tgttgttgtt cgtggtagcg aacgtcagcc gatgccgaaa     60
gcacatagcc agcatgcact gcctccgacc gaacgtgcag aagttaccgt tcgtctgcgt    120
ccgaaagcag cactggcaag cgcagcagca agcagccatg caatggcaga tgttccgcct    180
agccagcgta cctatctgag ccgtgaagaa ctggcagcac agtgtggtgc aagcgaagat    240
gatgcacagg cagttgcaga ttttgcacat gcacatggtc tggttgttat tcataccgat    300
ctggcacgtc gtagcgttct gctggcaggc accgcagccc attttggtgc agcatttggc    360
acccagctgc atcagtatag cagtccggaa ggcacctatc gtggtcgtac cggcaccgtg    420
accgttccgg caccgctggc agatattgtt cagggtgttt ttggtctgga tgatcgtcgt    480
caggcagaac cgcattttca ggttcgtccg gcctcggacac cggctccggg tgcaattgta    540
gcacgtgcag ccggtcagag ctttacccct ccgcagctgg cacagctgta tgattttcca    600
ggtggcctgg atggcaccgg tcagaccatt gcagttattg aattaggtgg tggttttaaa    660
ccggcagatc tgaaagcata tttttaccgt ctgaacctgc cggtgccgac cgttaaagtt    720
gttagcgtta atggtggtcg taatcagccg accaatgcaa atagcgcaga tggtgaagtg    780
ctgctggata ttgaagttgc agcagcagtt gcaccgcgtg cacatctggt ggtttatttt    840
gcaccgaata ccagccaggg ttttctgaat gcaattacca ccgcagttca tgataaagtg    900
aataatccgg gtattatcag cattagctgg ggtggtccgg aaagtacctg gaccggtcag    960
gcaatggatc agtttgatca ggcatttcaa gaggcagcag tgctgggtgt taccgtttgt   1020
gttgcagcgg gtgataatgg tagtgccgat ggtgttgcaa atggtcagcc tcatgccgat   1080
tttccggcaa gcagtccgtt tgcactggca tgtggtggca ccaaactgac cgcaagcggt   1140
ccgaccatta gtagcgaagt tgttggaat gaaggtccga atagcgcaac cggtggtggt   1200
ctgagcgcac attttccggt tccggcatat cagcagcagc tgaaatttcc gacacctccg   1260
gcagcgcaa aagcaggtcg tggtctgccg gatgttgaag gtgatgcaga tccgaatacc   1320
ggttatcagg tgcgtgttga tggtcagaat ctggttattg gtgataaag cgcagttgct   1380
ccgctgtggg caggtctgct ggccctgctg aatcagaaac tgccgaaacc ggttggcttt   1440
ctgaatccgc tgctgtatgg tagcctggca gtcagggtg tgaccccgtga tattaacctct   1500
ggtaataatg gtgcatttgc agcaggtcct ggttgggat catgtaccgg ttggggtagt   1560
ccggttggtg gtaaactgtt agcagccctg caaggtggtg cagccgttgc a             1611

SEQ ID NO: 19           moltype = DNA   length = 1572
FEATURE                 Location/Qualifiers
source                  1..1572
                        mol_type = other DNA
                        organism = synthetic construct
```

```
SEQUENCE: 19
atgagcaaac atccgctgat gggtagcgaa cgtgcaccgt ttgatggtgc acagagcgtt    60
ggtaaagcag atccggcaga acgtctggaa gttaccgttc tggttcgtcg tggtagcagt   120
gatgccctgc gtacccgtgt tagcaaactg gttgcaggta atgcaagtga tggtcatatt   180
cagcgtgaag attttgcaca gcagtttggt gcagcaccga atgatatgag cgcagttcgt   240
aattttgcaa gccagcatgg tctgagcgtt gttgaagaac atgcagcacg tcgtaccgtt   300
attctgagcg gcaccgttgc acagtttaat gatgcatttg atgttgatct gcagcagttc   360
gaacatgccg gtggtagcta tcgtggtcgt accggtccgg ttcatctgcc tgatgaactg   420
agcggtgttt tgatgcagt tctgggttta gataatcgtc cgcaggcacg tccgcatttt   480
cgtagccgtc cgcctcaggg taatgttcat tggcagagca ccgcaccgg tacaaccagc   540
agcacaccgc tgcagctggc aagcctgtat gattttccgg caggcaccgg tcagggtcag   600
tgtattgcaa ttattgaatt aggtggtggt tatcgtccgg cagatctgaa agcatatttt   660
agtaaactgg gtattgcgag cccgaaagtt accaccgtta gcgttgatca tggtaaaaat   720
catccgaccg gtgatgcaaa tggtccggat ggtgaagtta tgctggatat tgaaattgcc   780
ggtgcaattg cccctggtgc acatattgca gtttattttg caccgaatac cgatgcaggt   840
tttctggatg cagtgaccac cgcaattcat gataccattc gtaaaccgag cgttattagc   900
attagctggg gtggtccgga aagcgcatgg accgaacagg caatgaccgc atttgatcag   960
gcatttcagg cagcagcagc cctgggtatt accgtttgtg ttgcaagcgg tgataatggt  1020
agtggtgatg tgttaatga tggtgccgat catgttgatt ttccagcaag cagcccgtat  1080
gcactggcat gtggtggcac cagcgttcag gcaggtaaag gtgccattgc aaaagaaacc  1140
gtttggaatg atggcgcaaa tggtggtgcc agcggtggtg tgttagcag ctttttttgca  1200
ctgcctgcat ggcaagaagg tctgcaggca gcacgtgcaa aaggtggtac aggtgcactg  1260
cagatgcgtg tgttccgga tgtggcaggc aatgccgatc cggcaaccgg ttatgatgtt  1320
cgtgttgatg gtagcgatat ggttattggt ggtacaagcg cagttgcacc gctgtgggca  1380
ggtctggttg cacgtattaa tgcaggtaaa aatagtccgg caggttatct gaatccgaaa  1440
ctgtataaaa ccgcagcagg tctgaccgat atcacccagg gtaataatgg tgattttgtt  1500
gccagcgcag gttgggatgc atgtaccggt ctgggtcgtc ctgatggtaa taaactggca  1560
ggtacatttg gt                                                      1572

SEQ ID NO: 20    moltype = DNA  length = 1641
FEATURE          Location/Qualifiers
source           1..1641
                 mol_type = other DNA
                 organism = synthetic construct
SEQUENCE: 20
atggacgaaa ccaattttac cagcaccaat ggtagtccgc agtatattcc ggttaccggt    60
agcgcacgtg caattgttcc gggtgcaacc catgcaggtc ataccgatga taatgaagtt   120
ctgagcgtta ccctgcagct gcgtcgtccg agcgcagatg aactgaccgc acatgttgaa   180
gcactgggta caaccctcc ggcaaatcgt aaacatatga cccatgatga atttgaagca   240
agccatggtg caagtgatga tgatctgaat ctggttaccg catttgcaac cgaacagggt   300
ctgagcgtgg aacgtattaa caaagcagca gcaccgttc atgttagcgg tacagccggt   360
gcattcaata aagcatttca tgttcagctg ggcaattatc agcatccgga ttttacctat   420
cgtggttatg atggtccggt tcatattccg gcacatctga ccgatattgt taccggtgtt   480
ctgggtttag ataatcgtcc gcaggcaaaa ccgcattttc gtgtttatca agaagcagca   540
gttcgtagca atgcactggc agcaccgatt agctataccc cgacacaggt tgcagcactg   600
tataacttttc cgaccaatgt tgattgtagc ggtcagtgta ttggcattat tgaattaggt   660
ggtggctaca gcaaaagcaa tctggatcag tattttgcaa gctgggtgt tccgacaccg   720
accattacca gcgttagcgt tgatggtggt cagaatcagc cgaccggtag tccgaatggt   780
ccggatggtg aagttgatct ggatattgaa gttgcagcaa gcgttgcacc gggtgcacat   840
attgcagttt attttgcacc gaataccgat gcaggttttc tggatgcaat taccaccgca   900
gttcatgaca aaaccaataa accgagcgtt attagcatta gctggggtgg tccggaaatg   960
agctggacca cacaggcaat gcaggccatg aataatgcaa tgcagagcgc agccgcactg  1020
ggtgttacca ttaccgttgc agccggtaat ggtagcacc gatggtgt taatggtggt  1080
agctttcatg ttgattttcc ggcaagcgca ccgtatgcgc tggcatggca tggcacccat  1140
ctggttggta gcggtagcac cattgaaagc gaaaccgttt ggaatgatgg tgcaaatggt  1200
ggtgcgaccg gtggtggtgt tagcagcgtt tttccggttc cgagctggca gcagaaagca  1260
aatgttccgc ctagcgcaaa tcctggtgca ggcaccggtc gtggcgttcc ggatgtgagc  1320
ggtgatgcag atccggcaac cggttatcag gttctggttg atggtcagca gtttccgatt  1380
ggtggtacaa gcgcagttgc accgctgtgg gcaggtctgg ttgcactggc caatcagacg  1440
ctgggtaaac cggttggtta tatcaatccg ctgctgtata gcattcctgc acaggataat  1500
gcctttcatg atattcccca gggcaataat gatccgaatc agaccggtca ggtttatccg  1560
gcaggtccag gttgggatgc atgtaccggt ctgggttcac cgaatggcac cctgctgatt  1620
caggcactgg gtcagattgg t                                            1641
```

BLOOD GLUCOSE STABILIZING METHODS AND COMPOSITIONS

CROSS-REFERENCE

This application is a continuation of International Application No. PCT/US2023/061253, filed Jan. 25, 2023, which claims the benefit of U.S. Provisional Application No. 63/303,112 filed Jan. 26, 2022, the entirety of which are hereby incorporated by reference herein.

BACKGROUND

High blood glucose is well-known to have a plethora of negative health effects. Long-term complications from hyperglycemia can range from cardiovascular disease, neuropathy, damage to kidney and blood vessels, to problems in bone and joint. The most used method to control one's blood glucose level is through controlling dietary sugar intake. While this is a sound and proven strategy, it requires a lot of attention from the individual to understand and calculate the amount of carbohydrate consumed every meal. Medications such as insulin are widely used, however, an array of issues can be associated with effectively controlling blood glucoses levels through medication.

SEQUENCE LISTING

The instant application contains a Sequence Listing which has been submitted electronically in XML format and is hereby incorporated by reference in its entirety. Said XML copy, created on Feb. 16, 2023, is named 58654-702601.xml and is 40 KB in size.

SUMMARY

Despite a growing understanding of the biology and etiology of diseases associate with or arising because of high levels of blood glucose, a tremendous burden is nonetheless placed on individuals that cannot regulated blood glucoses levels independently of any intervention. For both medicinal treatments (e.g., insulin hormone) and non-medicinal treatments (e.g., dietary monitoring), both may be viewed as substantive interventions having innate barriers to effective treatment and management of high blood glucose-related disease. Such innate barriers include, for example, treatment adherence (e.g., resulting from treatment complexity), financial burden and access (e.g., out of pocket costs for both insured and uninsured individuals), and other patient-, prescription-, and prescriber-related factors. Such barriers and the resulting effects on the treatment of high blood glucose-related diseases, place a substantial health and economic burden upon individuals and healthcare systems.

Provided and described herein are compositions and methods useful for regulating (e.g., decreasing, stabilizing, etc.) high blood glucose. The provided method and compositions are based on, in part, the surprising discovery that the regulation of high blood glucose can be achieved by providing a legume protein (e.g., pea protein) and an S53 family protease to an individual. In some embodiments, the S53 family protease pro-Kumamolisin. In some embodiments, the S53 protease (e.g., pro-Kumamolisin) comprises an amino acid sequence having at least 85% sequence identity to any one of SEQ ID NOs: 1 and 3-11. In some embodiments, the S53 protease (e.g., pro-Kumamolisin) comprises an amino acid sequence having at least 95% sequence identity to any one of SEQ ID NOs: 1 and 3-11. In some embodiments, the S53 protease (e.g., pro-Kumamolisin) comprises an amino acid sequence having at least 98% sequence identity to any one of SEQ ID NOs: 1 and 3-11. In some embodiments, the active site of the S53 protease comprises amino acid residues E266, F295 or A295, S316, W317, G318, A349, A350 or S350, G351, D352, S353 or D353 or A353 or N353, D367 or E367, G462, G463, T464, S465, and A466 of SEQ ID NO:1.

In some embodiments, the S53 protease is active (e.g., as measure by protein digestion) at a pH less than about pH 5. In some embodiments, the S53 protease is active at a pH less than about pH 4.5. In some embodiments, the S53 protease is active at a pH less than about pH 5. In some embodiments, the S53 protease is active at a pH less than about pH 4. In some embodiments, the S53 protease is active at a pH less than about pH 3.5. In some embodiments, the S53 protease is active at a pH less than about pH 3.

In some embodiments, the S53 protease is active at a pH range between about pH 2 and pH 5. In some embodiments, the S53 protease is active at a pH range between about pH 2.5 and pH 4.5. In some embodiments, the S53 protease is at least 50% active (e.g., relative to its max activity) at a pH range between about pH 2.5 and pH 4.5.

In certain instances, the modulation of protein digestion patterns (e.g., by administering a legume protein and an S53 protease (e.g., pro-Kumamolisin)) increases the concentration of certain dietary amino acids in the blood. In such instances, the modulation protein digestion patterns can induce different physiological responses, such as the discovered lowering of blood glucose levels. In certain instances, digesting dietary proteins in the gut e.g., by administering a legume protein and an S53 protease (e.g., pro-Kumamolisin)) produces bioactive peptides that have impactful biological responses, including anti-diabetic effects (e.g., decreasing blood glucose levels). As described and provided herein, a foodstuff comprised of a protein food (e.g., legume protein) with an acid protease (e.g., pro-Kumamolisin) is capable of lowering the blood sugar level (e.g., when consumed with a sugar). Furthermore, in certain instances, the addition of a protein food (e.g., legume protein) with an acid protease (e.g., pro-Kumamolisin) lowers the glycemic index of a foodstuff (e.g., a foodstuff comprising a sugar).

Provided and described herein are methods of decreasing blood glucose in a subject, comprising: administering to the subject a composition comprising: a legume protein; and an S53 protease (e.g., pro-Kumamolisin). Also described and provided are methods of reducing an increase in blood glucose in a subject, comprising: administering to the subject a composition comprising a legume protein; and an S53 protease (e.g., pro-Kumamolisin).

In some embodiments, the S53 protease (e.g., pro-Kumamolisin) comprises an amino acid sequence having at least 85% sequence identity to SEQ ID NO: 1. In some embodiments, the S53 protease (e.g., pro-Kumamolisin) comprises an amino acid sequence having at least 95% sequence identity to SEQ ID NO: 1. In some embodiments, the S53 protease (e.g., pro-Kumamolisin) comprises an amino acid sequence having at least 98% sequence identity to SEQ ID NO: 1.

In some embodiments, wherein the S53 protease (e.g., pro-Kumamolisin) comprises an amino acid sequence of SEQ ID NO: 1. In some embodiments, the S53 protease (e.g., pro-Kumamolisin) comprises an active site comprising amino acid residues E266, F295, S316, W317, G318, A349, A350, G351, D352, S353, D367, G462, G463, T464, S465, and A466 of SEQ ID NO:1. In some embodiments, the S53 protease (e.g., pro-Kumamolisin) comprises an active site comprising one or more amino acid substitutions of residues E266, F295, S316, W317, G318, A349, A350, G351, D352, S353, D367, G462, G463, T464, S465, and A466 of SEQ ID NO:1. In some embodiments, the active site comprises between one and five amino acid substitutions. In some embodiments, the S53 protease (e.g., pro-Kumamolisin) comprises one or more truncations of SEQ ID NO:1, wherein the one or more truncations comprises an N-terminal truncation, a C-terminal truncation, or both an N-terminal and C-terminal truncation.

In some embodiments, the legume protein is a pea protein. In some embodiments, the pea protein is derived from a pea. In certain embodiments, the pea is a garden pea, a sugar pea, a field pea, or any combination thereof. In certain embodiments, the pea is a garden pea. In certain embodiments, the pea is a sugar pea. In certain embodiments, the pea is a field pea. In certain embodiments, the pea is any combination of a garden pea, a sugar pea, and/or a field pea. In some embodiments, the pea is a standard pea, a commoditized pea, a genetically modified pea, or a combination thereof. In certain embodiments, the pea is a smooth pea, a wrinkled pea, or a combination thereof.

In some embodiments, the administering occurs after the subject ingests a foodstuff comprising sugar. In some embodiments, the increase in blood sugar is reduced relative to administering a composition that does not comprise the S53 protease (e.g., pro-Kumamolisin). In some embodiments, the subject self-administers the composition.

In some embodiments, the subject is a mammal. In some embodiments, the mammal is a human. In some embodiments, the human has hyperglycemia. In some embodiments, the human has a condition associated with and/or caused by hyperglycemia. In some embodiments, the condition is cardiovascular disease or neuropathy or diabetic nephropathy or retinopathy or cataract or bone and joint problems or teeth and gum infections.

Also proved are compositions for use in decreasing blood sugar in a subject, the composition comprising a legume protein and an S53 protease (e.g., pro-Kumamolisin). Further provided are compositions for use in reducing an increase blood sugar in a subject, the composition comprising a legume protein and an S53 protease (e.g., pro-Kumamolisin).

In some embodiments, provided is a composition comprising a foodstuff, a legume protein (e.g., pea protein), and an S53 protease (e.g., pro-Kumamolisin) (e.g., any one of the S53 proteases (e.g., pro-Kumamolisin) described herein). In certain embodiments, the composition comprising the foodstuff, the legume protein, and the S53 protease (e.g., pro-Kumamolisin) results in a lower increase in blood sugar after consumption than a second composition comprising the foodstuff alone.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
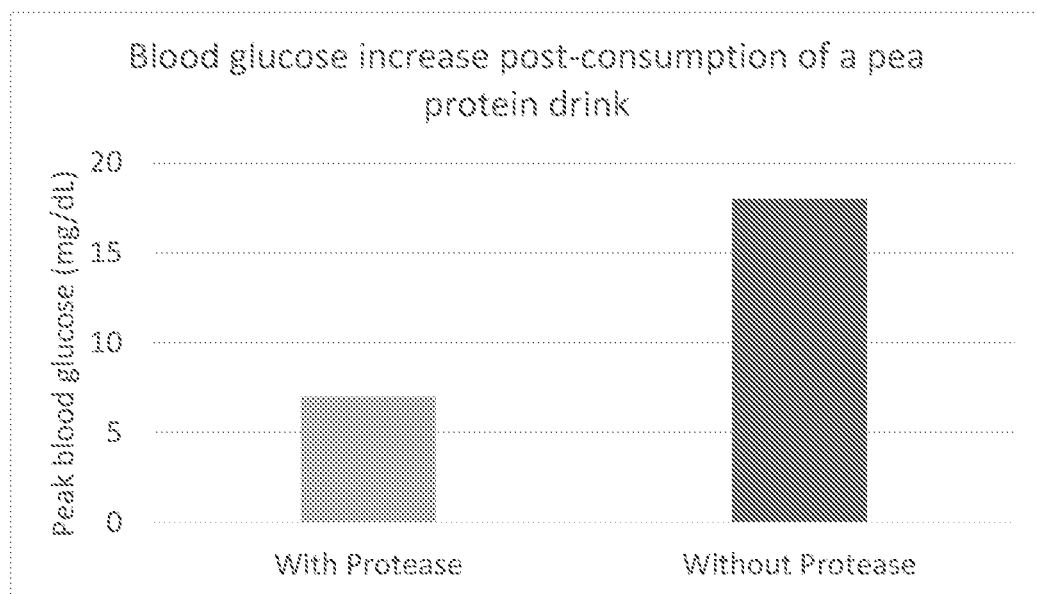
FIG. 1 shows lowering of blood glucose after administering a legume protein and S53 protease (e.g., pro-Kumamolisin).
Figure 2:
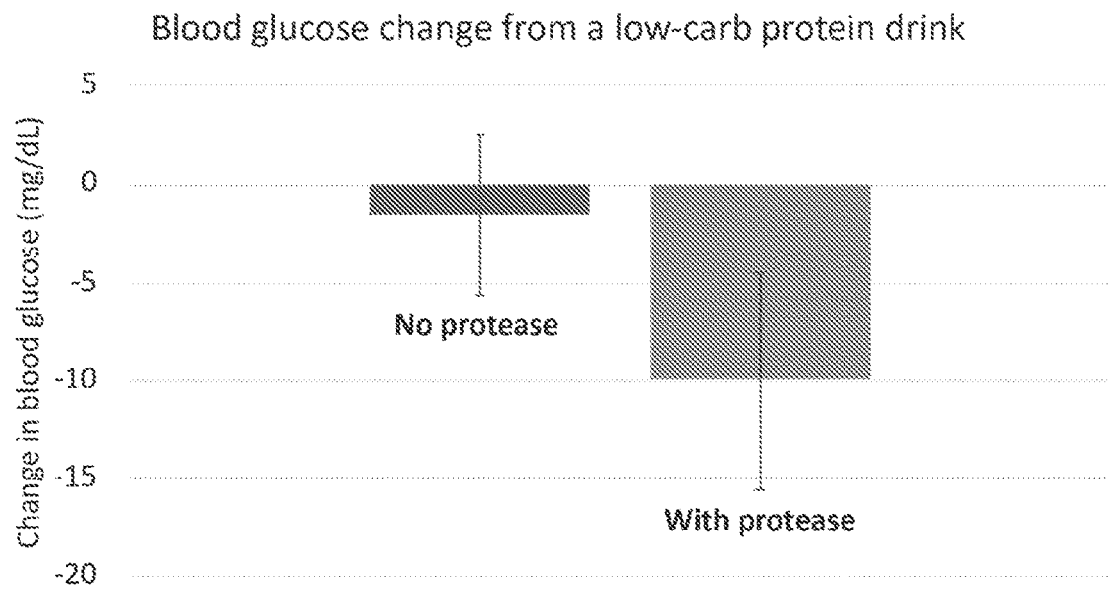
FIG. 2 shows lowering of blood glucose after administering a low-carb protein drink and protease.
Figure 3:
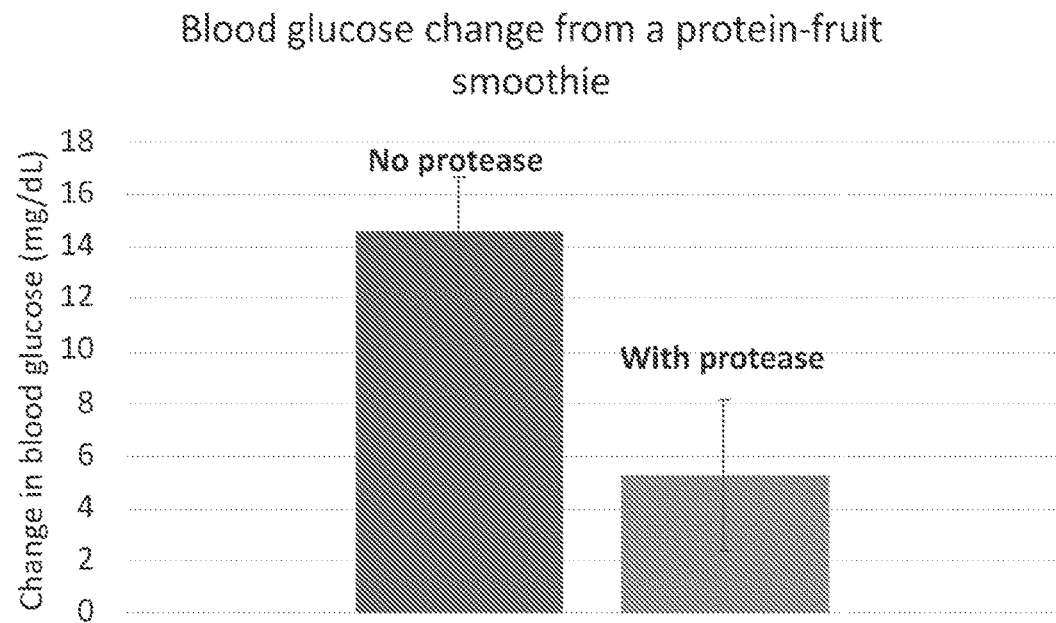
FIG. 3 shows lowering of blood glucose after administering a protein-fruit smoothie and protease.
Figure 4:
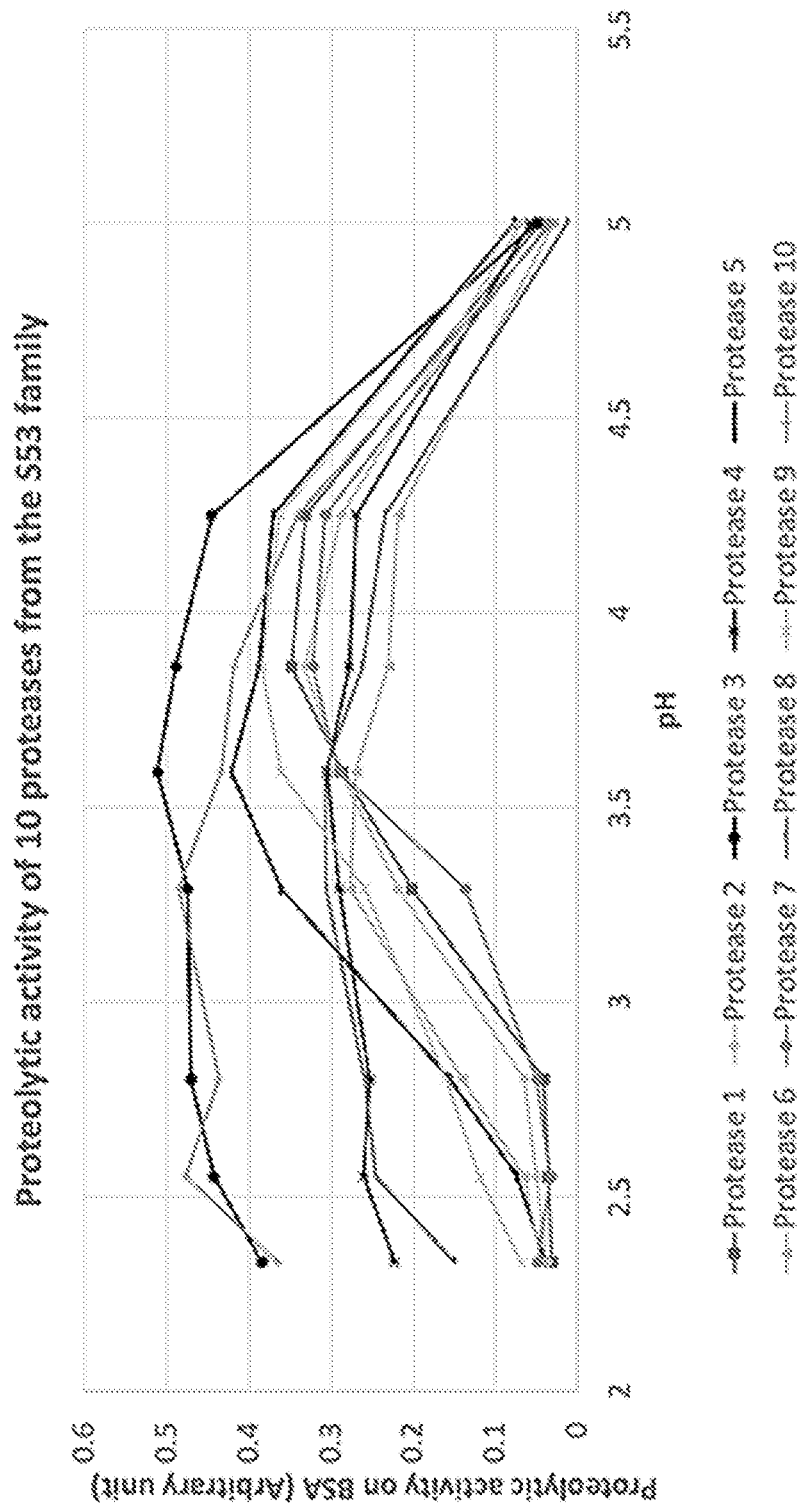
FIG. 4 shows proteolytic activity of representative S53 proteases at low pH ranges.

The dysregulation of blood glucose and/or the presence of high blood glucose sugar level is associated with and/or causal of a variety of diseases that affect human health and wellbeing. Such diseases (e.g., diabetes) tend to be complex conditions having burdensome symptoms associated therewith, and are further hallmarked by glucose dysregulation. In certain instances, the methods and compositions provided herein are useful in decreasing and/or reducing blood glucose levels in an individual. Notably, in certain instances, the methods and compositions provided herein are based on the discovery that administering a legume protein (e.g., pea protein) and an S53 protease (e.g., pro-Kumamolisin) lowers (e.g., decreases or reduces) blood sugar levels. Furthermore, in certain instances, the methods and compositions provided herein are useful in inhibiting, reducing, decreasing, and/or preventing an increase in blood glucose levels (e.g., the amount of glucose in the blood).

Legume Proteins

A legume is a plant of the family Fabaceae. A legume, as used herein, generally describes and refers to the fruit or seed of a legume plant. In certain embodiments, the compositions and methods utilized a legume protein. A legume protein, generally described a protein derived from (e.g., obtained from) the fruit or seed of a legume plant. Both intact legume protein and hydrolyzed legume protein sources can be used. In some embodiments, the legume protein is an intact legume protein. In some embodiments, the legume protein is a hydrolyzed legume protein. In some embodiments, the legume protein is provided in solid form. In some embodiments, the legume protein is provided in liquid form. In some embodiments, the legume protein concentrate (e.g., protein material that is obtained from pea upon removal of soluble carbohydrate, ash, and other minor constituents).

In some embodiments, the legume protein is a pea protein. A pea generally refers to and includes the seed or the seed-pod of the pod from a plant belonging to the genus *Pisum sativum*. A pea protein, generally described a protein derived from (e.g., obtained from) the fruit or seed of a pea plant. Both intact pea protein and hydrolyzed pea protein sources can be used. In some embodiments, the pea protein is an intact legume protein. In some embodiments, the pea protein is a hydrolyzed legume protein. In some embodiments, the pea protein is provided in solid form. In some embodiments, the pea protein is provided in liquid form. In some embodiments, the pea protein concentrate (e.g., protein material that is obtained from pea upon removal of soluble carbohydrate, ash, and other minor constituents). In certain embodiments, the pea is a garden pea, a sugar pea, a field pea, or any combination thereof. In certain embodiments, the pea is a garden pea. In certain embodiments, the pea is a sugar pea. In certain embodiments, the pea is a field pea. In certain embodiments, the pea is any combination of a garden pea, a sugar pea, and/or a field pea. In some embodiments, the pea is a standard pea, a commoditized pea, a genetically modified pea, or a combination thereof. In certain embodiments, the pea is a smooth pea, a wrinkled pea, or a combination thereof.

Proteases

The compositions and methods described herein generally utilize an acid protease. In some embodiments, the acid protease is an S53 family protease. S53 family proteases generally refer to and include the family of serine proteases found in prokaryotes and eukaryotes. In some embodiments, the S53 family proteases refer to and include proteases within and/or identified by MEROPS Accession MER0000995 (e.g., sedolisin, sedolisin-b, tripeptidyl-peptidase I, kumamolisin, kumamolisin-B, physarolisin, aorsin, physarolisin II, kumamolisin-As, grifolisin, scytalidolisin, among others). In some embodiments, the acid protease is an S53 protease (e.g., pro-Kumamolisin). Pro-Kumamolisin generally refers to and includes the thermostable calcium-dependent endopeptidase derived from an acid/thermophilic *Bacillus* (*Bacillus novo* sp. MN-32). In some embodiments, pro-Kumamolisin refers to and includes NCBI Gene ID: 18765799 (NCBI Reference Sequence XP_007297753.1, XM_007297691.1 to XP_007297753, and/or NW_006763082.1 (137488 . . . 139728).

In some embodiments, the S53 protease comprises an amino acid sequence as set forth in SEQ ID NO: 1. In some embodiments, the S53 protease comprises an amino acid sequence having equal to or greater than 80% sequence identity to SEQ ID NO: 1. In some embodiments, the S53 protease comprises an amino acid sequence having equal to or greater than 85% sequence identity to SEQ ID NO: 1. In some embodiments, the S53 protease comprises an amino acid sequence having equal to or greater than 90% sequence identity to SEQ ID NO: 1. In some embodiments, the S53 protease comprises an amino acid sequence having equal to or greater than 95% sequence identity to SEQ ID NO: 1. In some embodiments, the S53 protease comprises an amino acid sequence having equal to or greater than 97% sequence identity to SEQ ID NO: 1. In some embodiments, the S53 protease comprises an amino acid sequence having equal to or greater than 98% sequence identity to SEQ ID NO: 1. In some embodiments, the S53 protease comprises an amino acid sequence having equal to or greater than 99% sequence identity to SEQ ID NO: 1.

In some embodiments, the S53 protease comprises an amino acid sequence as set forth in SEQ ID NO: 2. In some embodiments, the S53 protease comprises an amino acid sequence having equal to or greater than 80% sequence identity to SEQ ID NO: 2. In some embodiments, the S53 protease comprises an amino acid sequence having equal to or greater than 85% sequence identity to SEQ ID NO: 2. In some embodiments, the S53 protease comprises an amino acid sequence having equal to or greater than 90% sequence identity to SEQ ID NO: 2. In some embodiments, the S53 protease comprises an amino acid sequence having equal to or greater than 95% sequence identity to SEQ ID NO: 2. In some embodiments, the S53 protease comprises an amino acid sequence having equal to or greater than 97% sequence identity to SEQ ID NO: 2. In some embodiments, the S53 protease comprises an amino acid sequence having equal to or greater than 98% sequence identity to SEQ ID NO: 2. In some embodiments, the S53 protease comprises an amino acid sequence having equal to or greater than 99% sequence identity to SEQ ID NO: 2.

In some embodiments, the S53 protease comprises an amino acid sequence as set forth in SEQ ID NO: 3. In some embodiments, the S53 protease comprises an amino acid sequence having equal to or greater than 80% sequence identity to SEQ ID NO: 3. In some embodiments, the S53 protease comprises an amino acid sequence having equal to or greater than 85% sequence identity to SEQ ID NO: 3. In some embodiments, the S53 protease comprises an amino acid sequence having equal to or greater than 90% sequence identity to SEQ ID NO: 3. In some embodiments, the S53 protease comprises an amino acid sequence having equal to or greater than 95% sequence identity to SEQ ID NO: 3. In some embodiments, the S53 protease comprises an amino acid sequence having equal to or greater than 97% sequence identity to SEQ ID NO: 3. In some embodiments, the S53 protease comprises an amino acid sequence having equal to or greater than 98% sequence identity to SEQ ID NO: 3. In some embodiments, the S53 protease comprises an amino acid sequence having equal to or greater than 99% sequence identity to SEQ ID NO: 3.

In some embodiments, the S53 protease comprises an amino acid sequence as set forth in SEQ ID NO: 4. In some embodiments, the S53 protease comprises an amino acid sequence having equal to or greater than 80% sequence identity to SEQ ID NO: 4. In some embodiments, the S53 protease comprises an amino acid sequence having equal to or greater than 85% sequence identity to SEQ ID NO: 4. In some embodiments, the S53 protease comprises an amino acid sequence having equal to or greater than 90% sequence identity to SEQ ID NO: 4. In some embodiments, a pro-Kumamolisin comprises an amino acid sequence having equal to or greater than 95% sequence identity to SEQ ID NO: 4. In some embodiments, the S53 protease comprises an amino acid sequence having equal to or greater than 97% sequence identity to SEQ ID NO: 4. In some embodiments, the S53 protease comprises an amino acid sequence having equal to or greater than 98% sequence identity to SEQ ID NO: 4. In some embodiments, the S53 protease comprises an amino acid sequence having equal to or greater than 99% sequence identity to SEQ ID NO: 4.

In some embodiments, the S53 protease comprises an amino acid sequence as set forth in SEQ ID NO: 5. In some embodiments, the S53 protease comprises an amino acid sequence having equal to or greater than 80% sequence identity to SEQ ID NO: 5. In some embodiments, the S53 protease comprises an amino acid sequence having equal to or greater than 85% sequence identity to SEQ ID NO: 5. In some embodiments, the S53 protease comprises an amino acid sequence having equal to or greater than 90% sequence identity to SEQ ID NO: 5. In some embodiments, the S53 protease comprises an amino acid sequence having equal to or greater than 95% sequence identity to SEQ ID NO: 5. In some embodiments, the S53 protease comprises an amino acid sequence having equal to or greater than 97% sequence identity to SEQ ID NO: 5. In some embodiments, the S53 protease comprises an amino acid sequence having equal to or greater than 98% sequence identity to SEQ ID NO: 5. In some embodiments, the S53 protease comprises an amino acid sequence having equal to or greater than 99% sequence identity to SEQ ID NO: 5.

In some embodiments, the S53 protease comprises an amino acid sequence as set forth in SEQ ID NO: 6. In some embodiments, the S53 protease comprises an amino acid sequence having equal to or greater than 80% sequence identity to SEQ ID NO: 6. In some embodiments, the S53 protease comprises an amino acid sequence having equal to or greater than 85% sequence identity to SEQ ID NO: 6. In some embodiments, the S53 protease comprises an amino acid sequence having equal to or greater than 90% sequence identity to SEQ ID NO: 6. In some embodiments, the S53 protease comprises an amino acid sequence having equal to or greater than 95% sequence identity to SEQ ID NO: 6. In some embodiments, the S53 protease comprises an amino acid sequence having equal to or greater than 97% sequence identity to SEQ ID NO: 6. In some embodiments, the S53 protease comprises an amino acid sequence having equal to or greater than 98% sequence identity to SEQ ID NO: 6. In some embodiments, the S53 protease comprises an amino acid sequence having equal to or greater than 99% sequence identity to SEQ ID NO: 6.

In some embodiments, the S53 protease comprises an amino acid sequence as set forth in SEQ ID NO: 7. In some embodiments, the S53 protease comprises an amino acid sequence having equal to or greater than 80% sequence identity to SEQ ID NO: 7. In some embodiments, the S53 protease comprises an amino acid sequence having equal to or greater than 85% sequence identity to SEQ ID NO: 7. In some embodiments, the S53 protease comprises an amino acid sequence having equal to or greater than 90% sequence identity to SEQ ID NO: 7. In some embodiments, the S53 protease comprises an amino acid sequence having equal to or greater than 95% sequence identity to SEQ ID NO: 7. In some embodiments, the S53 protease comprises an amino acid sequence having equal to or greater than 97% sequence identity to SEQ ID NO: 7. In some embodiments, the S53 protease comprises an amino acid sequence having equal to or greater than 98% sequence identity to SEQ ID NO: 7. In some embodiments, the S53 protease comprises an amino acid sequence having equal to or greater than 99% sequence identity to SEQ ID NO: 7.

In some embodiments, the S53 protease comprises an amino acid sequence as set forth in SEQ ID NO: 8. In some embodiments, the S53 protease comprises an amino acid sequence having equal to or greater than 80% sequence identity to SEQ ID NO: 8. In some embodiments, the S53 protease comprises an amino acid sequence having equal to or greater than 85% sequence identity to SEQ ID NO: 8. In some embodiments, the S53 protease comprises an amino acid sequence having equal to or greater than 90% sequence identity to SEQ ID NO: 8. In some embodiments, the S53 protease comprises an amino acid sequence having equal to or greater than 95% sequence identity to SEQ ID NO: 8. In some embodiments, the S53 protease comprises an amino acid sequence having equal to or greater than 97% sequence identity to SEQ ID NO: 8. In some embodiments, the S53 protease comprises an amino acid sequence having equal to or greater than 98% sequence identity to SEQ ID NO: 8. In some embodiments, the S53 protease comprises an amino acid sequence having equal to or greater than 99% sequence identity to SEQ ID NO: 8.

In some embodiments, the S53 protease comprises an amino acid sequence as set forth in SEQ ID NO: 9. In some embodiments, the S53 protease comprises an amino acid sequence having equal to or greater than 80% sequence identity to SEQ ID NO: 9. In some embodiments, the S53 protease comprises an amino acid sequence having equal to or greater than 85% sequence identity to SEQ ID NO: 9. In some embodiments, the S53 protease comprises an amino acid sequence having equal to or greater than 90% sequence identity to SEQ ID NO: 9. In some embodiments, the S53 protease comprises an amino acid sequence having equal to or greater than 95% sequence identity to SEQ ID NO: 9. In some embodiments, the S53 protease comprises an amino acid sequence having equal to or greater than 97% sequence identity to SEQ ID NO: 9. In some embodiments, the S53 protease comprises an amino acid sequence having equal to or greater than 98% sequence identity to SEQ ID NO: 9. In some embodiments, the S53 protease comprises an amino acid sequence having equal to or greater than 99% sequence identity to SEQ ID NO: 9.

In some embodiments, the S53 protease comprises an amino acid sequence as set forth in SEQ ID NO: 10. In some embodiments, the S53 protease comprises an amino acid sequence having equal to or greater than 80% sequence identity to SEQ ID NO: 10. In some embodiments, the S53 protease comprises an amino acid sequence having equal to or greater than 85% sequence identity to SEQ ID NO: 10. In some embodiments, the S53 protease comprises an amino acid sequence having equal to or greater than 90% sequence identity to SEQ ID NO: 10. In some embodiments, the S53 protease comprises an amino acid sequence having equal to or greater than 95% sequence identity to SEQ ID NO: 10. In some embodiments, the S53 protease comprises an amino acid sequence having equal to or greater than 97% sequence identity to SEQ ID NO: 10. In some embodiments, the S53 protease comprises an amino acid sequence having equal to or greater than 98% sequence identity to SEQ ID NO: 10. In some embodiments, the S53 protease comprises an amino acid sequence having equal to or greater than 99% sequence identity to SEQ ID NO: 10.

In some embodiments, the S53 protease comprises an amino acid sequence as set forth in SEQ ID NO: 11. In some embodiments, the S53 protease comprises an amino acid sequence having equal to or greater than 80% sequence identity to SEQ ID NO: 11. In some embodiments, the S53 protease comprises an amino acid sequence having equal to or greater than 85% sequence identity to SEQ ID NO: 11. In some embodiments, the S53 protease comprises an amino acid sequence having equal to or greater than 90% sequence identity to SEQ ID NO: 11. In some embodiments, the S53 protease comprises an amino acid sequence having equal to or greater than 95% sequence identity to SEQ ID NO: 11. In some embodiments, the S53 protease comprises an amino acid sequence having equal to or greater than 97% sequence identity to SEQ ID NO: 11. In some embodiments, the S53 protease comprises an amino acid sequence having equal to or greater than 98% sequence identity to SEQ ID NO: 11. In some embodiments, the S53 protease comprises an amino acid sequence having equal to or greater than 99% sequence identity to SEQ ID NO: 11.

In some embodiments, the active site of the S53 protease comprises amino acid residues E266, F295 or A295, S316, W317, G318, A349, A350 or S350, G351, D352, S353 or D353 or A353 or N353, D367 or E367, G462, G463, T464, S465, and A466 of SEQ ID NO:1.

The determination of percent identity or percent similarity between two sequences can be accomplished using a mathematical algorithm. In some embodiments, a non-limiting example of a mathematical algorithm utilized for the comparison of two sequences is the algorithm of Karlin and Altschul, 1990, *Proc. Natl. Acad. Sci. USA* 87:2264-2268, modified as in Karlin and Altschul, 1993, *Proc. Natl. Acad. Sci. USA* 90:5873-5877. Such an algorithm is incorporated into the NBLAST and XBLAST programs of Altschul et al., 1990, J. Mol. Biol. 215:403-410. Alternatively, in some embodiments, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. In some embodiments, a non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. Additional algorithms for sequence analysis are known in the art and include ADVANCE and ADAM as described in Torellis and Robotti, 1994, *Comput. Appl. Biosci.* 10:3-5; and FASTA described in Pearson and Lipman, 1988, *Proc. Natl. Acad. Sci. USA* 85:2444-8. In some embodiments, sequence alignment is be carried out using the CLUSTAL algorithm, as described by Higgins et al., 1996, *Methods Enzymol.* 266:383-402.

In some embodiments, the active site of an S53 protease (e.g., pro-Kumamolisin) comprises amino acid residues E266, F295, S316, W317, G318, A349, A350, G351, D352, S353, D367, G462, G463, T464, S465, and A466 of SEQ ID NO:1. In some embodiments, the S53 protease (e.g., pro-Kumamolisin) comprises an active site comprising one or more amino acid substitutions of residues E266, F295, S316, W317, G318, A349, A350, G351, D352, S353, D367, G462, G463, T464, S465, and A466 of SEQ ID NO:1. In some embodiments, the active site comprises between one and five amino acid substitutions.

In some embodiments, the active site comprises between one or more amino acid substitutions. In some embodiments, the active site comprises between two or more amino acid substitutions. In some embodiments, the active site comprises between three or more amino acid substitutions. In some embodiments, the active site comprises between four or more amino acid substitutions.

In some embodiments, the active site comprises one amino acid substitution. In some embodiments, the active site comprises two amino acid substitutions. In some embodiments, the active site comprises three amino acid substitutions. In some embodiments, the active site comprises four amino acid substitutions. In some embodiments, the active site comprises five amino acid substitutions.

An amino acid generally refers to and/or includes naturally occurring amino acids, unnatural amino acids, amino acid analogues and amino acid mimetics that function in a manner similar to a naturally occurring amino acids. Amino acids are generally referred to herein by either their name, the commonly known three letter symbols, or by the one-letter symbols recommended by the IUPAC-IUB Biochemical Nomenclature Commission. As used herein, naturally occurring amino acids include and/or refer to amino acids which are generally found in nature and are not manipulated by man. In some embodiments, naturally occurring includes and/or further refers to the 20 conventional amino acids: alanine (A or Ala), cysteine (C or Cys), aspartic acid (D or Asp), glutamic acid (E or Glu), phenylalanine (F or Phe), glycine (G or Gly), histidine (H or His), isoleucine (I or Ile), lysine (K or Lys), leucine (L or Leu), methionine (M or Met), asparagine (N or Asn), proline (P or Pro), glutamine (Q or Gln), arginine (R or Arg), serine (S or Ser), threonine (T or Thr), valine (V or Val), tryptophan (W or Trp), and tyrosine (Y or Tyr).

In some embodiments, a non-polar amino acid can be substituted and replaced with another non-polar amino acid, wherein non-polar amino acids include alanine, leucine, isoleucine, valine, glycine, proline, phenylalanine, tryptophan and methionine. In some embodiments, a neutrally charged polar amino acids can be substituted and replaced with another neutrally charged polar amino acid, wherein neutrally charged polar amino acids include serine, threonine, cysteine, tyrosine, asparagine, and glutamine. In some embodiments, a positively charged amino acid can be substituted and replaced with another positively charged amino acid, wherein positively charged amino acids include arginine, lysine and histidine. In some embodiments, a negatively charged amino acid can be substituted and replaced with another negatively charged amino acid, wherein negatively charged amino acids include aspartic acid and glutamic acid. As used herein, a peptide includes and/or refers to any of various natural or synthetic compounds containing two or more amino acids joined by a peptide bond that link the carboxyl group of one amino acid to the amino group of another. As also used herein, amino acid refers to and/or includes naturally occurring amino acids, unnatural amino acids, amino acid analogues and amino acid mimetics that function in a manner similar to a naturally occurring amino acids. Amino acids are generally referred to herein by either their name, the commonly known three letter symbols, or by the one-letter symbols recommended by the IUPAC-IUB Biochemical Nomenclature Commission.

In some embodiments, the active site comprises between one and five amino acid substitutions. In some embodiments, the S53 protease (e.g., pro-Kumamolisin) comprises one or more truncations of SEQ ID NO:1, wherein the one or more truncations comprises an N-terminal truncation, a C-terminal truncation, or both an N-terminal and C-terminal truncation.

In some embodiments, the S53 protease is active (e.g., as measure by protein digestion) at a pH less than about pH 5. In some embodiments, the S53 protease is active at a pH less than about pH 4.5. In some embodiments, the S53 protease is active at a pH less than about pH 5. In some embodiments, the S53 protease is active at a pH less than about pH 4. In some embodiments, the S53 protease is active at a pH less than about pH 3.5. In some embodiments, the S53 protease is active at a pH less than about pH 3.

In some embodiments, the S53 protease is active at a pH range between about pH 2 and pH 5 In some embodiments, the S53 protease is active at a pH range between about pH 2.5 and pH 4.5. In some embodiments, the S53 protease is at least 50% active (e.g., relative to its max activity) at a pH range between about pH 2.5 and pH 4.5.

The S53 protease (e.g., pro-Kumamolisin) can be administered as part of a composition comprising the S53 protease (e.g., pro-Kumamolisin). The composition can further comprise the legume protein. In some embodiments, provided is a composition comprising the S53 protease (e.g., pro-Kumamolisin). In certain embodiments, the composition further comprises a legume protein (e.g., pea protein).

In some embodiments, provided is a composition comprising a foodstuff, a legume protein (e.g., pea protein), and an S53 protease (e.g., pro-Kumamolisin) (e.g., any one of the S53 proteases (e.g., pro-Kumamolisin) described herein). In certain embodiments, the foodstuff comprises a sugar. In certain embodiments, the sugar comprises sucrose, lactose, maltose, or another di-, tri-, or polysaccharides that contain glucose as a monomer. In certain embodiments, the sugar comprises sucrose. In certain embodiments, the sugar comprises lactose. In certain embodiments, the sugar comprises maltose. In certain embodiments, the sugar comprises di-, tri-, or polysaccharides that contain glucose as a monomer. In certain instances, the addition of the legume protein (e.g., pea protein) and the S53 protease (e.g., pro-Kumamolisin) lowers the glycemic index of the composition comprising the foodstuff. In certain embodiments, the composition comprising the foodstuff, the legume protein, and the S53 protease (e.g., pro-Kumamolisin) results in a lower increase in blood sugar after consumption than a second composition comprising the foodstuff alone.

In some embodiments, composition comprises about 5 grams (g) of legume protein (e.g., pea protein) to about 60 grams (g) of legume protein (e.g., pea protein). In some embodiments, composition comprises about 5 grams (g) of legume protein (e.g., pea protein) to about 10 grams (g) of legume protein (e.g., pea protein), about 5 grams (g) of legume protein (e.g., pea protein) to about 15 grams (g) of legume protein (e.g., pea protein), about 5 grams (g) of legume protein (e.g., pea protein) to about 20 grams (g) of legume protein (e.g., pea protein), about 5 grams (g) of legume protein (e.g., pea protein) to about 25 grams (g) of legume protein (e.g., pea protein), about 5 grams (g) of legume protein (e.g., pea protein) to about 30 grams (g) of legume protein (e.g., pea protein), about 5 grams (g) of legume protein (e.g., pea protein) to about 35 grams (g) of legume protein (e.g., pea protein), about 5 grams (g) of legume protein (e.g., pea protein) to about 40 grams (g) of legume protein (e.g., pea protein), about 5 grams (g) of legume protein (e.g., pea protein) to about 45 grams (g) of legume protein (e.g., pea protein), about 5 grams (g) of legume protein (e.g., pea protein) to about 50 grams (g) of legume protein (e.g., pea protein), about 5 grams (g) of legume protein (e.g., pea protein) to about 60 grams (g) of legume protein (e.g., pea protein), about 10 grams (g) of legume protein (e.g., pea protein) to about 15 grams (g) of legume protein (e.g., pea protein), about 10 grams (g) of legume protein (e.g., pea protein) to about 20 grams (g) of legume protein (e.g., pea protein), about 10 grams (g) of legume protein (e.g., pea protein) to about 25 grams (g) of legume protein (e.g., pea protein), about 10 grams (g) of legume protein (e.g., pea protein) to about 30 grams (g) of legume protein (e.g., pea protein), about 10 grams (g) of legume protein (e.g., pea protein) to about 35 grams (g) of legume protein (e.g., pea protein), about 10 grams (g) of legume protein (e.g., pea protein) to about 40 grams (g) of legume protein (e.g., pea protein), about 10 grams (g) of legume protein (e.g., pea protein) to about 45 grams (g) of legume protein (e.g., pea protein), about 10 grams (g) of legume protein (e.g., pea protein) to about 50 grams (g) of legume protein (e.g., pea protein), about 10 grams (g) of legume protein (e.g., pea protein) to about 60 grams (g) of legume protein (e.g., pea protein), about 15 grams (g) of legume protein (e.g., pea protein) to about 20 grams (g) of legume protein (e.g., pea protein), about 15 grams (g) of legume protein (e.g., pea protein) to about 25 grams (g) of legume protein (e.g., pea protein), about 15 grams (g) of legume protein (e.g., pea protein) to about 30 grams (g) of legume protein (e.g., pea protein), about 15 grams (g) of legume protein (e.g., pea protein) to about 35 grams (g) of legume protein (e.g., pea protein), about 15 grams (g) of legume protein (e.g., pea protein) to about 40 grams (g) of legume protein (e.g., pea protein), about 15 grams (g) of legume protein (e.g., pea protein) to about 45 grams (g) of legume protein (e.g., pea protein), about 15 grams (g) of legume protein (e.g., pea protein) to about 50 grams (g) of legume protein (e.g., pea protein), about 15 grams (g) of legume protein (e.g., pea protein) to about 60 grams (g) of legume protein (e.g., pea protein), about 20 grams (g) of legume protein (e.g., pea protein) to about 25 grams (g) of legume protein (e.g., pea protein), about 20 grams (g) of legume protein (e.g., pea protein) to about 30 grams (g) of legume protein (e.g., pea protein), about 20 grams (g) of legume protein (e.g., pea protein) to about 35 grams (g) of legume protein (e.g., pea protein), about 20 grams (g) of legume protein (e.g., pea protein) to about 40 grams (g) of legume protein (e.g., pea protein), about 20 grams (g) of legume protein (e.g., pea protein) to about 45 grams (g) of legume protein (e.g., pea protein), about 20 grams (g) of legume protein (e.g., pea protein) to about 50 grams (g) of legume protein (e.g., pea protein), about 20 grams (g) of legume protein (e.g., pea protein) to about 60 grams (g) of legume protein (e.g., pea protein), about 25 grams (g) of legume protein (e.g., pea protein) to about 30 grams (g) of legume protein (e.g., pea protein), about 25 grams (g) of legume protein (e.g., pea protein) to about 35 grams (g) of legume protein (e.g., pea protein), about 25 grams (g) of legume protein (e.g., pea protein) to about 40 grams (g) of legume protein (e.g., pea protein), about 25 grams (g) of legume protein (e.g., pea protein) to about 45 grams (g) of legume protein (e.g., pea protein), about 25 grams (g) of legume protein (e.g., pea protein) to about 50 grams (g) of legume protein (e.g., pea protein), about 25 grams (g) of legume protein (e.g., pea protein) to about 60 grams (g) of legume protein (e.g., pea protein), about 30 grams (g) of legume protein (e.g., pea protein) to about 35 grams (g) of legume protein (e.g., pea protein), about 30 grams (g) of legume protein (e.g., pea protein) to about 40 grams (g) of legume protein (e.g., pea protein), about 30 grams (g) of legume protein (e.g., pea protein) to about 45 grams (g) of legume protein (e.g., pea protein), about 30 grams (g) of legume protein (e.g., pea protein) to about 50 grams (g) of legume protein (e.g., pea protein), about 30 grams (g) of legume protein (e.g., pea protein) to about 60 grams (g) of legume protein (e.g., pea protein), about 35 grams (g) of legume protein (e.g., pea protein) to about 40 grams (g) of legume protein (e.g., pea protein), about 35 grams (g) of legume protein (e.g., pea protein) to about 45 grams (g) of legume protein (e.g., pea protein), about 35 grams (g) of legume protein (e.g., pea protein) to about 50 grams (g) of legume protein (e.g., pea protein), about 35 grams (g) of legume protein (e.g., pea protein) to about 60 grams (g) of legume protein (e.g., pea protein), about 40 grams (g) of legume protein (e.g., pea protein) to about 45 grams (g) of legume protein (e.g., pea protein), about 40 grams (g) of legume protein (e.g., pea protein) to about 50 grams (g) of legume protein (e.g., pea protein), about 40 grams (g) of legume protein (e.g., pea protein) to about 60 grams (g) of legume protein (e.g., pea protein), about 45 grams (g) of legume protein (e.g., pea protein) to about 50 grams (g) of legume protein (e.g., pea protein), about 45 grams (g) of legume protein (e.g., pea protein) to about 60 grams (g) of legume protein (e.g., pea protein), or about 50 grams (g) of legume protein (e.g., pea protein) to about 60 grams (g) of legume protein (e.g., pea protein). In some embodiments, composition comprises about 5 grams (g) of legume protein (e.g., pea protein), about 10 grams (g) of legume protein (e.g., pea protein), about 15 grams (g) of legume protein (e.g., pea protein), about 20 grams (g) of legume protein (e.g., pea protein), about 25 grams (g) of legume protein (e.g., pea protein), about 30 grams (g) of legume protein (e.g., pea protein), about 35 grams (g) of legume protein (e.g., pea protein), about 40 grams (g) of legume protein (e.g., pea protein), about 45 grams (g) of legume protein (e.g., pea protein), about 50 grams (g) of legume protein (e.g., pea protein), or about 60 grams (g) of legume protein (e.g., pea protein). In some embodiments, composition comprises at least about 5 grams (g) of legume protein (e.g., pea protein), about 10 grams (g) of legume protein (e.g., pea protein), about 15 grams (g) of legume protein (e.g., pea protein), about 20 grams (g) of legume protein (e.g., pea protein), about 25 grams (g) of legume protein (e.g., pea protein), about 30 grams (g) of legume protein (e.g., pea protein), about 35 grams (g) of legume protein (e.g., pea protein), about 40 grams (g) of legume protein (e.g., pea protein), about 45 grams (g) of legume protein (e.g., pea protein), or about 50 grams (g) of legume protein (e.g., pea protein). In some embodiments, composition comprises at most about 10 grams (g) of legume protein (e.g., pea protein), about 15 grams (g) of legume protein (e.g., pea protein), about 20 grams (g) of legume protein (e.g., pea protein), about 25 grams (g) of legume protein (e.g., pea protein), about 30 grams (g) of legume protein (e.g., pea protein), about 35 grams (g) of legume protein (e.g., pea protein), about 40 grams (g) of legume protein (e.g., pea protein), about 45 grams (g) of legume protein (e.g., pea protein), about 50 grams (g) of legume protein (e.g., pea protein), or about 60 grams (g) of legume protein (e.g., pea protein).

In some embodiments, composition comprises about 50 milligrams (mg) of pro-Kumamolisin to about 2,000 milligrams (mg) of pro-Kumamolisin. In some embodiments, composition comprises about 50 milligrams (mg) of pro-Kumamolisin to about 100 milligrams (mg) of pro-Kumamolisin, about 50 milligrams (mg) of pro-Kumamolisin to about 200 milligrams (mg) of pro-Kumamolisin, about 50 milligrams (mg) of pro-Kumamolisin to about 300 milligrams (mg) of pro-Kumamolisin, about 50 milligrams (mg) of pro-Kumamolisin to about 400 milligrams (mg) of pro-Kumamolisin, about 50 milligrams (mg) of pro-Kumamolisin to about 500 milligrams (mg) of pro-Kumamolisin, about 50 milligrams (mg) of pro-Kumamolisin to about 750 milligrams (mg) of pro-Kumamolisin, about 50 milligrams (mg) of pro-Kumamolisin to about 1,000 milligrams (mg) of pro-Kumamolisin, about 50 milligrams (mg) of pro-Kumamolisin to about 1,250 milligrams (mg) of pro-Kumamolisin, about 50 milligrams (mg) of pro-Kumamolisin to about 1,500 milligrams (mg) of pro-Kumamolisin, about 50 milligrams (mg) of pro-Kumamolisin to about 2,000 milligrams (mg) of pro-Kumamolisin, about 100 milligrams (mg) of pro-Kumamolisin to about 200 milligrams (mg) of pro-Kumamolisin, about 100 milligrams (mg) of pro-Kumamolisin to about 300 milligrams (mg) of pro-Kumamolisin, about 100 milligrams (mg) of pro-Kumamolisin to about 400 milligrams (mg) of pro-Kumamolisin, about 100 milligrams (mg) of pro-Kumamolisin to about 500 milligrams (mg) of pro-Kumamolisin, about 100 milligrams (mg) of pro-Kumamolisin to about 750 milligrams (mg) of pro-Kumamolisin, about 100 milligrams (mg) of pro-Kumamolisin to about 1,000 milligrams (mg) of pro-Kumamolisin, about 100 milligrams (mg) of pro-Kumamolisin to about 1,250 milligrams (mg) of pro-Kumamolisin, about 100 milligrams (mg) of pro-Kumamolisin to about 1,500 milligrams (mg) of pro-Kumamolisin, about 100 milligrams (mg) of pro-Kumamolisin to about 2,000 milligrams (mg) of pro-Kumamolisin, about 200 milligrams (mg) of pro-Kumamolisin to about 300 milligrams (mg) of pro-Kumamolisin, about 200 milligrams (mg) of pro-Kumamolisin to about 400 milligrams (mg) of pro-Kumamolisin, about 200 milligrams (mg) of pro-Kumamolisin to about 500 milligrams (mg) of pro-Kumamolisin, about 200 milligrams (mg) of pro-Kumamolisin to about 750 milligrams (mg) of pro-Kumamolisin, about 200 milligrams (mg) of pro-Kumamolisin to about 1,000 milligrams (mg) of pro-Kumamolisin, about 200 milligrams (mg) of pro-Kumamolisin to about 1,250 milligrams (mg) of pro-Kumamolisin, about 200 milligrams (mg) of pro-Kumamolisin to about 1,500 milligrams (mg) of pro-Kumamolisin, about 200 milligrams (mg) of pro-Kumamolisin to about 2,000 milligrams (mg) of pro-Kumamolisin, about 300 milligrams (mg) of pro-Kumamolisin to about 400 milligrams (mg) of pro-Kumamolisin, about 300 milligrams (mg) of pro-Kumamolisin to about 500 milligrams (mg) of pro-Kumamolisin, about 300 milligrams (mg) of pro-Kumamolisin to about 750 milligrams (mg) of pro-Kumamolisin, about 300 milligrams (mg) of pro-Kumamolisin to about 1,000 milligrams (mg) of pro-Kumamolisin, about 300 milligrams (mg) of pro-Kumamolisin to about 1,250 milligrams (mg) of pro-Kumamolisin, about 300 milligrams (mg) of pro-Kumamolisin to about 1,500 milligrams (mg) of pro-Kumamolisin, about 300 milligrams (mg) of pro-Kumamolisin to about 2,000 milligrams (mg) of pro-Kumamolisin, about 400 milligrams (mg) of pro-Kumamolisin to about 500 milligrams (mg) of pro-Kumamolisin, about 400 milligrams (mg) of pro-Kumamolisin to about 750 milligrams (mg) of pro-Kumamolisin, about 400 milligrams (mg) of pro-Kumamolisin to about 1,000 milligrams (mg) of pro-Kumamolisin, about 400 milligrams (mg) of pro-Kumamolisin to about 1,250 milligrams (mg) of pro-Kumamolisin, about 400 milligrams (mg) of pro-Kumamolisin to about 1,500 milligrams (mg) of pro-Kumamolisin, about 400 milligrams (mg) of pro-Kumamolisin to about 2,000 milligrams (mg) of pro-Kumamolisin, about 500 milligrams (mg) of pro-Kumamolisin to about 750 milligrams (mg) of pro-Kumamolisin, about 500 milligrams (mg) of pro-Kumamolisin to about 1,000 milligrams (mg) of pro-Kumamolisin, about 500 milligrams (mg) of pro-Kumamolisin to about 1,250 milligrams (mg) of pro-Kumamolisin, about 500 milligrams (mg) of pro-Kumamolisin to about 1,500 milligrams (mg) of pro-Kumamolisin, about 500 milligrams (mg) of pro-Kumamolisin to about 2,000 milligrams (mg) of pro-Kumamolisin, about 750 milligrams (mg) of pro-Kumamolisin to about 1,000 milligrams (mg) of pro-Kumamolisin, about 750 milligrams (mg) of pro-Kumamolisin to about 1,250 milligrams (mg) of pro-Kumamolisin, about 750 milligrams (mg) of pro-Kumamolisin to about 1,500 milligrams (mg) of pro-Kumamolisin, about 750 milligrams (mg) of pro-Kumamolisin to about 2,000 milligrams (mg) of pro-Kumamolisin, about 1,000 milligrams (mg) of pro-Kumamolisin to about 1,250 milligrams (mg) of pro-Kumamolisin, about 1,000 milligrams (mg) of pro-Kumamolisin to about 1,500 milligrams (mg) of pro-Kumamolisin, about 1,000 milligrams (mg) of pro-Kumamolisin to about 2,000 milligrams (mg) of pro-Kumamolisin, about 1,250 milligrams (mg) of pro-Kumamolisin to about 1,500 milligrams (mg) of pro-Kumamolisin, about 1,250 milligrams (mg) of pro-Kumamolisin to about 2,000 milligrams (mg) of pro-Kumamolisin, or about 1,500 milligrams (mg) of pro-Kumamolisin to about 2,000 milligrams (mg) of pro-Kumamolisin. In some embodiments, composition comprises about 50 milligrams (mg) of pro-Kumamolisin, about 100 milligrams (mg) of pro-Kumamolisin, about 200 milligrams (mg) of pro-Kumamolisin, about 300 milligrams (mg) of pro-Kumamolisin, about 400 milligrams (mg) of pro-Kumamolisin, about 500 milligrams (mg) of pro-Kumamolisin, about 750 milligrams (mg) of pro-Kumamolisin, about 1,000 milligrams (mg) of pro-Kumamolisin, about 1,250 milligrams (mg) of pro-Kumamolisin, about 1,500 milligrams (mg) of pro-Kumamolisin, or about 2,000 milligrams (mg) of pro-Kumamolisin. In some embodiments, composition comprises at least about 50 milligrams (mg) of pro-Kumamolisin, about 100 milligrams (mg) of pro-Kumamolisin, about 200 milligrams (mg) of pro-Kumamolisin, about 300 milligrams (mg) of pro-Kumamolisin, about 400 milligrams (mg) of pro-Kumamolisin, about 500 milligrams (mg) of pro-Kumamolisin, about 750 milligrams (mg) of pro-Kumamolisin, about 1,000 milligrams (mg) of pro-Kumamolisin, about 1,250 milligrams (mg) of pro-Kumamolisin, or about 1,500 milligrams (mg) of pro-Kumamolisin. In some embodiments, composition comprises at most about 100 milligrams (mg) of pro-Kumamolisin, about 200 milligrams (mg) of pro-Kumamolisin, about 300 milligrams (mg) of pro-Kumamolisin, about 400 milligrams (mg) of pro-Kumamolisin, about 500 milligrams (mg) of pro-Kumamolisin, about 750 milligrams (mg) of pro-Kumamolisin, about 1,000 milligrams (mg) of pro- Kumamolisin, about 1,250 milligrams (mg) of pro-Kumamolisin, about 1,500 milligrams (mg) of pro-Kumamolisin, or about 2,000 milligrams (mg) of pro-Kumamolisin.

Methods

As described herein, in certain instances, providing a legume protein (e.g., pea protein) and an S53 protease (e.g., a pro-Kumamolisin) protease lowers (e.g., decreases or reduces) blood sugar levels. Accordingly, provided herein are methods of decreasing blood glucose in a subject, comprising: administering to the subject a composition comprising: a legume protein and an S53 protease (e.g., pro-Kumamolisin). (e.g., wherein the legume protein and the S53 protease (e.g., pro-Kumamolisin) is administered to the subject). Further provided is a legume protein and an S53 protease (e.g., pro-Kumamolisin) for use in a method of decreasing blood glucose in a subject (e.g., wherein the legume protein and the S53 protease (e.g., pro-Kumamolisin) is administered to the subject).

Also provided are methods of reducing an increase in blood glucose in a subject, comprising: administering to the subject a composition comprising a legume protein and an S53 protease (e.g., pro-Kumamolisin). Further provided is the use of a legume protein and an S53 protease (e.g., pro-Kumamolisin) in a method of reducing an increase in blood glucose in a subject (e.g., wherein the legume protein and the S53 protease (e.g., pro-Kumamolisin) is administered to the subject). Furthermore, also provided is a legume protein and an S53 protease (e.g., pro-Kumamolisin) for use in a method of reducing an increase in blood glucose in a subject (e.g., wherein the legume protein and the S53 protease (e.g., pro-Kumamolisin) is administered to the subject).

In certain instances, providing a legume protein (e.g., pea protein) and an S53 protease (e.g., pro-Kumamolisin) stabilizes (e.g., reducing or preventing the extent or degree of change) blood sugar levels associated with the intake of a foodstuff. In some embodiments, provided herein are methods of reducing a change (positive or negative) in blood glucose in a subject, comprising: administering to the subject a composition comprising: a legume protein and an S53 protease (e.g., pro-Kumamolisin) (e.g., wherein the legume protein and the S53 protease (e.g., pro-Kumamolisin) is administered to the subject).

In certain embodiments, administering the legume protein and the S53 protease (e.g., pro-Kumamolisin) reduces the degree or amount of an increase in blood glucose upon intake of a foodstuff. In certain instances, reducing the degree or amount of increase in blood glucose upon intake of a foodstuff can be compared to an increase in blood glucose upon intake of a foodstuff prior to or without administering the legume protein and the S53 protease (e.g., pro-Kumamolisin). In certain embodiments, administering the legume protein and an S53 protease (e.g., pro-Kumamolisin) reduces the degree or amount of decrease in blood glucose upon intake of a foodstuff. In certain instances, reducing the degree or amount of decrease in blood glucose upon intake of a foodstuff can be compared to a decrease in blood glucose upon intake of a foodstuff prior to or without administering the legume protein and the S53 protease (e.g., pro-Kumamolisin). In some embodiments, administering the legume protein and the S53 protease (e.g., pro-Kumamolisin) reduces a change (e.g., increase or decrease) in blood glucose upon intake of a foodstuff. In certain embodiments, reducing a change (e.g., increase or decrease) in blood glucose upon intake of a foodstuff when the legume protein and the S53 protease (e.g., pro-Kumamolisin) is administered is be compared to change in blood glucose upon intake of a foodstuff prior to or without administering the legume protein and/or the S53 protease (e.g., pro-Kumamolisin).

In some embodiments, the S53 protease comprises an amino acid sequence as set forth in SEQ ID NO: 1. In some embodiments, the S53 protease comprises an amino acid sequence having equal to or greater than 80% sequence identity to SEQ ID NO: 1. In some embodiments, the S53 protease comprises an amino acid sequence having equal to or greater than 85% sequence identity to SEQ ID NO: 1. In some embodiments, the S53 protease comprises an amino acid sequence having equal to or greater than 90% sequence identity to SEQ ID NO: 1. In some embodiments, the S53 protease comprises an amino acid sequence having equal to or greater than 95% sequence identity to SEQ ID NO: 1. In some embodiments, the S53 protease comprises an amino acid sequence having equal to or greater than 97% sequence identity to SEQ ID NO: 1. In some embodiments, the S53 protease comprises an amino acid sequence having equal to or greater than 98% sequence identity to SEQ ID NO: 1. In some embodiments, the S53 protease comprises an amino acid sequence having equal to or greater than 99% sequence identity to SEQ ID NO: 1.

In some embodiments, the S53 protease comprises an amino acid sequence as set forth in SEQ ID NO: 2. In some embodiments, the S53 protease comprises an amino acid sequence having equal to or greater than 80% sequence identity to SEQ ID NO: 2. In some embodiments, the S53 protease comprises an amino acid sequence having equal to or greater than 85% sequence identity to SEQ ID NO: 2. In some embodiments, the S53 protease comprises an amino acid sequence having equal to or greater than 90% sequence identity to SEQ ID NO: 2. In some embodiments, the S53 protease comprises an amino acid sequence having equal to or greater than 95% sequence identity to SEQ ID NO: 2. In some embodiments, the S53 protease comprises an amino acid sequence having equal to or greater than 97% sequence identity to SEQ ID NO: 2. In some embodiments, the S53 protease comprises an amino acid sequence having equal to or greater than 98% sequence identity to SEQ ID NO: 2. In some embodiments, the S53 protease comprises an amino acid sequence having equal to or greater than 99% sequence identity to SEQ ID NO: 2.

In some embodiments, the S53 protease comprises an amino acid sequence as set forth in SEQ ID NO: 3. In some embodiments, the S53 protease comprises an amino acid sequence having equal to or greater than 80% sequence identity to SEQ ID NO: 3. In some embodiments, the S53 protease comprises an amino acid sequence having equal to or greater than 85% sequence identity to SEQ ID NO: 3. In some embodiments, the S53 protease comprises an amino acid sequence having equal to or greater than 90% sequence identity to SEQ ID NO: 3. In some embodiments, the S53 protease comprises an amino acid sequence having equal to or greater than 95% sequence identity to SEQ ID NO: 3. In some embodiments, the S53 protease comprises an amino acid sequence having equal to or greater than 97% sequence identity to SEQ ID NO: 3. In some embodiments, the S53 protease comprises an amino acid sequence having equal to or greater than 98% sequence identity to SEQ ID NO: 3. In some embodiments, the S53 protease comprises an amino acid sequence having equal to or greater than 99% sequence identity to SEQ ID NO: 3.

In some embodiments, the S53 protease comprises an amino acid sequence as set forth in SEQ ID NO: 4. In some embodiments, the S53 protease comprises an amino acid sequence having equal to or greater than 80% sequence identity to SEQ ID NO: 4. In some embodiments, the S53 protease comprises an amino acid sequence having equal to or greater than 85% sequence identity to SEQ ID NO: 4. In some embodiments, the S53 protease comprises an amino acid sequence having equal to or greater than 90% sequence identity to SEQ ID NO: 4. In some embodiments, a pro-Kumamolisin comprises an amino acid sequence having equal to or greater than 95% sequence identity to SEQ ID NO: 4. In some embodiments, the S53 protease comprises an amino acid sequence having equal to or greater than 97% sequence identity to SEQ ID NO: 4. In some embodiments, the S53 protease comprises an amino acid sequence having equal to or greater than 98% sequence identity to SEQ ID NO: 4. In some embodiments, the S53 protease comprises an amino acid sequence having equal to or greater than 99% sequence identity to SEQ ID NO: 4.

In some embodiments, the S53 protease comprises an amino acid sequence as set forth in SEQ ID NO: 5. In some embodiments, the S53 protease comprises an amino acid sequence having equal to or greater than 80% sequence identity to SEQ ID NO: 5. In some embodiments, the S53 protease comprises an amino acid sequence having equal to or greater than 85% sequence identity to SEQ ID NO: 5. In some embodiments, the S53 protease comprises an amino acid sequence having equal to or greater than 90% sequence identity to SEQ ID NO: 5. In some embodiments, the S53 protease comprises an amino acid sequence having equal to or greater than 95% sequence identity to SEQ ID NO: 5. In some embodiments, the S53 protease comprises an amino acid sequence having equal to or greater than 97% sequence identity to SEQ ID NO: 5. In some embodiments, the S53 protease comprises an amino acid sequence having equal to or greater than 98% sequence identity to SEQ ID NO: 5. In some embodiments, the S53 protease comprises an amino acid sequence having equal to or greater than 99% sequence identity to SEQ ID NO: 5.

In some embodiments, the S53 protease comprises an amino acid sequence as set forth in SEQ ID NO: 6. In some embodiments, the S53 protease comprises an amino acid sequence having equal to or greater than 80% sequence identity to SEQ ID NO: 6. In some embodiments, the S53 protease comprises an amino acid sequence having equal to or greater than 85% sequence identity to SEQ ID NO: 6. In some embodiments, the S53 protease comprises an amino acid sequence having equal to or greater than 90% sequence identity to SEQ ID NO: 6. In some embodiments, the S53 protease comprises an amino acid sequence having equal to or greater than 95% sequence identity to SEQ ID NO: 6. In some embodiments, the S53 protease comprises an amino acid sequence having equal to or greater than 97% sequence identity to SEQ ID NO: 6. In some embodiments, the S53 protease comprises an amino acid sequence having equal to or greater than 98% sequence identity to SEQ ID NO: 6. In some embodiments, the S53 protease comprises an amino acid sequence having equal to or greater than 99% sequence identity to SEQ ID NO: 6.

In some embodiments, the S53 protease comprises an amino acid sequence as set forth in SEQ ID NO: 7. In some embodiments, the S53 protease comprises an amino acid sequence having equal to or greater than 80% sequence identity to SEQ ID NO: 7. In some embodiments, the S53 protease comprises an amino acid sequence having equal to or greater than 85% sequence identity to SEQ ID NO: 7. In some embodiments, the S53 protease comprises an amino acid sequence having equal to or greater than 90% sequence identity to SEQ ID NO: 7. In some embodiments, the S53 protease comprises an amino acid sequence having equal to or greater than 95% sequence identity to SEQ ID NO: 7. In some embodiments, the S53 protease comprises an amino acid sequence having equal to or greater than 97% sequence identity to SEQ ID NO: 7. In some embodiments, the S53 protease comprises an amino acid sequence having equal to or greater than 98% sequence identity to SEQ ID NO: 7. In some embodiments, the S53 protease comprises an amino acid sequence having equal to or greater than 99% sequence identity to SEQ ID NO: 7.

In some embodiments, the S53 protease comprises an amino acid sequence as set forth in SEQ ID NO: 8. In some embodiments, the S53 protease comprises an amino acid sequence having equal to or greater than 80% sequence identity to SEQ ID NO: 8. In some embodiments, the S53 protease comprises an amino acid sequence having equal to or greater than 85% sequence identity to SEQ ID NO: 8. In some embodiments, the S53 protease comprises an amino acid sequence having equal to or greater than 90% sequence identity to SEQ ID NO: 8. In some embodiments, the S53 protease comprises an amino acid sequence having equal to or greater than 95% sequence identity to SEQ ID NO: 8. In some embodiments, the S53 protease comprises an amino acid sequence having equal to or greater than 97% sequence identity to SEQ ID NO: 8. In some embodiments, the S53 protease comprises an amino acid sequence having equal to or greater than 98% sequence identity to SEQ ID NO: 8. In some embodiments, the S53 protease comprises an amino acid sequence having equal to or greater than 99% sequence identity to SEQ ID NO: 8.

In some embodiments, the S53 protease comprises an amino acid sequence as set forth in SEQ ID NO: 9. In some embodiments, the S53 protease comprises an amino acid sequence having equal to or greater than 80% sequence identity to SEQ ID NO: 9. In some embodiments, the S53 protease comprises an amino acid sequence having equal to or greater than 85% sequence identity to SEQ ID NO: 9. In some embodiments, the S53 protease comprises an amino acid sequence having equal to or greater than 90% sequence identity to SEQ ID NO: 9. In some embodiments, the S53 protease comprises an amino acid sequence having equal to or greater than 95% sequence identity to SEQ ID NO: 9. In some embodiments, the S53 protease comprises an amino acid sequence having equal to or greater than 97% sequence identity to SEQ ID NO: 9. In some embodiments, the S53 protease comprises an amino acid sequence having equal to or greater than 98% sequence identity to SEQ ID NO: 9. In some embodiments, the S53 protease comprises an amino acid sequence having equal to or greater than 99% sequence identity to SEQ ID NO: 9.

In some embodiments, the S53 protease comprises an amino acid sequence as set forth in SEQ ID NO: 10. In some embodiments, the S53 protease comprises an amino acid sequence having equal to or greater than 80% sequence identity to SEQ ID NO: 10. In some embodiments, the S53 protease comprises an amino acid sequence having equal to or greater than 85% sequence identity to SEQ ID NO: 10. In some embodiments, the S53 protease comprises an amino acid sequence having equal to or greater than 90% sequence identity to SEQ ID NO: 10. In some embodiments, the S53 protease comprises an amino acid sequence having equal to or greater than 95% sequence identity to SEQ ID NO: 10. In some embodiments, the S53 protease comprises an amino acid sequence having equal to or greater than 97% sequence identity to SEQ ID NO: 10. In some embodiments, the S53 protease comprises an amino acid sequence having equal to or greater than 98% sequence identity to SEQ ID NO: 10. In some embodiments, the S53 protease comprises an amino acid sequence having equal to or greater than 99% sequence identity to SEQ ID NO: 10.

In some embodiments, the S53 protease comprises an amino acid sequence as set forth in SEQ ID NO: 11. In some embodiments, the S53 protease comprises an amino acid sequence having equal to or greater than 80% sequence identity to SEQ ID NO: 11. In some embodiments, the S53 protease comprises an amino acid sequence having equal to or greater than 85% sequence identity to SEQ ID NO: 11. In some embodiments, the S53 protease comprises an amino acid sequence having equal to or greater than 90% sequence identity to SEQ ID NO: 11. In some embodiments, the S53 protease comprises an amino acid sequence having equal to or greater than 95% sequence identity to SEQ ID NO: 11. In some embodiments, the S53 protease comprises an amino acid sequence having equal to or greater than 97% sequence identity to SEQ ID NO: 11. In some embodiments, the S53 protease comprises an amino acid sequence having equal to or greater than 98% sequence identity to SEQ ID NO: 11. In some embodiments, the S53 protease comprises an amino acid sequence having equal to or greater than 99% sequence identity to SEQ ID NO: 11.

In some embodiments, the active site of the S53 protease comprises amino acid residues E266, F295 or A295, S316, W317, G318, A349, A350 or S350, G351, D352, S353 or D353 or A353 or N353, D367 or E367, G462, G463, T464, S465, and A466 of SEQ ID NO:1.

Any of the S53 proteases (e.g., pro-Kumamolisin) described herein can be used in the methods provided. In some embodiments, the S53 protease (e.g., pro-Kumamolisin) comprises an amino acid sequence having at least 85% sequence identity to SEQ ID NO: 1. In some embodiments, the S53 protease (e.g., pro-Kumamolisin) comprises an amino acid sequence having at least 95% sequence identity to SEQ ID NO: 1. In some embodiments, the S53 protease (e.g., pro-Kumamolisin) comprises an amino acid sequence having at least 98% sequence identity to SEQ ID NO: 1.

In some embodiments, the S53 protease (e.g., pro-Kumamolisin) comprises an amino acid sequence of SEQ ID NO: 1. In some embodiments, the S53 protease (e.g., pro-Kumamolisin) comprises an active site comprising amino acid residues E266, F295, S316, W317, G318, A349, A350, G351, D352, S353, D367, G462, G463, T464, S465, and A466 of SEQ ID NO:1. In some embodiments, the S53 protease (e.g., pro-Kumamolisin) comprises an active site comprising one or more amino acid substitutions of residues E266, F295, S316, W317, G318, A349, A350, G351, D352, S353, D367, G462, G463, T464, S465, and A466 of SEQ ID NO:1. In some embodiments, the active site comprises between one and five amino acid substitutions. In some embodiments, the S53 protease (e.g., pro-Kumamolisin) comprises one or more truncations of SEQ ID NO:1, wherein the one or more truncations comprises an N-terminal truncation, a C-terminal truncation, or both an N-terminal and C-terminal truncation.

In some embodiments, the amount of S53 protease (e.g., pro-Kumamolisin) administered comprises about 50 milligrams (mg) to about 1,500 milligrams (mg). In some embodiments, the amount of S53 protease (e.g., pro-Kumamolisin) administered comprises about 50 milligrams (mg) to about 100 milligrams (mg), about 50 milligrams (mg) to about 150 milligrams (mg), about 50 milligrams (mg) to about 200 milligrams (mg), about 50 milligrams (mg) to about 300 milligrams (mg), about 50 milligrams (mg) to about 400 milligrams (mg), about 50 milligrams (mg) to about 500 milligrams (mg), about 50 milligrams (mg) to about 750 milligrams (mg), about 50 milligrams (mg) to about 1,000 milligrams (mg), about 50 milligrams (mg) to about 1,500 milligrams (mg), about 100 milligrams (mg) to about 150 milligrams (mg), about 100 milligrams (mg) to about 200 milligrams (mg), about 100 milligrams (mg) to about 300 milligrams (mg), about 100 milligrams (mg) to about 400 milligrams (mg), about 100 milligrams (mg) to about 500 milligrams (mg), about 100 milligrams (mg) to about 750 milligrams (mg), about 100 milligrams (mg) to about 1,000 milligrams (mg), about 100 milligrams (mg) to about 1,500 milligrams (mg), about 150 milligrams (mg) to about 200 milligrams (mg), about 150 milligrams (mg) to about 300 milligrams (mg), about 150 milligrams (mg) to about 400 milligrams (mg), about 150 milligrams (mg) to about 500 milligrams (mg), about 150 milligrams (mg) to about 750 milligrams (mg), about 150 milligrams (mg) to about 1,000 milligrams (mg), about 150 milligrams (mg) to about 1,500 milligrams (mg), about 200 milligrams (mg) to about 300 milligrams (mg), about 200 milligrams (mg) to about 400 milligrams (mg), about 200 milligrams (mg) to about 500 milligrams (mg), about 200 milligrams (mg) to about 750 milligrams (mg), about 200 milligrams (mg) to about 1,000 milligrams (mg), about 200 milligrams (mg) to about 1,500 milligrams (mg), about 300 milligrams (mg) to about 400 milligrams (mg), about 300 milligrams (mg) to about 500 milligrams (mg), about 300 milligrams (mg) to about 750 milligrams (mg), about 300 milligrams (mg) to about 1,000 milligrams (mg), about 300 milligrams (mg) to about 1,500 milligrams (mg), about 400 milligrams (mg) to about 500 milligrams (mg), about 400 milligrams (mg) to about 750 milligrams (mg), about 400 milligrams (mg) to about 1,000 milligrams (mg), about 500 milligrams (mg) to about 1,500 milligrams (mg), about 500 milligrams (mg) to about 750 milligrams (mg), about 500 milligrams (mg) to about 1,000 milligrams (mg), about 750 milligrams (mg) to about 1,500 milligrams (mg), about 750 milligrams (mg) to about 1,000 milligrams (mg), or about 1,000 milligrams (mg) to about 1,500 milligrams (mg). In some embodiments, the amount of S53 protease (e.g., pro-Kumamolisin) administered comprises about 50 milligrams (mg), about 100 milligrams (mg), about 150 milligrams (mg), about 200 milligrams (mg), about 300 milligrams (mg), about 400 milligrams (mg), about 500 milligrams (mg), about 750 milligrams (mg), about 1,000 milligrams (mg), or about 1,500 milligrams (mg). In some embodiments, the amount of S53 protease (e.g., pro-Kumamolisin) administered comprises at least about 50 milligrams (mg), about 100 milligrams (mg), about 150 milligrams (mg), about 200 milligrams (mg), about 300 milligrams (mg), about 400 milligrams (mg), about 500 milligrams (mg), about 750 milligrams (mg), or about 1,000 milligrams (mg). In some embodiments, the amount of S53 protease (e.g., pro-Kumamolisin) administered comprises at most about 100 milligrams (mg), about 150 milligrams (mg), about 200 milligrams (mg), about 300 milligrams (mg), about 400 milligrams (mg), about 500 milligrams (mg), about 750 milligrams (mg), about 1,000 milligrams (mg), or about 1,500 milligrams (mg).

In some embodiments, the amount of legume protein administered comprises about 5 grams (g) to about 50 grams (g). In some embodiments, the amount of legume protein administered comprises about 5 grams (g) to about 10 grams (g), about 5 grams (g) to about 15 grams (g), about 5 grams (g) to about 20 grams (g), about 5 grams (g) to about 25 grams (g), about 5 grams (g) to about 30 grams (g), about 5 grams (g) to about 35 grams (g), about 5 grams (g) to about 40 grams (g), about 5 grams (g) to about 45 grams (g), about 5 grams (g) to about 50 grams (g), about 10 grams (g) to about 15 grams (g), about 10 grams (g) to about 20 grams (g), about 10 grams (g) to about 25 grams (g), about 10 grams (g) to about 30 grams (g), about 10 grams (g) to about 35 grams (g), about 10 grams (g) to about 40 grams (g), about 10 grams (g) to about 45 grams (g), about 10 grams (g) to about 50 grams (g), about 15 grams (g) to about 20 grams (g), about 15 grams (g) to about 25 grams (g), about 15 grams (g) to about 30 grams (g), about 15 grams (g) to about 35 grams (g), about 15 grams (g) to about 40 grams (g), about 15 grams (g) to about 45 grams (g), about 15 grams (g) to about 50 grams (g), about 20 grams (g) to about 25 grams (g), about 20 grams (g) to about 30 grams (g), about 20 grams (g) to about 35 grams (g), about 20 grams (g) to about 40 grams (g), about 20 grams (g) to about 45 grams (g), about 20 grams (g) to about 50 grams (g), about 25 grams (g) to about 30 grams (g), about 25 grams (g) to about 35 grams (g), about 25 grams (g) to about 40 grams (g), about 25 grams (g) to about 45 grams (g), about 25 grams (g) to about 50 grams (g), about 30 grams (g) to about 35 grams (g), about 30 grams (g) to about 40 grams (g), about 30 grams (g) to about 45 grams (g), about 30 grams (g) to about 50 grams (g), about 35 grams (g) to about 40 grams (g), about 35 grams (g) to about 45 grams (g), about 35 grams (g) to about 50 grams (g), about 40 grams (g) to about 45 grams (g), about 40 grams (g) to about 50 grams (g), or about 45 grams (g) to about 50 grams (g). In some embodiments, the amount of legume protein administered comprises about 5 grams (g), about 10 grams (g), about 15 grams (g), about 20 grams (g), about 25 grams (g), about 30 grams (g), about 35 grams (g), about 40 grams (g), about 45 grams (g), or about 50 grams (g). In some embodiments, the amount of legume protein administered comprises at least about 5 grams (g), about 10 grams (g), about 15 grams (g), about 20 grams (g), about 25 grams (g), about 30 grams (g), about 35 grams (g), about 40 grams (g), or about 45 grams (g). In some embodiments, the amount of legume protein administered comprises at most about 10 grams (g), about 15 grams (g), about 20 grams (g), about 25 grams (g), about 30 grams (g), about 35 grams (g), about 40 grams (g), about 45 grams (g), or about 50 grams (g).

In some embodiments, the legume protein is a pea protein. In some embodiments, the pea is a whole pea or a component thereof. In certain embodiments, the pea is a garden pea, a sugar pea, a field pea, or any combination thereof. In certain embodiments, the pea is a garden pea. In certain embodiments, the pea is a sugar pea. In certain embodiments, the pea is a field pea. In certain embodiments, the pea is any combination of a garden pea, a sugar pea, and/or a field pea. In some embodiments, the pea is a standard pea, a commoditized pea, a genetically modified pea, or a combination thereof. In certain embodiments, the pea is a smooth pea, a wrinkled pea, or a combination thereof.

In some embodiments, a composition comprising the legume protein is administered. In some embodiments, a composition comprising the S53 protease (e.g., pro-Kumamolisin) is administered. In some embodiments, a composition comprising the legume protein and the S53 protease (e.g., pro-Kumamolisin) is administered.

In some embodiments, the administering occurs after the subject ingests a foodstuff comprising sugar. In some embodiments, the sugar comprises of sucrose, lactose, maltose, or another di-, tri-, or polysaccharides that contain glucose as a monomer. In certain embodiments, the sugar comprises sucrose. In certain embodiments, the sugar comprises lactose. In certain embodiments, the sugar comprises maltose. In certain embodiments, the sugar comprises di-, tri-, or polysaccharides that contain glucose as a monomer.

In some embodiments, the increase in blood sugar is reduced relative to administering a composition that does not comprise the S53 protease (e.g., pro-Kumamolisin). In some embodiments, the subject self-administers the composition. In some embodiments, the subject is a mammal. In some embodiments, the mammal is a human. In some embodiments, the human has hyperglycemia. In some embodiments, the human has a condition associated with and/or caused by hyperglycemia. In some embodiments, the condition is cardiovascular disease or neuropathy or diabetic nephropathy or retinopathy or cataract or bone and joint problems or teeth and gum infections. In certain embodiments, the condition is cardiovascular disease. In certain embodiments, the condition is a neuropathy. In certain embodiments, the condition is diabetic nephropathy. In certain embodiments, the condition is retinopathy. In certain embodiments, the condition is cataract. In certain embodiments, the condition is bone and joint problems. In certain embodiments, the condition is a tooth infection. In certain embodiments, the condition is a gum infection.

Further provided are methods of reducing the glycemic index of a foodstuff, comprising: providing a legume protein and an S53 protease (e.g., pro-Kumamolisin) to the foodstuff. Further provided is the use of a legume protein and an S53 protease (e.g., pro-Kumamolisin) to reduce the glycemic index of a foodstuff. Furthermore, also provided is a legume protein and an S53 protease (e.g., pro-Kumamolisin) for use in reducing the glycemic index of a foodstuff.

Any of the S53 proteases (e.g., pro-Kumamolisin) described herein can be used in the methods provided. In some embodiments, the S53 protease (e.g., pro-Kumamolisin) comprises an amino acid sequence having at least 85% sequence identity to any one of SEQ ID NOs: 1 and 3-11. In some embodiments, the S53 protease (e.g., pro-Kumamolisin) comprises an amino acid sequence having at least 95% sequence identity to any one of SEQ ID NOs: 1 and 3-11. In some embodiments, the S53 protease (e.g., pro-Kumamolisin) comprises an amino acid sequence having at least 98% sequence identity to any one of SEQ ID NOs: 1 and 3-11. In some embodiments, the active site of the S53 protease comprises amino acid residues E266, F295 or A295, S316, W317, G318, A349, A350 or S350, G351, D352, S353 or D353 or A353 or N353, D367 or E367, G462, G463, T464, S465, and A466 of SEQ ID NO:1.

In some embodiments, the S53 protease (e.g., pro-Kumamolisin) comprises an amino acid sequence of SEQ ID NO: 1. In some embodiments, the S53 protease (e.g., pro-Kumamolisin) comprises an active site comprising amino acid residues E266, F295, S316, W317, G318, A349, A350, G351, D352, S353, D367, G462, G463, T464, S465, and A466 of SEQ ID NO:1. In some embodiments, the S53 protease (e.g., pro-Kumamolisin) comprises an active site comprising one or more amino acid substitutions of residues E266, F295, S316, W317, G318, A349, A350, G351, D352, S353, D367, G462, G463, T464, S465, and A466 of SEQ ID NO:1. In some embodiments, the active site comprises between one and five amino acid substitutions. In some embodiments, the S53 protease (e.g., pro-Kumamolisin) comprises one or more truncations of SEQ ID NO:1, wherein the one or more truncations comprises an N-terminal truncation, a C-terminal truncation, or both an N-terminal and C-terminal truncation.

In some embodiments, the provided amount of pro-Kumamolisin administered comprises about 50 milligrams (mg) to about 1,500 milligrams (mg). In some embodiments, the provided amount of pro-Kumamolisin administered comprises about 50 milligrams (mg) to about 100 milligrams (mg), about 50 milligrams (mg) to about 150 milligrams (mg), about 50 milligrams (mg) to about 200 milligrams (mg), about 50 milligrams (mg) to about 300 milligrams (mg), about 50 milligrams (mg) to about 400 milligrams (mg), about 50 milligrams (mg) to about 500 milligrams (mg), about 50 milligrams (mg) to about 750 milligrams (mg), about 50 milligrams (mg) to about 1,000 milligrams (mg), about 50 milligrams (mg) to about 1,500 milligrams (mg), about 100 milligrams (mg) to about 150 milligrams (mg), about 100 milligrams (mg) to about 200 milligrams (mg), about 100 milligrams (mg) to about 300 milligrams (mg), about 100 milligrams (mg) to about 400 milligrams (mg), about 100 milligrams (mg) to about 500 milligrams (mg), about 100 milligrams (mg) to about 750 milligrams (mg), about 100 milligrams (mg) to about 1,000 milligrams (mg), about 100 milligrams (mg) to about 1,500 milligrams (mg), about 150 milligrams (mg) to about 200 milligrams (mg), about 150 milligrams (mg) to about 300 milligrams (mg), about 150 milligrams (mg) to about 400 milligrams (mg), about 150 milligrams (mg) to about 500 milligrams (mg), about 150 milligrams (mg) to about 750 milligrams (mg), about 150 milligrams (mg) to about 1,000 milligrams (mg), about 150 milligrams (mg) to about 1,500 milligrams (mg), about 200 milligrams (mg) to about 300 milligrams (mg), about 200 milligrams (mg) to about 400 milligrams (mg), about 200 milligrams (mg) to about 500 milligrams (mg), about 200 milligrams (mg) to about 750 milligrams (mg), about 200 milligrams (mg) to about 1,000 milligrams (mg), about 200 milligrams (mg) to about 1,500 milligrams (mg), about 300 milligrams (mg) to about 400 milligrams (mg), about 300 milligrams (mg) to about 500 milligrams (mg), about 300 milligrams (mg) to about 750 milligrams (mg), about 300 milligrams (mg) to about 1,000 milligrams (mg), about 300 milligrams (mg) to about 1,500 milligrams (mg), about 400 milligrams (mg) to about 500 milligrams (mg), about 400 milligrams (mg) to about 750 milligrams (mg), about 400 milligrams (mg) to about 1,000 milligrams (mg), about 400 milligrams (mg) to about 1,500 milligrams (mg), about 500 milligrams (mg) to about 750 milligrams (mg), about 500 milligrams (mg) to about 1,000 milligrams (mg), about 500 milligrams (mg) to about 1,500 milligrams (mg), about 750 milligrams (mg) to about 1,000 milligrams (mg), about 750 milligrams (mg) to about 1,500 milligrams (mg), or about 1,000 milligrams (mg) to about 1,500 milligrams (mg). In some embodiments, the provided amount of pro-Kumamolisin administered comprises about 50 milligrams (mg), about 100 milligrams (mg), about 150 milligrams (mg), about 200 milligrams (mg), about 300 milligrams (mg), about 400 milligrams (mg), about 500 milligrams (mg), about 750 milligrams (mg), about 1,000 milligrams (mg), or about 1,500 milligrams (mg). In some embodiments, the provided amount of pro-Kumamolisin administered comprises at least about 50 milligrams (mg), about 100 milligrams (mg), about 150 milligrams (mg), about 200 milligrams (mg), about 300 milligrams (mg), about 400 milligrams (mg), about 500 milligrams (mg), about 750 milligrams (mg), or about 1,000 milligrams (mg). In some embodiments, the provided amount of pro-Kumamolisin administered comprises at most about 100 milligrams (mg), about 150 milligrams (mg), about 200 milligrams (mg), about 300 milligrams (mg), about 400 milligrams (mg), about 500 milligrams (mg), about 750 milligrams (mg), about 1,000 milligrams (mg), or about 1,500 milligrams (mg).

In some embodiments, the provided amount of legume protein administered comprises about 5 grams (g) to about 60 grams (g). In some embodiments, the provided amount of legume protein administered comprises about 5 grams (g) to about 10 grams (g), about 5 grams (g) to about 15 grams (g), about 5 grams (g) to about 20 grams (g), about 5 grams (g) to about 25 grams (g), about 5 grams (g) to about 30 grams (g), about 5 grams (g) to about 35 grams (g), about 5 grams (g) to about 40 grams (g), about 5 grams (g) to about 45 grams (g), about 5 grams (g) to about 50 grams (g), about 5 grams (g) to about 60 grams (g), about 10 grams (g) to about 15 grams (g), about 10 grams (g) to about 20 grams (g), about 10 grams (g) to about 25 grams (g), about 10 grams (g) to about 30 grams (g), about 10 grams (g) to about 35 grams (g), about 10 grams (g) to about 40 grams (g), about 10 grams (g) to about 45 grams (g), about 10 grams (g) to about 50 grams (g), about 10 grams (g) to about 60 grams (g), about 15 grams (g) to about 20 grams (g), about 15 grams (g) to about 25 grams (g), about 15 grams (g) to about 30 grams (g), about 15 grams (g) to about 35 grams (g), about 15 grams (g) to about 40 grams (g), about 15 grams (g) to about 45 grams (g), about 15 grams (g) to about 50 grams (g), about 15 grams (g) to about 60 grams (g), about 20 grams (g) to about 25 grams (g), about 20 grams (g) to about 30 grams (g), about 20 grams (g) to about 35 grams (g), about 20 grams (g) to about 40 grams (g), about 20 grams (g) to about 45 grams (g), about 20 grams (g) to about 50 grams (g), about 20 grams (g) to about 60 grams (g), about 25 grams (g) to about 30 grams (g), about 25 grams (g) to about 35 grams (g), about 25 grams (g) to about 40 grams (g), about 25 grams (g) to about 45 grams (g), about 25 grams (g) to about 50 grams (g), about 25 grams (g) to about 60 grams (g), about 30 grams (g) to about 35 grams (g), about 30 grams (g) to about 40 grams (g), about 30 grams (g) to about 45 grams (g), about 30 grams (g) to about 50 grams (g), about 30 grams (g) to about 60 grams (g), about 35 grams (g) to about 40 grams (g), about 35 grams (g) to about 45 grams (g), about 35 grams (g) to about 50 grams (g), about 35 grams (g) to about 60 grams (g), about 40 grams (g) to about 45 grams (g), about 40 grams (g) to about 50 grams (g), about 40 grams (g) to about 60 grams (g), about 45 grams (g) to about 50 grams (g), about 45 grams (g) to about 60 grams (g), or about 50 grams (g) to about 60 grams (g). In some embodiments, the provided amount of legume protein administered comprises about 5 grams (g), about 10 grams (g), about 15 grams (g), about 20 grams (g), about 25 grams (g), about 30 grams (g), about 35 grams (g), about 40 grams (g), about 45 grams (g), about 50 grams (g), or about 60 grams (g). In some embodiments, the provided amount of legume protein administered comprises at least about 5 grams (g), about 10 grams (g), about 15 grams (g), about 20 grams (g), about 25 grams (g), about 30 grams (g), about 35 grams (g), about 40 grams (g), about 45 grams (g), or about 50 grams (g). In some embodiments, the provided amount of legume protein administered comprises at most about 10 grams (g), about 15 grams (g), about 20 grams (g), about 25 grams (g), about 30 grams (g), about 35 grams (g), about 40 grams (g), about 45 grams (g), about 50 grams (g), or about 60 grams (g).

In some embodiments, the legume protein is a pea protein. In some embodiments, the pea is a whole pea or a component thereof. In certain embodiments, the pea is a garden pea, a sugar pea, a field pea, or any combination thereof. In certain embodiments, the pea is a garden pea. In certain embodiments, the pea is a sugar pea. In certain embodiments, the pea is a field pea. In certain embodiments, the pea is any combination of a garden pea, a sugar pea, and/or a field pea. In some embodiments, the pea is a standard pea, a commoditized pea, a genetically modified pea, or a combination thereof. In certain embodiments, the pea is a smooth pea, a wrinkled pea, or a combination thereof.

In some embodiments, a composition comprising the legume protein is added. In some embodiments, a composition comprising the S53 protease (e.g., pro-Kumamolisin) is added. In some embodiments, a composition comprising the legume protein and the S53 protease (e.g., pro-Kumamolisin) is added.

In some embodiments, the foodstuff comprises sugar. In some embodiments, the sugar comprises of sucrose, lactose, maltose, or another di-, tri-, or polysaccharides that contain glucose as a monomer. In certain embodiments, the condition is cardiovascular disease. In certain embodiments, the condition is a neuropathy. In certain embodiments, the condition is diabetic nephropathy. In certain embodiments, the condition is retinopathy. In certain embodiments, the condition is cataract. In certain embodiments, the condition is bone and joint problems. In certain embodiments, the condition is a tooth infection. In certain embodiments, the condition is a gum infection.

In some embodiments, the method further comprises administering a low-carbohydrate diet. In certain embodiments, the low-carbohydrate diet comprises a diet wherein less than 65% of total energy intake per day (e.g., total calorie intake per day) is from carbohydrates. In certain embodiments, the low-carbohydrate diet comprises a diet wherein less than 60% of total energy intake per day (e.g., total calorie intake per day) is from carbohydrates. In certain embodiments, the low-carbohydrate diet comprises a diet wherein less than 50% of total energy intake per day (e.g., total calorie intake per day) is from carbohydrates. In certain embodiments, the low-carbohydrate diet comprises a diet wherein less than 45% of total energy intake per day (e.g., total calorie intake per day) is from carbohydrates. In certain embodiments, the low-carbohydrate diet comprises a diet wherein less than 40% of total energy intake per day (e.g., total calorie intake per day) is from carbohydrates. In certain embodiments, the low-carbohydrate diet comprises a diet wherein less than 35% of total energy intake per day (e.g., total calorie intake per day) is from carbohydrates. In certain embodiments, the low-carbohydrate diet comprises a diet wherein less than 30% of total energy intake per day (e.g., total caloric intake per day) is from carbohydrates. In some embodiments, the method further comprises reducing the caloric intake (e.g., total caloric intake per day) obtained from carbohydrates. In certain embodiments, reducing the caloric intake (e.g., total caloric intake per day) obtained from carbohydrates comprises reducing the amount (e.g., grams or calories) of carbohydrate intake as measured by or compared to the carbohydrate intake prior to administering a protease or composition comprising a protease to the subject.

In certain embodiments, the amount (grams or calories) of carbohydrates is reduced by about 10% to about 65%. In certain embodiments, the amount (grams or calories) of carbohydrates is reduced by about 10% to about 20%, about 10% to about 30%, about 10% to about 40%, about 10% to about 50%, about 10% to about 65%, about 20% to about 30%, about 20% to about 40%, about 20% to about 50%, about 20% to about 65%, about 30% to about 40%, about 30% to about 50%, about 30% to about 65%, about 40% to about 50%, about 40% to about 65%, or about 50% to about 65%. In certain embodiments, the amount (grams or calories) of carbohydrates is reduced by about 10%, about 20%, about 30%, about 40%, about 50%, or about 60%. In certain embodiments, the amount (grams or calories) of carbohydrates is reduced by at least about 10%, about 20%, about 30%, about 40%, 50%, 60% or about 65%.

Carbohydrates generally refer to and include to aldehyde or ketone compounds substituted with multiple hydroxyl groups, of the general formula $(CH_2O)_n$, wherein n is 3-30, as well as their oligomers and polymers. Carbohydrates can be substituted or deoxygenated at one or more positions. Carbohydrates include and/or encompass monosaccharides, disaccharides, oligosaccharides, and polysaccharides. Carbohydrates further include unmodified carbohydrates, carbohydrate derivatives, substituted carbohydrates, and modified carbohydrates. The carbohydrate derivatives or substituted carbohydrates include substituted and unsubstituted monosaccharides, disaccharides, oligosaccharides, and polysaccharides. A carbohydrate derivative or substituted carbohydrate can be deoxygenated at any corresponding C-position, and/or substituted with one or more moieties such as hydrogen, halogen, haloalkyl, carboxyl, acyl, acyloxy, amino, amido, carboxyl derivatives, alkylamino, dialkylamino, arylamino, alkoxy, aryloxy, nitro, cyano, sulfo, mercapto, imino, sulfonyl, sulfenyl, sulfinyl, sulfamoyl, carboalkoxy, carboxamido, phosphonyl, phosphinyl, phosphoryl, phosphino, thioester, thioether, oximino, hydrazino, carbamyl, phospho, phosphonato, or any other viable functional group.

Throughout this application, various embodiments may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used in the specification and claims, the singular forms "a", "an" and "the" include plural references unless the context clearly dictates otherwise. For example, the term "a sample" includes a plurality of samples, including mixtures thereof.

The terms "determining," "measuring," "evaluating," "assessing," "assaying," and "analyzing" are often used interchangeably herein to refer to forms of measurement. The terms include determining if an element is present or not (for example, detection). These terms can include quantitative, qualitative or quantitative and qualitative determinations. Assessing can be relative or absolute. "Detecting the presence of" can include determining the amount of something present in addition to determining whether it is present or absent depending on the context.

The terms "subject," "individual," or "patient" are often used interchangeably herein. A "subject" can be a biological entity containing expressed genetic materials. The biological entity can be a plant, animal, or microorganism, including, for example, bacteria, viruses, fungi, and protozoa. The subject can be tissues, cells and their progeny of a biological entity obtained in vivo or cultured in vitro. The subject can be a mammal. The mammal can be a human. The subject may be diagnosed or suspected of being at high risk for a disease. In some cases, the subject is not necessarily diagnosed or suspected of being at high risk for the disease.

As used herein, the term "about" a number refers to that number plus or minus 10% of that number. The term "about" a range refers to that range minus 10% of its lowest value and plus 10% of its greatest value.

The section headings used herein are for organizational purposes only and are not to be construed as limiting the subject matter described.

As used herein, the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps. As also used herein, in any instance or embodiment described herein, "comprising" may be replaced with "consisting essentially of" and/or "consisting of". used herein, in any instance or embodiment described

EXAMPLES

Example 1—Lowering Blood Glucose Using a Legume Protein and Pro-Kumamolisin

Protease Production

The DNA sequence (SEQ ID NO:2) of the acid protease of interest was cloned into the expression vector pET29b(+) for protease production in *E. coli*. The completed DNA construct was transformed into an expression strain of *E. coli* (BL21) and grown at 37 degrees Celsius in Terrific Broth using a baffled shake flask for 4-6 hours until the cell density (measured using OD 600) reaches 0.6. The cultures were then induced with 0.5 mM of IPTG for protease expression. The culture was grown at 30 degrees Celsius for 12 hours post induction before harvesting. The harvested cells were lysed using sonication and the protease was purified from cell lysate using IMAC chromatography.

Application of Pro-Kumamolisin in a Pea Protein Drink 30 grams of pea protein was dissolved in 330 mL of water. 14 grams of sucrose was then dissolved followed by 200 mg of acid protease (SEQ ID NO. 1). The protein drink of the study can be consumed as is or formulated with other commonly used ingredients found in protein shakes. As shown in FIG. 1 the addition of protease can lower the post-consumption blood glucose spike by more half at the blood glucose peak period. FIG. 1 shows the comparison of post-consumption blood glucose levels resulting from the intake of (i) a protein drink comprising pro-Kumamolisin and pea protein, compared against (ii) a protein drink without pro-Kumamolisin and pea protein.

Example 2—Activity of S53 Proteases at Low pH

Generally, the S53 proteases described and used herein should have the capability to thoroughly digest proteins (e.g., legume protein) in the stomach's acidic environment. Accordingly, the S53 proteases used and described herein should possess activity throughout the entire post-prandial pH range of the stomach environment. pH profile data was generated for 10 representative S53 proteases (encompassing SEQ ID NOs: 1 and 3-11). The representative S53 proteases showed optimal activity (e.g., 100% or substantially active) throughout a pH range between 2.5 to 4.5. FIG. 6 shows proteolytic activity of S53 proteases 1-10 (P1-P10) wherein S53 proteases 1-10 across pH 2 to 5.

While preferred embodiments of the present disclosure have been shown and described herein, it will be obvious to those skilled in the art that such embodiments are provided by way of example only. Numerous variations, changes, and substitutions will now occur to those skilled in the art without departing from the instant disclosure. It should be understood that various alternatives to the embodiments described herein may be employed in practicing the invention. It is intended that the following claims define the scope of the embodiments disclosed herein, and that methods and structures within the scope of these claims and their equivalents be covered thereby.

SEQUENCES

| SEQ ID NO | SEQUENCE | DESCRIPTION |
|---|---|---|
| 1 | MSDMEKPWKEEEKREVLAGHARRQAPQAVDKGPVTGDQRI SVTVVLRRORGDELEAHVERQAALAPHARVHLEREAFAAS HGASLDDFAEIRKFAEAHGLTLDRAHVAAGTAVLSGPVDA VNQAFGVELRHFDHPDGSYRSYVGDVRVPASIAPLIEAVL GLDTRPVARPHFRLRRRAEGEFEARSQSAAPTAYTPLDVA QAYQFPEGLDGQGQCIAIIELGGGYDETSLAQYFASLGVS APQVVSVSVDGATNQPTGDPNGPDGEVELDIEVAGALAPG AKIAVYFAPNTDAGFLNAITTAVHDPTHKPSIVSISWGGP EDSWAPASIAAMNRAFLDAAALGVTVLAAAGDSGSTDGEQ DGLYHVDFPAASPYVLACGGTRLVASAGRIERETVWNDGP DGGSTGGGVSRIFPLPSWQERANVPPSANPGAGSGRGVPD VAGNADPATGYEVVIDGETTVIGGTSAVAPLFAALVARIN QKLGKPVGYLNPTLYQLPPEVFHDITEGNNDIANRARIYQ AGPGWDPCTGLGSPIGIRLLQALLPSASQAQP | Protein Kumamolisin precursor [*Bacillus* sp. MN-32] Protease 3 |
| 2 | ATGAGCGATATGGAAAAACCGTGGAAAGAAGAAGAAAAAC GCGAAGTTCTGGCAGGTCATGCACGTCGTCAGGCACCGCA GGCAGTTGATAAAGGTCCGGTTACCGGTGATCAGCGTATT AGCGTTACCGTTGTTCTGCGTCGTCAGCGTGGTGATGAAC TGGAAGCACATGTTGAACGTCAGGCAGCACTGGCACCGCA TGCACGTGTTCATCTGGAACGTGAAGCATTTGCAGCAAGC CATGGTGCAAGCCTGGATGATTTTGCAGAAATTCGTAAAT TTGCCGAAGCGCATGGTCTGACCCTGGATCGTGCCCATGT TGCAGCAGGTACAGCAGTTCTGAGCGGTCCGGTTGATGCA GTTAATCAGGCATTTGGTGTTGAACTGCGTCATTTTGATC ATCCTGATGGTAGCTATCGTAGCTATGTTGGTGATGTTCG TGTTCCGGCAAGCATTGCACCGCTGATTGAAGCAGTTTTA GGTCTGGATACCCGTCCGGTTGCACGTCCGCATTTTCGTC | DNA Kumamolisin precursor [*Bacillus* sp. MN-32] Protease 3 |

-continued

| SEQ ID NO | SEQUENCE | DESCRIPTION |
|---|---|---|
| | TGCGTCGCCGTGCAGAAGGTGAATTTGAAGCACGTAGCCA GAGCGCAGCACCGACCGCATATACACCGCTGGATGTTGCA CAGGCATATCAGTTTCCGGAAGGCCTGGATGGTCAGGGTC AGTGTATTGCAATTATTGAATTAGGTGGTGGCTATGATGA AACCAGCCTGGCACAGTATTTTGCCAGCCTGGGTGTTAGC GCTCCGCAGGTTGTTAGCGTTAGCGTGGATGGTGCAACCA ATCAGCCGACAGGTGATCCGAATGGTCCGGATGGTGAAGT TGAACTGGATATTGAAGTTGCCGGTGCGCTGGCACCGGGT GCAAAATTGCAGTTTATTTTGCACCGAATACCGATGCCG GTTTTCTGAATGCAATTACCACCGCAGTTCATGATCCGAC ACATAAACCGAGCATTGTGAGCATTAGCTGGGGTGGTCCG GAAGATAGCTGGGCACCAGCCAGCATTGCAGCCATGAATC GTGCATTTCTGGATGCAGCCGCACTGGGTGTGACCGTGCT GGCAGCAGCCGGTGATAGCGGTAGCACCGATGGTGAACAG GATGGTCTGTATCATGTTGATTTTCCGGCAGCGAGCCCGT ATGTTCTGGCATGTGGTGGCACCCGTCTGGTGGCAAGCGC AGGTCGTATTGAACGTGAAACCGTTTGGAATGATGGTCCT GATGGCGGTTCAACCGGTGGTGGTGTTAGCCGTATTTTTC CGCTGCCGAGCTGGCAAGAACGTGCAAATGTTCCGCCTAG CGCAAATCCTGGTGCAGGTAGCGGTCGTGGTGTTCCGGAT GTTGCCGGTAATGCAGATCCGGCAACCGGTTATGAAGTTG TTATTGATGGTGAAACCACCGTGATTGGTGGTACAAGCGC AGTGGCACCGCTGTTTCAGCCCTGGTTGCCCGTATTAAT CAGAAACTGGGTAAACCGGTTGGTTATCTGAATCCGACAC TGTATCAGCTGCCTCCGGAAGTTTTTCATGATATTACCGA AGGCAACAACGATATTGCCAATCGTGCACGTATTTATCAG GCAGGTCCTGGTTGGGATCGTGTACCGGTCTGGGTAGCC CGATTGGTATTCGTCTGCTGCAGGCACTGCTGCCGAGTGC AAGCCAGGCACAGCCGTGA | |
| 3 | MSEPVPAAARRTIPGSERPPVDTAAAARQAVPADTRVEAT VVLRRRAELPDGPGLLTPAELAERHGADPADVELVTRTLT GLGVEVTAVDAASRRLRVAGPAGVLAEAFGTSLAQVSTPD PSGAQVTHRYRAGALSVPAELDGVVTAVLGLDDRPQARAR FRVATAAAASAGYTPIELGRVYSFPEGSDGSGQTIAIIEL GGGFAQSELDTYFAGLGISGPTVTAVGVDGGSNVAGRDPQ GADGEVLLDIEVAGALAPGADVVVYFAPNTDAGFLDAVAQ AAHATPTPAAISISWGGSEDTWTGQARTAFDAALADAAAL GVTTTVAAGDDGSTDRATDGKSHVDFPASSPHALACGGTH LDANATTGAVTSEVVWNNGAGKGATGGGVSTVFAQPSWQA SAGVPDGPGGKPGRGVPDVSAVADPQTGYRIRVDGQDLVI GGTSAVAPLWAALVARLVQAGRAKLGLLQPKLYAAPTAFR DITEGDNGAYRAGPGWDACTGLGVPVGTALASALS | Protease 1 |
| 4 | MADDSSPTTAADRPTLPGSARRPVAAAQAAGPLDDAAPLE VTLVLRRRTALPAGTGRPAPMGRAEFAETHGADPADAETV TAALTAEGLRITAVDLPSRRVQVAGDVATFSRVFGVSLSR VESPDPVADRLVPHRQRSGDLAVPAPLAGVVTAVLGLDDR PQARALFRPAAAVDTTFTPLELGRVYRFPSGTDGRGQRLA ILELGGGYTQADLDAYWTTIGLADPPTVTAVGVDGAANAP EGDPNGADGEVLLDIEVAGALAPGADLVVYFAPNTDRGFL DALSTAVHADPTPTAVSISWGQNEDEWTAQARTAMDEALA DAAAALGVTVCAAAGDDGSTDNAPDGQAHVDFPASSPHALA CGGTTLRADPDTGEVSSETVWFHGTGQGGTGGGVSAVFAV PDWQDGVRVPGDADTGRHGRGVPDVSADADPSTGYQVRVD GTDAVFGGTSAVSPLWSALTCRLAEALGQRPGLLQPLIYA GLSAGEVAAGFRDVTSGSNGAYDAGPGWDPCTGLGVPDGE ALLVRLRTALG | Protease 2 |
| 5 | MANRKMFPNSVIAIPTSGVTAHGLIVSAADPQSRDEKMDV SFSLGIPPALEKELEERVDKGETIPPQELTTKYAVDPTAA GTLQTWLKKEGFTITGVTPDRTTIYASAPASQVEASLGVH TVRVTREGQTYTAASDVPSLPEDIGGAVVNIGGLQPYRQA RKHLRSYIQTTPEADGEEPAIANAPPYLVPEILKAYDGAR LGLTGKGQEIAILIDTVPLDTDLTSFWTANGVAGSLARIT KINVKGGALPTPSGEETLDAEWASTIAPDANVRIYASGTL SFIDLDRALDRIYADALAQPKLRIVSISLGLSEAYMAKGE VDAEEARFVRFAALGVNVFVSTGDAGSNPGPDGHHANGPL AAEWMSTSPHVVAVGGTSLRLANNGQVASETGWTGSGGGK SNFQPRPAWQQGHGVPAGNQRMVPDVGAAADPNEGALVIL NGQRLQYGGTSWSAPIWAGLCALINEARQNNHKTPLPYLN SLIYPMIGSNCFRDELTGSNGAYSCGPGYDLVTGIGSPDL KQLAAKLA | Protease 4 |

SEQUENCES

| SEQ ID NO | SEQUENCE | DESCRIPTION |
|---|---|---|
| 6 | MAGVNEPYNAREDGIPLKSSARAVVPGVKLHGPTDGASRL EITVVLRRRTELPSAAADGHLTAAELASEYGASDDDVRLA TEVFTRLGADVVESDPASRRLRLSGTVEQLSSIFGTTLED ATSTAPDGATVHYRHRLGELRIPAELNGIVIAVLGLDDRP QARAHFRMLPRTTAGTSYSPVELGRVYGFPDGTDGSGQTV AIIELGGGYAQADLDAYFAGLGLATPQITSIGVDGGANQG GNDPQGADGEVLLDIEVVGALAPKAAIQVYFAPNTDAGFL DAVVAATKAAPCAISISWGQSEDQWTAQARDAFDQALADA AALGITTTVAAGDRGSSDGAADGKAHVDFPASSPHALACG GTRLEADPATGAIRSETVWNEGPDSATGGGYSKVFPRPSW QSPSAGKSGRGVPDVSAVADPQTGYRIRVDGKDMVIGGTS AVAPLWAALIARFAQAGNRRFGLIQPSLYAVSSGFRDVTV GDNGSYHAGPGWDACTGLGTPDGAALLAALKG | Protease 5 |
| 7 | MSTRAARTTPSALADLRNEPRSPLPGSEKAALADTPATTA AGIKPLRATAVAKAKPASSRKKITVSVVVPRTKPVTQAAV AGKHLTRAQFKSSHAAAPASVKAVQKFAKAFNLVSKAEPA RSTVHLTGTVKDMQDAFGVTLQEHTVGAKTLRIRQGAIYL PDSVLPHVQAVLGLDNRPQAKPHYRVGKARAAASTSFTPP QLAQLYGFPTSAKATGQTIALIELGGGFRQADITAYFKSL GIAAPSVKAVLVDGGKNAPSNANGADGEVMLDIEVAAAVA PGANIAVYFAPNTDQGFVDAIATAAHDTTNKPTIISISWG GPESSWTSQALTALDNACKDAAALGITVTAAAGDDGSDDG VGDGKKHVDFPASSPNVLACGGTKLVASNGAITSEVVWNE TANKEGATGGGISTAFFPQPTWQKSIAATKSGRGVPDVAGD ADPTTGYQVRVDGQNMVIGGTSAVAPLWAGLIALSNATNK NAAGLPQAKLYSTTGQKAFRDITSGNNGAFKAAKGWDPCT GLGSPKAASIITLLATKSSAKKKTSRAKA | Protease 6 |
| 8 | MESIMPSQPSSIPVRGSERAALPTAHVVGPAASDERLEVT LRVRPRAQLHASASEAQSLRPPGERSYLSREQLASAHGAA PEDIAKVEAFAQSHGLQVVLTSAARRCVIVSGTVAALESA FAVKLQQYRFDGGSYRGRVGPVFVSPEIGDIVEGVFGLDD RPQAIAHFKRSAHAVRAEDGAAPHAGGASFTPPQLAKLYN YPGDTDGTGQCIGIVEFGGAIRAADIRAYFKELGLPAHV NTVLVDHAHMRSDDADAEVMLDIEVAAAIAPKAQIVVYFA PNTSQGFIDAFTHAIHDTVHKPSVISVSWGGPEKDWSAQI KTQLDQVFQDAAALGVTICAASGDAGSSDENPDALASIGL TPDGLSHADFPASSPFALACGGTKLVASASAITSETVWNE DPVRSATGGGISDFFDVPGYQATANIPVSANPGGRKGRGV PDIAADADPATGYLVRVHGQDAVIGGTSAVAPLMAGLVAL LNHKLGHPVGFLNPLLYRTAGITRDITQGNNGAYAAGKGW DACTGLGVPDGAKLLDALM | Protease 7 |
| 9 | MPQSQNRVVVRGSERQPMPKAHSQHALPPTERLEVTVRLR PKAALASAAASSHAMADVPPSQRTYLSREELAAQCGASED DAQAVADFAHAHGLVVIHTDLARRSVLLAGTAADFGAAFG TQLHQYSSPEGTYRGRTGTVTVPAPLADIVQGVFGLDDRR QAEPHFQVRPGPTPAPGAIVARAAGQSFTPPQLAQLYDFP GGLDGTGQTIAVIELGGGFKPADLKAYFTGLNLPVPTVKV VSVNGGRNQPTNANSADGEVLLDIEVAAAVAPRAHLVVYF APNTSQGFLNAITTAVHDKVNNPGIISISWGGPESTWTGQ AMDQFDQAFQEAAMLGVTVCVAAGDNGSADGVADGQPHAD FPASSPFALACGGTKLTASGPTISSEVVWNEGPNSATGGG LSAHFPVPAYQQQLKFPTPPAGAKAGRGLPDVAGDADPNT GYQVRVDGQNLVIGGTSAVAPLWAGLLALLNQKLPKPVGF LNPLLYGSLAGQGVTRDITSGNNGAFAAGPGWDACTGWGS PVGGKLLAALQGGAAVA | Protease 8 |
| 10 | MSKHPLMGSERAPFDGAQSVGKADPAERLEVTVLVRRGSS DALRTRVSKLVAGNASDGHIQREDFAQQFGAAPNDMSAVR NFASQHGLSVVEEHAARRTVILSGTVAQFNDAFDVDLQQF EHAGGSYRGRTGPVHLPDELSGVVDAVLGLDNRPQARPHF RSRPPQGNVHWQSSRTGTTSSTPLQLASLYDFPAGTGQGQ CIAIIELGGGYRPADLKAYFSKLGIASPKVTTVSVDHGKN HPTGDANGPDGEVMLDIEIAGAIAPGAHIAVYFAPNTDAG FLDAVTTAIHDTIRKPSVISISWGGPESAWTEQAMTAFDQ AFQAAAALGITVCVASGDNGSGDGVNDGADHVDFPASSPY ALACGGTSVQAGKGAIAKETVWNDGANGGASGGGVSSFFA LPAWQEGLQAARAKGGTGALQMRGVPDVAGNADPATGYDV RVDGSDMVIGGTSAVAPLWAGLVARINAGKNSPAGYLNPK LYKTAAGLTDITQGNNGDFVASAGWDACTGLGRPDGNKLA GTFG | Protease 9 |

-continued

SEQUENCES

| SEQ ID NO | SEQUENCE | DESCRIPTION |
|---|---|---|
| 11 | MDETNFTSTNGSPQYIPVTGSARAIVPGATHAGHTDDNEV<br>LSVTLQLRRPSADELTAHVEALGTTPPANRKHMTHDEFEA<br>SHGASDDDLNLVTAFATEQGLSVERINKAAATVHVSGTAG<br>AFNKAFHVQLGNYQHPDFTYRGYDGPVHIPAHLTDIVTGV<br>LGLDNRPQAKPHFRVYQEAAVRSNALAAPISYTPTQVAAL<br>YNFPTNVDCSGQCIGIIELGGGYSKSNLDQYFASLGVPTP<br>TITSVSVDGGQNQPTGSPNGPDGEVDLDIEVAASVAPGAH<br>IAVYFAPNTDAGFLDAITTAVHDKTNKPSVISISWGGPEM<br>SWTTQAMQAMNNAMQSAAALGVTITVAAGDNGSTDGVNDG<br>SFHVDFPASAPYALACGGTHLVGSGSTIESETVWNDGANG<br>GATGGGVSSVFPVPSWQQKANVPPSANPGAGTGRGVPDVS<br>GDADPATGYQVLVDGQQFPIGGTSAVAPLWAGLVALANQT<br>LGKPVGYINPLLYSIPAQDNAFHDITQGNNDPNQTGQVYP<br>AGPGWDACTGLGSPNGTLLIQALGQIG | Protease 10 |
| | ATGAGCGAACCTGTTCCGGCAGCAGCACGTCGTACCATTC<br>CGGGTAGCGAACGTCCGCCTGTTGATACCGCAGCAGCAGC<br>CCGTCAGGCAGTTCCTGCAGATACCCGTGTTGAAGCAACC<br>GTTGTTCTGCGTCGTCGTGCAGAACTGCCGGATGGTCCGG<br>GTCTGCTGACACCGGCAGAACTGGCAGAACGTCATGGTGC<br>AGATCCGGCAGATGTTGAACTGGTTACCCGTACACTGACC<br>GGTCTGGGTGTTGAAGTTACCGCAGTTGATGCAGCAAGCC<br>GTCGTCTGCGTGTTGCCGGTCCGGCAGGCGTTCTGGCAGA<br>AGCATTTGGCACCAGCCTGGCACAGGTTAGCACACCGGAT<br>CCGAGCGGTGCCCAGGTTACCCATCGTTATCGTGCCGGTG<br>CACTGAGCGTTCCAGCCGAACTGGATGGTGTTGTGACCGC<br>AGTTCTGGGTTTAGATGATCGTCCGCAGGCACGTGCGCGT<br>TTTCGTGTTGCAACGGCAGCCGCAGCAAGCGCAGGTTATA<br>CCCCGATTGAACTGGGTCGTGTTTATAGCTTTCCGGAAGG<br>TAGTGATGGTAGCGGTCAGACCATTGCAATTATTGAATTA<br>GGTGGTGGTTTTGCACAGAGTGAACTGGATACCTATTTTG<br>CAGGTCTGGGTATTAGCGGTCCGACCGTTACAGCAGTTGG<br>TGTTGATGGTGGTAGCAATGTTGCAGGTCGTGATCCGCAG<br>GGTGCAGATGGTGAAGTTCTGCTGGATATTGAAGTTGCGG<br>GTGCACTGGCACCGGGTGCCGATGTTGTTGTTTATTTTGC<br>ACCGAATACCGATGCAGGTTTTCTGGATGCAGTTGCACAG<br>GCAGCACATGCAACCCCGACTCCGGCAGCCATTAGCATTA<br>GCTGGGGTGGTAGCGAAGATACCTGGACAGGTCAGGCACG<br>TACCGCCTTTGATGCGGCACTGGCAGATGCAGCCGCACTG<br>GGTGTTACCACCACCGTTGCAGCCGGTGATGATGGTAGTA<br>CCGATCGTGCAACCGATGGTAAAAGCCATGTTGATTTTCC<br>GGCAAGCAGTCCGCATGCACTGGCCTGTGGTGGCACCCAT<br>CTGGATGCCAATGCAACCACCGGTGCAGTTACCAGCGAAG<br>TTGTTTGGAATAATGGTGCAGGTAAAGGTGCAACCGGTGG<br>CGGTGTTAGCACCGTTTTTGCCCAGCCGAGCTGGCAGGCA<br>AGTGCCGGTGTTCCGGATGGCCCTGGTGGTAAACCTGGTC<br>GTGGTGTGCCGGATGTTAGCGCAGTTGCCGATCCGCAGAC<br>CGGTTATCGTATTCGTGTGGATGGTCAGGATCTGGTTATT<br>GGTGGTACAAGCGCAGTGGCACCGCTGTGGGCAGCACTGG<br>TTGCACGTCTGGTTCAGGCAGGTCGCGCAAAACTGGGCCT<br>GCTGCAGCCGAAACTGTATGCAGCACCGACCGCATTTCGT<br>GATATTACCGAAGGTGATAATGGCGCATATCGTGCAGGTC<br>CTGGTTGGGATGCATGTACAGGCCTGGGCGTTCCGGTTGG<br>CACCGCACTGGCGAGCGCACTGAGTCTCGAGCACCACCAC<br>CACCACCACTGA | Protease 1 |
| | ATGGCCGATGATAGCAGCCCGACCACCGCAGCAGATCGTC<br>CGACACTGCCTGGTAGCGCACGTCGTCCGGTTGCAGCAGC<br>ACAGGCAGCAGGTCCGCTGGATGATGCAGCACCGCTGGAA<br>GTTACCCTGGTTCTGCGTCGTCGTACCGCACTGCCAGCAG<br>GCACAGGTCGTCCGGCACCGATGGGTCGTGCAGAATTTGC<br>AGAAACCCATGGTGCAGATCCGGCAGATGCCGAAACCGTT<br>ACCGCAGCACTGACCGCAGAAGGTCTGCGTATTACCGCAG<br>TTGATCTGCCGAGCCGTCGTGTTCAGGTTGCCGGTGATGT<br>TGCAACCTTTAGCCGTGTTTTTGGTGTTAGCCTGAGCCGT<br>GTTGAAAGCCCTGATCCGGTTGCCGATCGTCTGGTTCCGC<br>ATCGTCAGCGTAGCGGTGATCTGGCAGTTCCTGCTCCGCT<br>GGCAGGCGTTGTGACCGCAGTTCTGGGTTTAGATGATCGT<br>CCGCAGGCACGTGCACTGTTTCGTCCTGCAGCAGCCGTTG<br>ATACCACCTTTACTCCGCTGGAACTGGGTCGTGTTTATCG<br>TTTTCCGAGCGGTACAGATGGTCGTGGTCAGCGTCTGGCA<br>ATTCTGGAATTAGGTGGTGGTTATACCCAGGCAGATCTGG<br>ATGCATATTGGACCACCATTGGTCTGGCAGATCCGCCTAC<br>CGTTACAGCAGTTGGTGTTGATGGTGCAGCAAATGCACCG<br>GAAGGTGATCCGAATGGTGCCGATGGTGAAGTTCTGCTGG | Protease 2 |

| SEQ ID NO | SEQUENCE | DESCRIPTION |
|---|---|---|
| | ATATTGAAGTTGCGGGTGCACTGGCACCGGGTGCCGATCT<br>GGTTGTTTATTTTGCACCGAATACCGATCGTGGTTTTCTG<br>GATGCCCTGAGCACCGCAGTGCATGCCGATCCGACACCGA<br>CCGCAGTGAGCATTAGCTGGGGTCAGAATGAAGATGAATG<br>GACCGCACAGGCACGTACCGCAATGGATGAAGCACTGGCA<br>GATGCAGCCGCACTGGGTGTTACCGTTTGTGCAGCAGCGG<br>GTGATGATGGTAGCACAGATAACGCACCGGATGGTCAGGC<br>ACATGTTGATTTTCCGGCAAGCAGTCCGCATGCGCTGGCA<br>TGTGGTGGTACAACCCTGCGTGCGGATCCGGATACCGGTG<br>AAGTTAGCAGCGAAACCGTGTGGTTTCATGGCACCGGTCA<br>AGGTGGTACTGGTGGTGTGTGAGCGCAGTTTTTGCAGTT<br>CCGGATTGGCAGGATGGTGTTCGTGTTCCGGGTGATGCAG<br>ATACCGGTCGTCATGGTCGCGGTGTTCCGGATGTTAGCGC<br>AGATGCTGATCCGAGTACCGGTTATCAGGTTCGTGTGGAT<br>GGTACGGATGCAGTGTTTGGTGGCACCAGCGCAGTTAGTC<br>CGCTGTGGTCTGCACTGACCTGTCGTCTGGCCGAAGCGCT<br>GGGACAGCGTCCGGGTCTGCTGCAGCCGCTGATTTATGCA<br>GGTCTGAGCGCAGGCGAAGTTGCAGCCGGTTTTCGTGATG<br>TTACCAGCGGTAGCAATGGTGCATACGATGCAGGTCCTGG<br>TTGGGATCCGTGCACCGGTCTGGGTGTGCCGGATGGCGAA<br>GCACTGCTGGTTCGTCTGCGTACAGCACTGGGCCTCGAGC<br>ACCACCACCACCACCACTGA | |
| | ATGGCCAACCGTAAAATGTTTCCGAATAGCGTTATTGCAA<br>TTCCGACCAGCGGTGTTACCGCACATGGTCTGATTGTTAG<br>CGCAGCAGATCCGCAGAGCCGTGATGAAAAAATGGATGTT<br>AGCTTTAGCCTGGGTATTCCGCCTGCACTGGAAAAAGAAC<br>TGGAAGAACGTGTTGATAAAGGCGAAACCATTCCGCCTCA<br>AGAACTGACCACCAAATATGCAGTTGATCCGACCGCAGCA<br>GGCACCCTGCAGACCTGGCTGAAAAAAGAAGGTTTTACCA<br>TTACCGGTGTGACTCCGGATCGTACCACCATTTATGCAAG<br>CGCACCGGCAAGCCAGGTTGAAGCAAGCCTGGGTGTTCAT<br>ACCGTTCGTGTTACCCGTGAAGGCCAGACCTATACCGCAG<br>CAAGTGATGTTCCGAGCCTGCCGGAAGATATTGGTGGTGC<br>CGTTGTTAATATTGGCGGTCTGCAGCCGTATCGTCAGGCA<br>CGTAAACATCTGCGTAGCTATATTCAGACCACACCGGAAG<br>CAGATGGTGAAGAACCGGCAATTGCAAATGCACCGCCTTA<br>TCTGGTTCCGGAAATTCTGAAAGCATATGATGGTGCACGT<br>CTGGGTCTGACCGGTAAAGGTCAAGAAATTGCCATTCTGA<br>TTGATACCGTTCCGCTGGATACCGATCTGACCAGCTTTTG<br>GACCGCAAATGGTGTTGCAGGTAGCCTGGCACGTATTACC<br>AAAATCAATGTTAAAGGTGGTGCACTGCCGACACCGAGCG<br>GTGAAGAAACCCTGGATGCAGAATGGGCAAGCACCATTGC<br>ACCGGATGCAAATGTTCGTATTTATGCCAGCGGTACACTG<br>AGCTTTATTGATCTGGATCGTGCACTGGATCGCATTTATG<br>CCGATGCACTGGCACAGCCGAAACTGCGTATTGTGAGCAT<br>TAGTCTGGGCCTGAGCGAAGCATATATGGCAAAAGGTGAA<br>GTTGATGCAGAAGAAGCACGTTTTGTTCGTTTTGCAGCAC<br>TGGGTGTTAATGTTTTTGTTAGCACCGGTGATGCCGGTAG<br>CAATCCGGGTCCTGATGGTCATCATGCAAATGGTCCGCTG<br>GCAGCAGAATGGATGAGCACCAGTCCGCATGTTGTTGCAG<br>TTGGTGGCACCAGCCTGCGTCTGGCAAATAATGGTCAGGT<br>TGCAAGCGAAACCGGTTGGACCGGTAGCGGTGGTGGTAAA<br>AGCAATTTTCAGCCTCGTCCGGCATGGCAGCAAGGTCATG<br>GTGTTCCAGCAGGTAATCAGCGTATGGTGCCGGATGTTGG<br>TGCAGCAGCCGATCCGAATGAAGGTGCACTGGTTATTCTG<br>AATGGTCAGCGTCTGCAGTATGGCGGTACAAGTTGGAGCG<br>CACCGATTTGGGCAGGTCTGTGTGCACTGATTAATGAAGC<br>ACGTCAGAACAATCATAAAACTCCGCTGCCGTATCTGAAC<br>AGCCTGATTTATCCGATGATTGGTAGCAACTGTTTTCGTG<br>ATGAACTGACCGGTTCAAATGGTGCATATAGCTGTGGTCC<br>GGGTTATGATCTGGTTACCGGTATTGGTAGTCCGGATCTG<br>AAACAGCTGGCAGCCAAACTGGCA | Protease 4 |
| | ATGGCAGGCGTTAATGAACCGTATAATGCACGTGAAGATG<br>GTATTCCGCTGAAAAGCAGCGCACGTGCAGTTGTTCCGGG<br>TGTTAAACTGCATGGTCCGACCGATGGTGCAAGCCGTCTG<br>GAAATTACCGTTGTTCTGCGTCGTCGTACCGAACTGCCGA<br>GCGCAGCAGCAGATGGTCATCTGACCGCAGCAGAACTGGC<br>AAGCGAATATGGTGCATCAGATGATGATGTTCGTCTGGCA<br>ACCGAAGTTTTTACCCGTCTGGGTGCAGATGTTGTTGAAA<br>GCGATCCGGCAAGTCGTCGTCTGCGTCTGAGCGGCACCGT<br>TGAACAGCTGAGCAGCATTTTTGGTACAACCCTGGAAGAT<br>GCAACCAGCACCGCACCGGATGGTGCCACCGTTCATTATC<br>GTCATCGTCTGGGCGAACTGCGTATTCCGGCAGAACTGAA | Protease 5 |

| SEQ ID NO | SEQUENCE | DESCRIPTION |
|---|---|---|
| | TGGTATTGTTATTGCAGTTCTGGGCTTAGATGATCGTCCG<br>CAGGCACGCGCACATTTTCGTATGCTGCCTCGTACCACCG<br>CAGGTACAAGCTATAGTCCGGTTGAACTGGGTCGTGTTTA<br>TGGTTTTCCGGATGGCACCGATGGTAGCGGTCAGACCGTT<br>GCAATTATTGAATTAGGTGGTGGTTATGCACAGGCAGATC<br>TGGATGCATATTTTGCAGGTTTAGGTCTGGCCACACCGCA<br>GATTACCAGCATTGGTGTTGATGGTGGTGCAAATCAAGGT<br>GGTAATGATCCGCAGGGTGCCGATGGTGAAGTGCTGCTGG<br>ATATTGAAGTTGTTGGTGCACTGGCACCGAAAGCAGCAAT<br>TCAGGTTTATTTTGCACCGAATACCGATGCAGGTTTTCTG<br>GATGCCGTTGTTGCAGCAACCAAAGCAGCACCGTGTGCCA<br>TTAGCATTAGCTGGGGTCAGAGCGAAGATCAGTGGACCGC<br>ACAGGCACGTGATGCATTTGATCAGGCACTGGCAGATGCA<br>GCAGCCCTGGGTATTACCACCACCGTTGCAGCCGGTGATC<br>GTGGTAGCAGTGATGGTGCCGCAGATGGTAAAGCACATGT<br>TGATTTTCCGGCAAGCAGTCCGCATGCACTGGCCTGTGGT<br>GGTACACGTCTGGAAGCAGATCCTGCAACCGGTGCAATTC<br>GTAGCGAAACCGTTTGGAATGAAGGTCCGGATAGCGCGAC<br>CGGTGGTGGCTATAGCAAAGTTTTTCCGCGTCCGAGCTGG<br>CAGAGCCCGAGTGCAGGTAAAAGCGGTCGTGGTGTGCCGG<br>ATGTTAGCGCAGTTGCAGATCCGCAGACAGGTTATCGTAT<br>TCGTGTGGATGGCAAAGATATGGTTATTGGTGGCACCTCA<br>GCAGTTGCACCGCTGTGGGCAGCACTGATTGCACGTTTTG<br>CCCAGGCAGGTAATCGTCGTTTTGGTCTGATTCAGCCGAG<br>CCTGTATGCAGTTAGCAGCGGTTTTCGTGATGTTACCGTT<br>GGTGATAATGGTAGCTATCATGCAGGTCCTGGTTGGGATG<br>CATGTACCGGTCTGGGCACCCCTGATGGTGCAGCCCTGCT<br>GGCAGCCCTGAAAGGT | |
| | ATGAGCACCCGTGCAGCACGTACCACACCGAGCGCACTGG<br>CCGATCTGCGTAATGAACCGCGTAGTCCGCTGCCTGGTAG<br>CGAAAAAGCAGCACTGGCAGATACACCGGCAACCACCGCA<br>GCAGGTATCAAACCGCTGCGTGCAACCGCAGTTGCAAAAG<br>CAAAACCGGCAAGCAGCCGCAAAAAAATCACCGTTAGCGT<br>TGTTGTTCCGCGTACCAAACCGGTTACACAGGCAGCAGTT<br>GCAGGTAAACATCTGACCCGTGCACAGTTTAAAAGCAGCC<br>ATGCAGCAGCACCGGCAAGTGTTAAAGCAGTTCAGAAATT<br>TGCCAAAGCCTTTAACCTGGTTAGCAAAGCCGAACCGGCA<br>CGTAGCACCGTTCATCTGACCGGCACCGTTAAAGATATGC<br>AGGATGCATTTGGTGTTACCCTGCAAGAACATACCGTTGG<br>TGCAAAAACCCTGCGTATTCGTCAGGGTGCAATTTATCTG<br>CCGGATAGCGTTCTGCCGCATGTTCAGGCAGTTCTGGGTT<br>TAGATAATCGTCCGCAGGCAAAACCGCATTATCGTGTTGG<br>TAAAGCACGTGCAGCAGCCAGCACCAGCTTTACCCCTCCG<br>CAGCTGGCACAGCTGTATGGTTTTCCGACCAGCGCAAAAG<br>CCACCGGTCAGACCATTGCACTGATTGAATTAGGTGGTGG<br>TTTTTCGTCAGGCAGATATTACCGCATATTTCAAAAGCCTG<br>GGTATTGCAGCACCGAGCGTTAAAGCCGTTCTGGTTGATG<br>GTGGTAAAAATGCACCGAGCAATGCAAATGGTGCAGATGG<br>TGAAGTTATGCTGGATATTGAAGTTGCAGCGGCAGTTGCA<br>CCGGGTGCCAATATTGCAGTTTATTTTGCACCGAATACCG<br>ATCAGGGTTTTGTTGATGCAATTGCGACCGCAGCACATGA<br>TACCACCAATAAACCGACCATTATTAGCATTAGCTGGGGT<br>GGTCCGGAAAGCAGCTGGACCAGCCAGGCACTGACCGCAC<br>TGGATAATGCATGTAAAGATGCAGCCGCACTGGGTATTAC<br>CGTTACAGCAGCAGCCGGTGATGATGGTTCAGATGATGGT<br>GTTGGTGATGGTAAAAAACATGTTGATTTTCCGGCAAGCT<br>CACCGAATGTTCTGGCATGTGGTGGCACCAAACTGGTTGC<br>AAGCAATGGTGCAATTACCAGCGAAGTTGTTTGGAATGAA<br>ACCGCCAATAAAGAAGGTGCAACAGGCGGAGGTATTAGCA<br>CCGCATTTCCGCAGCCGACCTGGCAGAAAAGCATTGCAGC<br>AACCAAAAGCGGTCGTGGTGTTCCGGATGTTGCGGGTGAT<br>GCAGATCCGACCACCGGTTATCAGGTTCGTGTTGATGGTC<br>AGAATATGGTTATCGGTGGTACAAGCGCAGTTGCTCCGCT<br>GTGGGCAGGTCTGATTGCCCTGAGCAATGCCACCAACAAA<br>AATGCAGCAGGTCTGCCGCAGGCCAAACTGTATAGCACCA<br>CAGGTCAGAAAGCATTTCGTGATATTACCAGTGGCAATAA<br>CGGTGCGTTTAAAGCAGCAAAAGGTTGGGATCCGTGTACC<br>GGTCTGGGTAGCCCGAAAGCCGCAAGCATTATTACCCTGC<br>TGGCCACCAAAAGCAGCGCCAAAAAGAAAACCAGCCGTGC<br>AAAAGCC | Protease 6 |
| | ATGGAAAGCATTATGCCGAGCCAGCCGAGCAGCATTCCGG<br>TTCGTGGTAGCGAACGTGCAGCACTGCCGACCGCACATGT<br>TGTTGGTCCGGCAGCAAGTGATGAACGTCTGGAAGTTACC | Protease 7 |

| SEQ ID NO | SEQUENCE | DESCRIPTION |
|---|---|---|
| | CTGCGTGTTCGTCCGCGTGCACAGCTGCATGCAAGCGCAA<br>GCGAAGCACAGAGCCTGCGTCCGCCTGGTAACGTAGCTA<br>TCTGAGCCGTGAACAGCTGGCAAGCGCACATGGTGCAGCA<br>CCGGAAGATATTGCAAAAGTTGAAGCATTTGCCCAGAGCC<br>ATGGTCTGCAGGTTGTTCTGACCAGCGCAGCACGTCGTTG<br>TGTTATTGTTAGCGGCACCGTTGCAGCCCTGGAAAGCGCA<br>TTTGCCGTTAAACTGCAGCAGTATCGTTTTGATGGTGGTA<br>GCTATCGTGGTCGTGTTGGTCCTGTTTTTGTTAGTCCGGA<br>AATTGGTGATATTGTGGAAGGTGTTTTTGGTCTGGATGAT<br>CGTCCGCAGGCAATTGCACATTTTAAACGTAGTGCACATG<br>CAGTTCGTGCCGAAGATGGTGCCGCTCCGCATGCCGGTGG<br>TGCAAGCTTTACCCCTCCGCAGCTGGCCAAACTGTATAAC<br>TATCCGGGTGATACCGATGGCACCGGTCAGTGTATTGGTA<br>TTGTTGAATTTGGTGGTGCCATTCGTGCAGCAGATATTCG<br>TGCATATTTCAAAGAACTGGGTCTGCCTGCACCGCATGTT<br>AATACCGTTCTGGTTGATCATGCACATATGCGTAGTGATG<br>ATGCAGATGCAGAAGTTATGCTGGATATTGAAGTTGCAGC<br>AGCCATTGCACCGAAAGCACAGATTGTTGTTTATTTTGCT<br>CCGAATACCAGCCAGGGTTTTATTGATGCATTTACCCATG<br>CAATTCATGACACCGTTCATAAACCGAGCGTTATTAGCGT<br>TAGCTGGGGTGGTCCGGAAAAAGATTGGAGCGCACAGATT<br>AAAACCCAGCTGGATCAGGTTTTTCAGGATGCAGCAGCAC<br>TGGGTGTTACCATTTGTGCAGCCAGCGGTGATGCAGGTAG<br>CAGTGATGAAAATCCGGATGCACTGGCAAGCATTGGTCTG<br>ACACCGGATGGTCTGAGCCATGCAGATTTTCCGGCAAGCA<br>GCCCGTTTGCACTGGCCTGTGGTGGCACCAAACTGGTTGC<br>CAGCGCCAGCGCAATTACCAGCGAAACCGTTTGGAATGAA<br>GATCCGGTGCGTAGCGCAACCGGTGGTGGTATTAGCGATT<br>TTTTTGATGTTCCGGGTTATCAGGCAACCGCAAATATTCC<br>GGTTAGCGCAAATCCTGGTGGTCGTAAAGGTCGTGGTGTT<br>CCGGATATTGCAGCCGATGCAGATCCGGCAACCGGTTATC<br>TGGTTCGTGTTCATGGTCAGGATGCCGTTATTGGTGGTAC<br>AAGCGCAGTTGCACCGCTGATGGCAGGTCTGGTTGCACTG<br>CTGAATCATAAACTGGGTCATCCGGTTGGTTTTCTGAATC<br>CGCTGCTGTATCGTACCGCAGGTATTACCCGTGATATTAC<br>CCAGGGCAATAATGGTGCATATGCCGCAGGTAAAGGTTGG<br>GATGCATGTACCGGTCTGGGTGTGCCGGATGGTGCCAAAC<br>TGCTGGATGCCCTGATG | |
| | ATGCCGCAGAGCCAGAATCGTGTTGTTGTTCGTGGTAGCG<br>AACGTCAGCCGATGCCGAAAGCACATAGCCAGCATGCACT<br>GCCTCCGACCGAACGTCTGGAAGTTACCGTTCGTCTGCGT<br>CCGAAAGCAGCACTGGCAAGCGCAGCAGCAAGCAGCCATG<br>CAATGGCAGATGTTCCGCCTAGCCAGCGTACCTATCTGAG<br>CCGTGAAGAACTGGCAGCACAGTGTGGTGCAAGCGAAGAT<br>GATGCACAGGCAGTTGCAGATTTTGCACATGCACATGGTC<br>TGGTTGTTATTCATACCGATCTGGCACGTCGTAGCGTTCT<br>GCTGGCAGGCACCGCAGCCGATTTTGGTGCAGCATTTGGC<br>ACCCAGCTGCATCAGTATAGCAGTCCGGAAGGCACCTATC<br>GTGGTCGTACCGGCACCGTGACCGTTCCGGCACCGCTGGC<br>AGATATTGTTCAGGGTGTTTTTGGTCTGGATGATCGTCGT<br>CAGGCAGAACCGCATTTTCAGGTTCGTCCGGGTCCGACAC<br>CGGCTCCGGGTGCAATTGTAGCACGTGCAGCCGGTCAGAG<br>CTTTACCCCTCCGCAGCTGGCACAGCTGTATGATTTTCCA<br>GGTGGCCTGGATGGCACCGGTCAGACCATTGCAGTTATTG<br>AATTAGGTGGTGGTTTTAAACCGGCAGATCTGAAAGCATA<br>TTTTACCGGTCTGAACCTGCCGGTGCCGACCGTTAAAGTT<br>GTTAGCGTTAATGGTGGTCGTAATCAGCCGACCAATGCAA<br>ATAGCGCAGATGGTGAAGTGCTGCTGGATATTGAAGTTGC<br>AGCAGCAGTTGCACCGCGTGCACATCTGGTGGTTTATTTT<br>GCACCGAATACCAGCCAGGGTTTTCTGAATGCAATTACCA<br>CCGCAGTTCATGATAAAGTGAATAATCCGGGTATTATCAG<br>CATTAGCTGGGGTGGTCCGGAAAGTACCTGGACCGGTCAG<br>GCAATGGATCAGTTTGATCAGGCATTTCAAGAGGCAGCAA<br>TGCTGGGTGTTACCGTTTGTGTTGCAGCGGGTGATAATGG<br>TAGTGCCGATGGTGTTGCAGATGGTCAGCCTCATGCCGAT<br>TTTCCGGCAAGCAGTCCGTTTGCACTGGCATGGTGGCA<br>CCAAACTGACCGCAAGCGGTCCGACCATTAGTAGCGAAGT<br>TGTTTGGAATGAAGGTCCGAATAGCGCAACCGGTGGTGGT<br>CTGAGCGCACATTTTCCGGTTCCGGCATATCAGCAGCAGC<br>TGAAATTTCCGACACCTCCGGCAGGCGCAAAAGCAGGTCG<br>TGGTCTGCCGGATGTTGCCGGTGATGCAGATCCGAATACC<br>GGTTATCAGGTGCGTGTTGATGGTCAGAATCTGGTTATTG<br>GTGGTACAAGCGCAGTTGCTCCGCTGTGGGCAGGTCTGCT<br>GGCCCTGCTGAATCAGAAACTGCCGAAACCGGTTGGCTTT | Protease 8 |

| SEQ ID NO | SEQUENCE | DESCRIPTION |
|---|---|---|
| | CTGAATCCGCTGCTGTATGGTAGCCTGGCAGGTCAGGGTG<br>TGACCCGTGATATTACCTCTGGTAATAATGGTGCATTTGC<br>AGCAGGTCCTGGTTGGGATGCATGTACCGGTTGGGGTAGT<br>CCGGTTGGTGGTAAACTGTTAGCAGCCCTGCAAGGTGGTG<br>CAGCCGTTGCA | |
| | ATGAGCAAACATCCGCTGATGGGTAGCGAACGTGCACCGT<br>TTGATGGTGCACAGAGCGTTGGTAAAGCAGATCCGGCAGA<br>ACGTCTGGAAGTTACCGTTCTGGTTCGTCGTGGTAGCAGT<br>GATGCCCTGCGTACCCGTGTTAGCAAACTGGTTGCAGGTA<br>ATGCAAGTGATGGTCATATTCAGCGTGAAGATTTTGCACA<br>GCAGTTTGGTGCAGCACCGAATGATATGAGCGCAGTTCGT<br>AATTTTGCAAGCCAGCATGGTCTGAGCGTTGTTGAAGAAC<br>ATGCAGCACGTCGTACCGTTATTCTGAGCGGCACCGTTGC<br>ACAGTTTAATGATGCATTTGATGTTGATCTGCAGCAGTTC<br>GAACATGCCGGTGGTAGCTATCGTGGTCGTACCGGTCCGG<br>TTCATCTGCCTGATGAACTGAGCGGTGTTGTTGATGCAGT<br>TCTGGGTTTAGATAATCGTCCGCAGGCACGTCCGCATTTT<br>CGTAGCCGTCCGCCTCAGGGTAATGTTCATTGGCAGAGCA<br>GCCGCACCGGTACAACCAGCAGCACACCGCTGCAGCTGGC<br>AAGCCTGTATGATTTTCCGGCAGGCACCGGTCAGGGTCAG<br>TGTATTGCAATTATTGAATTAGGTGGTGGTTATCGTCCGG<br>CAGATCTGAAAGCATATTTTAGTAAACTGGGTATTGCGAG<br>CCCGAAAGTTACCACCGTTAGCGTTGATCATGGTAAAAAT<br>CATCCGACCGGTGATGCAAATGGTCCGGATGGTGAAGTTA<br>TGCTGGATATTGAAATTGCCGGTGCAATTGCCCCTGGTGC<br>ACATATTGCAGTTTATTTTGCACCGAATACCGATGCAGGT<br>TTTCTGGATGCAGTGACCACCGCAATTCATGATACCATTC<br>GTAAACCGAGCGTTATTAGCATTAGCTGGGGTGGTCCGGA<br>AAGCGCATGGACCGAACAGGCAATGACCGCATTTGATCAG<br>GCATTTCAGGCAGCAGCAGCCCTGGGTATTACCGTTTGTG<br>TTGCAAGCGGTGATAATGGTAGTGGTGATGGTGTTAATGA<br>TGGTGCCGATCATGTTGATTTTCCAGCAAGCAGCCCGTAT<br>GCACTGGCATGTGGTGGCACCAGCGTTCAGGCAGGTAAAG<br>GTGCCATTGCAAAAGAAACCGTTTGGAATGATGGCGCAAA<br>TGGTGGTGCCAGCGGTGGTGGTGTTAGCAGCTTTTTTGCA<br>CTGCCTGCATGGCAAGAAGGTCTGCAGGCAGCACGTGCAA<br>AAGGTGGTACAGGTGCACTGCAGATGCGTGGTGTTCCGGA<br>TGTGGCAGGCAATGCCGATCCGGCAACCGGTTATGATGTT<br>CGTGTTGATGGTAGCGATATGGTTATTGGTGGTACAAGCG<br>CAGTTGCACCGCTGTGGGCAGGTCTGGTTGCACGTATTAA<br>TGCAGGTAAAAATAGTCCGGCAGGTTATCTGAATCCGAAA<br>CTGTATAAAACCGCAGCAGGTCTGACCGATATCACCCAGG<br>GTAATAATGGTGATTTTGTTGCCAGCGCAGGTTGGGATGC<br>ATGTACCGGTCTGGGTCGTCCTGATGGTAATAAACTGGCA<br>GGTACATTTGGT | Protease 9 |
| | ATGGACGAAACCAATTTTACCAGCACCAATGGTAGTCCGC<br>AGTATATTCCGGTTACCGGTAGCGCACGTGCAATTGTTCC<br>GGGTGCAACCCATGCAGGTCATACCGATGATAATGAAGTT<br>CTGAGCGTTACCCTGCAGCTGCGTCGTCCGAGCGCAGATG<br>AACTGACCGCACATGTTGAAGCACTGGGTACAACCCCTCC<br>GGCAAATCGTAAACATATGACCCATGATGAATTTGAAGCA<br>AGCCATGGTGCAAGTGATGATGATCTGAATCTGGTTACCG<br>CATTTGCAACCGAACAGGGTCTGAGCGTGGAACGTATTAA<br>CAAAGCAGCAGCAACCGTTCATGTTAGCGGTACAGCCGGT<br>GCATTCAATAAAGCATTTCATGTTCAGCTGGGCAATTATC<br>AGCATCCGGATTTTACCTATCGTGGTTATGATGGTCCGGT<br>TCATATTCCGGCACATCTGACCGATATTGTTACCGGTGTT<br>CTGGGTTTAGATAATCGTCCGCAGGCAAAACCGCATTTTC<br>GTGTTTATCAAGAAGCAGCAGTTCGTAGCAATGCACTGGC<br>AGCACCGATTAGCTATACCCCGACACAGGTTGCAGCACTG<br>TATAACTTTCCGACCAATGTTGATTGTAGCGGTCAGTGTA<br>TTGGCATTATTGAATTAGGTGGTGGCTACAGCAAAAGCAA<br>TCTGGATCAGTATTTTGCAAGCCTGGGTGTTCCGACACCG<br>ACCATTACCAGCGTTAGCGTTGATGGTGGTCAGAATCAGC<br>CGACCGGTAGTCCGAATGGTCCGGATGGTGAAGTTGATCT<br>GGATATTGAAGTTGCAGCAAGCGTTGCACCGGGTGCACAT<br>ATTGCAGTTTATTTTGCACCGAATACCGATGCAGGTTTTC<br>TGGATGCAATTACCACCGCAGTTCATGACAAAACCAATAA<br>ACCGAGCGTTATTAGCATTAGCTGGGGTGGTCCGGAAATG<br>AGCTGGACCACACAGGCAATGCAGGCCATGAATAATGCAA<br>TGCAGAGCGCAGCCGCACTGGGTGTTACCATTACCGTTGC<br>AGCCGGTGATAATGGTAGCACCGATGGTGTTAATGATGGT<br>AGCTTTCATGTTGATTTTCCGGCAAGCGCACCGTATGCGC | Protease 10 |

| SEQUENCES | | |
|---|---|---|
| SEQ ID NO | SEQUENCE | DESCRIPTION |
| | TGGCATGTGGTGGCACCCATCTGGTTGGTAGCGGTAGCAC<br>CATTGAAAGCGAAACCGTTTGGAATGATGGTGCAAATGGT<br>GGTGCGACCGGTGGTGGTGTTAGCAGCGTTTTTCCGGTTC<br>CGAGCTGGCAGCAGAAAGCAAATGTTCCGCCTAGCGCAAA<br>TCCTGGTGCAGGCACCGGTCGTGGCGTTCCGGATGTGAGC<br>GGTGATGCAGATCCGGCAACCGGTTATCAGGTTCTGGTTG<br>ATGGTCAGCAGTTTCCGATTGGTGGTACAAGCGCAGTTGC<br>ACCGCTGTGGGCAGGTCTGGTTGCACTGGCCAATCAGACG<br>CTGGGTAAACCGGTTGGTTATATCAATCCGCTGCTGTATA<br>GCATTCCTGCACAGGATAATGCCTTTCATGATATTACCCA<br>GGGCAATAATGATCCGAATCAGACCGGTCAGGTTTATCCG<br>GCAGGTCCAGGTTGGGATGCATGTACCGGTCTGGGTTCAC<br>CGAATGGCACCCTGCTGATTCAGGCACTGGGTCAGATTGG<br>T | |

---

What is claimed is:

1. A method of reducing an increase in blood glucose in a subject upon consumption of a composition comprising a legume protein, the method comprising:
administering an S53 family protease to the subject, wherein the administering reduces the increase in blood glucose in the subject upon consumption of the composition wherein the legume protein is a pea protein.

2. The method of claim 1, wherein the S53 family protease comprises an active site comprising amino acid residues E266, F295, S316, W317, G318, A349, A350, G351, D352, S353, D367, G462, G463, T464, S465, and A466 of SEQ ID NO:1.

3. The method of claim 1, wherein the composition further comprises a sugar.

4. The method of claim 1, wherein the composition further comprises a fruit.

5. The method of claim 1, wherein the S53 family protease is administered with the composition.

6. The method of claim 1, wherein the S53 family protease is administered after the composition.

7. The method of claim 1, wherein the S53 family protease comprises an amino acid sequence having at least 90% sequence identity to identity to SEQ ID NO: 1.

8. The method of claim 1, where the S53 family protease comprises the amino acid sequence of SEQ ID NO: 1.

9. The method of claim 1, wherein the S53 family protease is active at a pH range between about pH 2 and about pH 5.

10. The method of claim 1, wherein the pea protein is derived from a pea.

11. The method of claim 1, wherein the increase in blood sugar is reduced relative to administering a composition that does not comprise the S53 family protease.

12. The method of claim 1, wherein the subject self-administers the composition.

13. The method of claim 1, wherein the subject is a mammal.

14. The method of claim 13, wherein the mammal is a human.

15. The method of claim 14, wherein the human has hyperglycemia.

16. A method of reducing an increase in blood glucose in a subject upon consumption of a composition comprising a legume protein, the method comprising:
administering an S53 protease to the subject, wherein the administering reduces the increase in blood glucose in the subject upon consumption of the composition, wherein the subject is a human with hyperglycemia.

17. The method of claim 16, wherein the S53 family protease comprises an active site comprising amino acid residues E266, F295, S316, W317, G318, A349, A350, G351, D352, S353, D367, G462, G463, T464, S465, and A466 of SEQ ID NO:1.

18. The method of claim 16, wherein the composition further comprises a sugar.

19. The method of claim 16, wherein the composition further comprises a fruit.

20. The method of claim 16, wherein the S53 family protease is administered with the composition.

21. The method of claim 16, wherein the S53 family protease is administered after the composition.

22. The method of claim 16, wherein the S53 family protease comprises an amino acid sequence having at least 90% sequence identity to identity to SEQ ID NO: 1.

23. The method of claim 1, where the S53 family protease comprises the amino acid sequence of SEQ ID NO: 1.

24. The method of claim 16, wherein the S53 family protease is active at a pH range between about pH 2 and about pH 5.

25. The method of claim 16, wherein the increase in blood sugar is reduced relative to administering a composition that does not comprise the S53 family protease.

26. The method of claim 16, wherein the subject self-administers the composition.

27. The method of claim 16, wherein the subject is a mammal.

28. The method of claim 16, wherein the legume protein is a pea protein.

29. The method of claim 28, wherein the pea protein is derived from a pea.

* * * * *

UNITED STATES PATENT AND TRADEMARK OFFICE
CERTIFICATE OF CORRECTION

PATENT NO. : 11,821,013 B2  
APPLICATION NO. : 18/184476  
DATED : November 21, 2023  
INVENTOR(S) : Wai Shun Mak Page 1 of 1

It is certified that error appears in the above-identified patent and that said Letters Patent is hereby corrected as shown below:

In the Claims

In Claim 7, Line number (24), the claim should be changed as follows:
"90% sequence identity to identity to SEQ ID NO: 1."
-- 90% sequence identity to SEQ ID NO: 1. --

In Claim 16, Line number (4), the claim should be changed as follows:
"administering an S53 protease to the subject, wherein the"
-- administering an S53 family protease to the subject, wherein the --

In Claim 22, Line number (24), the claim should be changed as follows:
"90% sequence identity to identity to SEQ ID NO: 1."
-- 90% sequence identity to SEQ ID NO: 1. --

Signed and Sealed this  
Second Day of January, 2024

Katherine Kelly Vidal  
*Director of the United States Patent and Trademark Office*